US012409237B1

(12) United States Patent
Shultz et al.

(10) Patent No.: US 12,409,237 B1
(45) Date of Patent: ***Sep. 9, 2025

(54) METHODS AND MODELS FOR ASSESSING EFFICACY OF IMMUNOTHERAPIES

(71) Applicants: The Jackson Laboratory, Bar Harbor, ME (US); University of Massachusetts, Westborough, MA (US)

(72) Inventors: Leonard D. Shultz, Bar Harbor, ME (US); James Keck, Bar Harbor, ME (US); Dale L. Greiner, Westborough, MA (US); Michael A. Brehm, Westborough, MA (US)

(73) Assignees: The Jackson Laboratory, Bar Harbor, ME (US); University of Massachusetts, Westborough, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/758,838

(22) Filed: Jun. 28, 2024

Related U.S. Application Data

(63) Continuation of application No. 16/465,006, filed as application No. PCT/US2017/063948 on Nov. 30, 2017.

(60) Provisional application No. 62/565,783, filed on Sep. 29, 2017, provisional application No. 62/428,131, filed on Nov. 30, 2016.

(51) Int. Cl.
*A01K 67/0278* (2024.01)
*A01K 67/0271* (2024.01)
*A61K 49/00* (2006.01)

(52) U.S. Cl.
CPC .................. *A61K 49/0008* (2013.01)

(58) Field of Classification Search
None
See application file for complete search history.

(56) References Cited

U.S. PATENT DOCUMENTS

| | | |
|---|---|---|
| 2015/0282460 A1 | 10/2015 | Shi et al. |
| 2018/0187210 A1 | 7/2018 | Keck |
| 2018/0213755 A1 | 8/2018 | Ito et al. |
| 2018/0325085 A1 | 11/2018 | Wiles et al. |
| 2019/0016778 A1* | 1/2019 | Bernett .............. C07K 16/2815 |
| 2019/0274290 A1 | 9/2019 | Shultz |
| 2019/0320633 A1* | 10/2019 | Shultz ................ A01K 67/0271 |
| 2020/0024356 A1 | 1/2020 | Smith et al. |
| 2020/0236916 A1 | 7/2020 | Shultz et al. |
| 2021/0379195 A1 | 12/2021 | Palchaudhuri et al. |

FOREIGN PATENT DOCUMENTS

| | | | |
|---|---|---|---|
| CN | 103547148 A | 1/2014 | |
| WO | 01/15521 A1 | 3/2001 | |
| WO | 2006/044962 A1 | 4/2006 | |
| WO | 2012/112544 A2 | 8/2012 | |
| WO | WO-2014039782 A2 * | 3/2014 | .......... A01K 67/027 |
| WO | 2014/071397 A2 | 5/2014 | |
| WO | 2015/057758 A1 | 4/2015 | |
| WO | 2015/179317 A2 | 11/2015 | |
| WO | 2016/168212 A1 | 10/2016 | |
| WO | 2016/189799 A1 | 12/2016 | |
| WO | 2016/209865 A1 | 12/2016 | |

OTHER PUBLICATIONS

Wikipedia definition of NSG mouse (Year: 2022).*
Jackson Labs description of Congenic (Year: 2022).*
Jackson Labs description of Genetic Drift (Year: 2022).*
Billerbeck (Blood, 2011, vol. 117, No. 11, p. 3076-3086, DOI 10.1182/blood-2010-08-301507, Mar. 17, 2011) (Year: 2011).*
Jangalwe et al (Immunity, Inflammation and Disease 2016; 4(4): 427-440, doi: 10.1002/iid3.124) (Year: 2016).*
Bryce et al (J Allergy Clin Immunol vol. 138, No. 3, http://dx.doi.org/10.1016/j.jaci.2016.01.049 ) (Year: 2016).*
Rathinam et al (Blood. 2011; 118(11):3119-3128, DOI 10.1182/blood-2010-12-326926 (Year: 2011).*
[No Author Listed], Definition of NSG mouse. Wikipedia. 2022. Retrieved from <https://en.wikipedia.org/w/index.php?title=NSG_mouse&oldid=1095732832>. 5 pages.
Aryee et al., Enhanced development of functional human NK cells in NOD-*scid*-IL2rg$^{null}$ mice expressing human IL15. FASEB J. Sep. 2022;36(9):e22476. doi: 10.1096/fj.202200045R.
Belizário, J.E., Immunodeficient Mouse Models: An Overview. The Open Immunology Journal. 2009;2(1):79-85. doi: 10.2174/1874226200902010079. Epub Dec. 8, 2009.
Brehm et al., Engraftment of human HSCs in nonirradiated newborn NOD-scid IL2r null mice is enhanced by transgenic expression of membrane-bound human SCF. Blood. Mar. 22, 2012;119(12):2778-88. doi: 10.1182/blood-2011-05-353243. Epub Jan. 12, 2012.
Cany et al., Combined IL-15 and IL-12 drives the generation of CD34+-derived natural killer cells with superior maturation and alloreactivity potential following adoptive transfer. Oncoimmunology. Apr. 1, 2015;4(7):e1017701. doi: 10.1080/2162402X.2015.1017701.
Cany et al., Natural killer cells generated from cord blood hematopoietic progenitor cells efficiently target bone marrow-residing human leukemia cells in NOD/SCID/IL2Rg(null) mice. PLoS One. Jun. 5, 2013;8(6):e64384. doi: 10.1371/journal.pone.0064384.

(Continued)

*Primary Examiner* — Peter Paras, Jr.
*Assistant Examiner* — Khoa Nhat Tran
(74) *Attorney, Agent, or Firm* — Wolf, Greenfield & Sacks, P.C.

(57) ABSTRACT

A method of identifying anti-tumor activity of a test substance is provided along with a genetically-modified, immunodeficient mouse and methods of use, wherein the genetically-modified, immunodeficient mouse enables in vivo investigation of the interactions between the human immune system and human cancer.

10 Claims, 12 Drawing Sheets

Specification includes a Sequence Listing.

(56) References Cited

OTHER PUBLICATIONS

Elpek et al., Mature natural killer cells with phenotypic and functional alterations accumulate upon sustained stimulation with IL-15/IL-15Rα complexes. Proc Natl Acad Sci U S A. Dec. 14, 2010;107(50):21647-52. doi: 10.1073/pnas.1012128107. Epub Nov. 22, 2010.

Fehniger et al., Fatal leukemia in interleukin 15 transgenic mice follows early expansions in natural killer and memory phenotype CD8+ T cells. J Exp Med. Jan. 15, 2001;193(2):219-31. doi: 10.1084/jem.193.2.219.

Fehniger et al., Fatal leukemia in interleukin-15 transgenic mice. Blood Cells Mol Dis. Jan.-Feb. 2001;27(1):223-30. doi: 10.1006/bcmd.2001.0379.

Fehniger et al., Interleukin 15: biology and relevance to human disease. Blood. Jan. 1, 2001;97(1):14-32. doi: 10.1182/blood.v97.1.14.

GenBank Submission; NIH/NCBI, Accession No. NM_000757.5. *Homo sapiens* colony stimulating factor 1 (CSF1); transcript variant 1, mRNA. Oct. 28, 2018. 5 pages.

GenBank Submission; NIH/NCBI, Accession No. NM_172210.2. *Homo sapiens* colony stimulating factor 1 (CSF1); transcript variant 2, mRNA. May 14, 2019. 4 pages.

GenBank Submission; NIH/NCBI, Accession No. NM_172211.3. *Homo sapiens* colony stimulating factor 1 (CSF1); transcript variant 3, mRNA. May 14, 2019. 5 pages.

GenBank Submission; NIH/NCBI, Accession No. NM_172212.2. *Homo sapiens* colony stimulating factor 1 (CSF1); transcript variant 4, mRNA. May 14, 2019. 5 pages.

GenBank Submission; NIH/NCBI, Accession No. NP_000748.3. macrophage colony-stimulating factor 1 isoform a precursor [*Homo sapiens*]. Oct. 28, 2018. 3 pages.

GenBank Submission; NIH/NCBI, Accession No. NP_757349.1. macrophage colony- stimulating factor 1 isoform c precursor [*Homo sapiens*]. May 14, 2019. 3 pages.

GenBank Submission; NIH/NCBI, Accession No. NP_757350.1. macrophage colony-stimulating factor 1 isoform a precursor [*Homo sapiens*]. May 14, 2019. 3 pages.

GenBank Submission; NIH/NCBI, Accession No. NP_757351.1. macrophage colony-stimulating factor 1 isoform a precursor [*Homo sapiens*]. May 14, 2019. 4 pages.

Huntington et al., IL-15 trans-presentation promotes human NK cell development and differentiation in vivo. J Exp Med. Jan. 16, 2009;206(1):25-34. doi: 10.1084/jem.20082013. Epub Dec. 22, 2008.

Ito et al., NOD/SCID/gamma(c)(null) mouse: an excellent recipient mouse model for engraftment of human cells. Blood. Nov. 1, 2002;100(9):3175-82. doi: 10.1182/blood-2001-12-0207.

Katano et al., Improved Detection of in vivo Human NK Cell-Mediated Antibody-Dependent Cellular Cytotoxicity Using a Novel NOG-FcγR-Deficient Human IL-15 Transgenic Mouse. Front Immunol. Oct. 7, 2020;11:532684. doi: 10.3389/fimmu.2020.532684.

Katano et al., Long-term maintenance of peripheral blood derived human NK cells in a novel human IL-15-transgenic NOG mouse. Sci Rep. Dec. 8, 2017;7(1):17230. doi: 10.1038/s41598-017-17442-7.

Kim et al., Serum cytokine profiles in healthy young and elderly population assessed using multiplexed bead-based immunoassays. J Transl Med. Jul. 20, 2011;9:113. doi: 10.1186/1479-5876-9-113.

Kwant-Mitchell et al., Development of functional human NK cells in an immunodeficient mouse model with the ability to provide protection against tumor challenge. PLoS One. Dec. 21, 2009;4(12):e8379. doi: 10.1371/journal.pone.0008379.

Lee et al., Engrafted human cells generate adaptive immune responses to *Mycobacterium bovis* BCG infection in humanized mice. BMC Immunol. Dec. 7, 2013;14:53. doi: 10.1186/1471-2172-14-53.

Nagatani et al., Comparison of biological features between severely immuno-deficient NOD/Shi-scid Il2rgnull and NOD/LtSz-scid Il2rgnull mice. Exp Anim. Nov. 6, 2019;68(4):471-482. doi: 10.1538/expanim.19-0024. Epub May 21, 2019.

Pearson et al., Non-obese diabetic-recombination activating gene-1 (NOD-Rag1 null) interleukin (IL)-2 receptor common gamma chain (IL2r gamma null) null mice: a radioresistant model for human lymphohaematopoietic engraftment. Clin Exp Immunol. Nov. 2008;154(2):270-84. doi: 10.1111/j.1365-2249.2008.03753.x. Epub Sep. 8, 2008.

Rettman et al., Development of NK humanized mice models for the in vivo evaluation of NK cell engagers. Permanent Abstract #4247. Sanofi Oncology. Presented at American Association for Cancer Research (AACR) 2022 Annual Meeting. Apr. 13, 2022. Poster. 1 page.

Shultz et al., Human lymphoid and myeloid cell development in NOD/LtSz-scid IL2R gamma null mice engrafted with mobilized human hemopoietic stem cells. J Immunol. May 15, 2005;174(10):6477-89. doi: 10.4049/jimmunol.174.10.6477.

Svoboda et al., Human iPSC-derived microglia assume a primary microglia-like state after transplantation into the neonatal mouse brain. Proc Natl Acad Sci U S A. Dec. 10, 2019;116(50):25293-25303. doi: 10.1073/pnas.1913541116. Epub Nov. 26, 2019.

Walsh et al., Humanized Mouse Models of Clinical Disease. Annu Rev Pathol. Jan. 24, 2017;12:187-215. doi: 10.1146/annurev-pathol-052016-100332. Epub Dec. 5, 2016.

Wunderlich et al., AML xenograft efficiency is significantly improved in NOD/SCID-IL2RG mice constitutively expressing human SCF, GM-CSF and IL-3. Leukemia. Oct. 2010;24(10):1785-8. doi: 10.1038/leu.2010.158. Epub Aug. 5, 2010.

Yang et al., In vivo quantitative and qualitative assessment of foreign body giant cell formation on biomaterials in mice deficient in natural killer lymphocyte subsets, mast cells, or the interleukin-4 receptorα and in severe combined immunodeficient mice. J Biomed Mater Res A. Jun. 2014;102(6):2017-23. doi: 10.1002/jbm.a.35152. Epub Mar. 19, 2014.

Yao et al., NSG™-Quad mice, a new humanized mouse model with improved human innate immune cell development. European Journal of Cancer. Dec. 2016;69(S1):S113.

Yurasov et al., Severe combined immunodeficiency mice engrafted with human T cells, B cells, and myeloid cells after transplantation with human fetal bone marrow or liver cells and implanted with human fetal thymus: a model for studying human gene therapy. Blood. Mar. 1, 1997;89(5):1800-10.

Abeynaike et al., Human Hematopoietic Stem Cell Engrafted IL-15 Transgenic NSG Mice Support Robust NK Cell Responses and Sustained HIV-1 Infection. Viruses. Jan. 27, 2023;15(2):365. doi: 10.3390/v15020365.

Coughlan et al., Myeloid Engraftment in Humanized Mice: Impact of Granulocyte-Colony Stimulating Factor Treatment and Transgenic Mouse Strain. Stem Cells Dev. Apr. 16, 2016;25(7):530-41. doi: 10.1089/scd.2015.0289.

Janke et al., Development of Mast Cell and Eosinophil Hyperplasia and HLH/MAS-Like Disease in NSG-SGM3 Mice Receiving Human CD34+ Hematopoietic Stem Cells or Patient-Derived Leukemia Xenografts. Vet Pathol. Jan. 2021;58(1):181-204. doi: 10.1177/0300985820970144. Epub Nov. 19, 2020.

Macchiarini et al., Humanized mice: are we there yet? J Exp Med. Nov. 21, 2005;202(10):1307-11. doi: 10.1084/jem.20051547.

Shultz et al., Humanized mice in translational biomedical research. Nat Rev Immunol. Feb. 2007;7(2):118-30. doi: 10.1038/nri2017.

* cited by examiner

SEQUENCE LISTING

Sequence total quantity: 25
SEQ ID NO: 1              moltype = DNA   length = 1662
FEATURE                   Location/Qualifiers
source                    1..1662
                          mol_type = genomic DNA
                          organism = Homo sapiens
SEQUENCE: 1
atgaccgcgc cggggcgccgc cgggcgctgc cctcccacga catggctggg ctccctgctg   60
ttgttggtct gtctcctggc gagcaggagt atcaccgagg aggtgtcgga gtactgtagc  120
cacatgattg ggagtggaca cctgcagtct ctgcagcggc tgattgacag tcagatgagg  180
acctcgtgcc aaattacatt tgagtttgta gaccaggaac agttgaaaga tccagtgtgc  240
tacctttaaga aggcatttct cctggtacaa gacataatgg aggacaccat gcgcttcaga  300
gataacaccc ccaatgccat cgccattgtg cagctgcagg aactctcttt gaggctgaag  360
agctgcttca ccaaggatta tgaagagcat gacaaggcct gcgtccgaac tttctatgag  420
acacctctcc agttgctgga aaggtcaag aatgtctttta atgaaacaaa gaatctcctt  480
gacaaggact ggaatatttt cagcaagaac tgcaacaaca gctttgctga atgctccagc  540
caagatgtgg tgaccaagcc tgattgcaac tgcctgtacc ccaaagccat ccctagcagt  600
gacccggcc ctgtctcccc tcatcagccc ctcgcccct ccatggcccc tgtggctggc  660
ttgacctggg aggactctga gggaactgag ggcagctccc tcttgcctgg tgagcagccc  720
ctgcacacag tggatccagg cagtgccaag cagcggccac ccaggagcac ctgccagagc  780
tttgagccgc cagagacccc agttgtcaag gacagcacca tcggtggctc accacagcct  840

```
cgcccctctg tcggggcctt caaccccggg atggaggata ttcttgactc tgcaatgggc    900
actaattggg tcccagaaga agcctctgga gaggccagtg agattcccgt accccaaggg    960
acagagcttt ccccctccag gccaggaggg ggcagcatgc agacagagcc cgccagaccc   1020
agcaacttcc tctcagcatc ttctccactc cctgcatcag caaagggcca acagccggca   1080
gatgtaactg gtaccgcctt gcccaggtg ggccccgtgg ggcccactgg ccaggactgg   1140
aatcacaccc cccagaagac agaccatcca tctgccctgc tcagagaccc ccggagcca   1200
ggctctccca ggatctcatc actgcgcccc cagggcctca gcaacccctc caccctctct   1260
gctcagccac agctttccag aagccactcc tcgggcagcg tgctgcccct tggggagctg   1320
gagggcagga ggagcaccag ggatcggagg agccccgcag agccagaagg aggaccagca   1380
agtgaagggg cagccaggcc cctgccccgt tttaactccg ttcctttgac tgcacaggc   1440
catgagaggc agtccgaggg atcccagc ccgcagctcc aggagtctgt cttccacctg   1500
ctggtgccca gtgtcatcct ggtcttgctg gccgtcggag gcctcttgtt ctacaggtgg   1560
aggcggcgga gccatcaaga gcctcagaga gcggattctc ccttggagca accagagggc   1620
agcccctga ctcaggatga cagacaggtg gaactgccag tg                       1662
```

SEQ ID NO: 2             moltype = DNA  length = 1314
FEATURE              Location/Qualifiers
source               1..1314
                       mol_type = genomic DNA
                       organism = Homo sapiens
SEQUENCE: 2

```
atgaccgcgc cgggcgccgc cgggcgctgc cctcccacga catggctggg ctccctgctg     60
ttgttggtct gtctcctggc gagcaggagt atcaccgagg aggtgtcgga gtactgtagc    120
cacatgattg ggagtggaca cctgcagtct ctgcagcggc tgattgacag tcagatggag    180
acctcgtgcc aaattacatt tgagtttgta gaccaggaac agttgaaaga tccagtgtgc    240
taccttaaga aggcatttct cctggtacaa gacataatgg aggacaccat gcgcttcaga    300
gataacaccc ccaatgccat cgccattgtg cagctgcagg aactctcttt gaggctgaag    360
agctgcttca ccaaggatta tgaagagcat gacaaggcct cgctccgaac tttctatgag    420
acacctctcc agttgctgga aaggtcaag aatgtcttta tgaaacaaa gaatctcctt    480
gacaaggact ggaatatttt cagcaagaac tgcaacaaca gctttgctga atgctccagc    540
caagatgtgg tgaccaagcc tgattgcaac tgcctgtacc ccaaagccat ccctagcagt    600
gacccggcct ctgtctcccc tcatcagccc ctcgccccct ccatgccccc tgtggctggc    660
ttgacctggg aggactctga gggaactgag ggcagctccc tcttgcctgg tgagcagccc    720
ctgcacacag tggatccagg cagtgccaag cagtcggcca ccaggagcac ctgcagagc    780
tttgagccgc cagagacccc agttgtcaag gacagccca tcggtggctc accacagcct    840
cgcccctctg tcggggcctt caaccccggg atggaggata ttcttgactc tgcaatgggc    900
actaattggg tcccagaaga agcctctgga gaggccagtg agattcccgt accccaaggg    960
acagagcttt ccccctccag gccaggaggg ggcagcatgc agacagagcc cgccagaccc   1020
agcaacttcc tctcagcatc ttctccactc cctgcatcag caaagggcca acagccggca   1080
gatgtaactg gccatgagag gcagtccgag ggatcctcca gcccgcagct ccaggagtct   1140
gtcttccacc tgctggtgcc cagtgtcatc ctggtcttgc tggccgtcgg aggcctcttg   1200
ttctacaggt ggaggcggcg gagccatcaa gagcctcaga gcggattc tcccttggag   1260
caaccagagg gcagccccct gactcaggat gacagacagg tggaactgcc agtg         1314
```

SEQ ID NO: 3             moltype = DNA  length = 619
FEATURE              Location/Qualifiers
source               1..619
                       mol_type = genomic DNA
                       organism = Homo sapiens
SEQUENCE: 3

```
atgaccgcgc cgggcgccgc cgggcgctgc cctcccacga catggctggg ctccctgctg     60
ttgttggtct gtctcctggc gagcaggagt atcaccgagg aggtgtcgga gtactgtagc    120
cacatgattg ggagtggaca cctgcagtct ctgcagcggc tgattgacag tcagatggag    180
acctcgtgcc aaattacatt tgagtttgta gaccaggaac agttgaaaga tccagtgtgc    240
taccttaaga aggcatttct cctggtacaa gacataatgg aggacaccat gcgcttcaga    300
gataacaccc ccaatgccat cgccattgtg cagctgcagg aactctcttt gaggctgaag    360
agctgcttca ccaaggatta tgaagagcat gacaaggcct cgctccgaac tttctatgag    420
acacctctcc agttgctgga aaggtcaag aatgtcttta tgaaacaaa gaatctcctt    480
gacaaggact ggaatatttt cagcaagaac tgcaacaaca gctttgctga atgctccagc    540
caaggccatg agaggcagtc cgaggatcc tccagcccgc agctccagga gtctgtcttc    600
cacctgctgg tgcccagtg                                                 619
```

SEQ ID NO: 4             moltype = DNA  length = 1662
FEATURE              Location/Qualifiers
source               1..1662
                       mol_type = genomic DNA
                       organism = Homo sapiens
SEQUENCE: 4

```
atgaccgcgc cgggcgccgc cgggcgctgc cctcccacga catggctggg ctccctgctg     60
ttgttggtct gtctcctggc gagcaggagt atcaccgagg aggtgtcgga gtactgtagc    120
cacatgattg ggagtggaca cctgcagtct ctgcagcggc tgattgacag tcagatggag    180
acctcgtgcc aaattacatt tgagtttgta gaccaggaac agttgaaaga tccagtgtgc    240
taccttaaga aggcatttct cctggtacaa gacataatgg aggacaccat gcgcttcaga    300
gataacaccc ccaatgccat cgccattgtg cagctgcagg aactctcttt gaggctgaag    360
agctgcttca ccaaggatta tgaagagcat gacaaggcct cgctccgaac tttctatgag    420
acacctctcc agttgctgga aaggtcaag aatgtcttta tgaaacaaa gaatctcctt    480
gacaaggact ggaatatttt cagcaagaac tgcaacaaca gctttgctga atgctccagc    540
caagatgtgg tgaccaagcc tgattgcaac tgcctgtacc ccaaagccat ccctagcagt    600
gacccggcct ctgtctcccc tcatcagccc ctcgccccct ccatgccccc tgtggctggc    660
```

-continued

```
ttgacctggg aggactctga gggaactgag ggcagctccc tcttgcctgg tgagcagccc    720
ctgcacacag tggatccagg cagtgccaag cagcggccac ccaggagcac ctgccagagc    780
tttgagccgc cagagacccc agttgtcaag gacagcacca tcgtggctca accacagcct    840
cgcccctctg tcgggccctt caaccccggg atggaggata ttcttgactc tgcaatgggc    900
actaattggg tcccagaaga agcctctgga gaggccagtg agattcccgt ccccaagggg    960
acagagcttt ccccctccag gccaggaggg ggcagcatgc agacagagcc cgccagaccc   1020
agcaacttcc tctcagcatc ttctccactc cctgcatcag caaagggcca acagccggca   1080
gatgtaactg gtaccgcctt gcccagggtg ggccccgtga ggcccactgg ccaggactgg   1140
aatcacaccc cccagaagac agaccatcca tctgccctgc tcagagaccc cccggagcca   1200
ggctctccca ggatctcatc actgcgcccc cagggcctca gcaaccccctc caccctctct   1260
gctcagccac agctttccag aagccactcc tcgggcagcg tgctgcccct tggggagctg   1320
gagggcagga ggagcaccag ggatcggagg agccccgcag agccagaagg aggaccagca   1380
agtgaagggg cagccaggcc cctgcccgt tttaactccg ttcctttgac tgacacaggc   1440
catgagaggc agtccgaggg atcctccagc ccgcagctcc aggagtctgt cttccacctg   1500
ctggtgccca gtgtcatcct ggtcttgctg gccgtcggag gcctcttgtt ctacaggtgg   1560
aggcggcgga gccatcaaga gcctcagaga gcggattctc ccttggagca accagagggc   1620
agccccctga ctcaggatga cagacaggtg gaactgccag tg                      1662

SEQ ID NO: 5              moltype = AA   length = 554
FEATURE                   Location/Qualifiers
source                    1..554
                          mol_type = protein
                          organism = Homo sapiens
SEQUENCE: 5
MTAPGAAGRC PPTTWLGSLL LLVCLLASRS ITEEVSEYCS HMIGSGHLQS LQRLIDSQME    60
TSCQITFEFV DQEQLKDPVC YLKKAFLLVQ DIMEDTMRFR DNTPNAIAIV QLQELSLRLK   120
SCFTKDYEEH DKACVRTFYE TPLQLLEKVK NVFNETKNLL DKDWNIFSKN CNNSFAECSS   180
QDVVTKPDCN CLYPKAIPSS DPASVSPHQP LAPSMAPVAG LTWEDSEGTE GSSLLPGEQP   240
LHTVDPGSAK QRPPRSTCQS FEPPETPVVK DSTIGGSPQP RPSVGAFNPG MEDILDSAMG   300
TNWVPEEASG EASEIPVPQG TELSPSRPGG GSMQTEPARP SNFLSASSPL PASAKGQQPA   360
DVTGTALPRV GPVRPTGQDW NHTPQKTDHP SALLRDPPEP GSPRISSLRP QGLSNPSTLS   420
AQPQLSRSHS SGSVLPLGEL EGRRSTRDRR SPAEPEGGPA SEGAARPLPR FNSVPLTDTG   480
HERQSEGSSS PQLQESVFHL LVPSVILVLL AVGGLLFYRW RRRSHQEPQR ADSPLEQPEG   540
SPLTQDDRQV ELPV                                                     554

SEQ ID NO: 6              moltype = AA   length = 522
FEATURE                   Location/Qualifiers
source                    1..522
                          mol_type = protein
                          organism = Homo sapiens
SEQUENCE: 6
EEVSEYCSHM IGSGHLQSLQ RLIDSQMETS CQITFEFVDQ EQLKDPVCYL KKAFLLVQDI    60
MEDTMRFRDN TPNAIAIVQL QELSLRLKSC FTKDYEEHDK ACVRTFYETP LQLLEKVKNV   120
FNETKNLLDK DWNIFSKNCN NSFAECSSQD VVTKPDCNCL YPKAIPSSDP ASVSPHQPLA   180
PSMAPVAGLT WEDSEGTEGS SLLPGEQPLH TVDPGSAKQR PPRSTCQSFE PPETPVVKDS   240
TIGGSPQPRP SVGAFNPGME DILDSAMGTN WVPEEASGEA SEIPVPQGTE LSPSRPGGGS   300
MQTEPARPSN FLSASSPLPA SAKGQQPADV TGTALPRVGP VRPTGQDWNH TPQKTDHPSA   360
LLRDPPEPGS PRISSLRPQG LSNPSTLSAQ PQLSRSHSSG SVLPLGELEG RRSTRDRRSP   420
AEPEGGPASE GAARPLPRFN SVPLTDTGHE RQSEGSSSPQ LQESVFHLLV PSVILVLLAV   480
GGLLFYRWRR RSHQEPQRAD SPLEQPEGSP LTQDDRQVEL PV                      522

SEQ ID NO: 7              moltype = AA   length = 438
FEATURE                   Location/Qualifiers
source                    1..438
                          mol_type = protein
                          organism = Homo sapiens
SEQUENCE: 7
MTAPGAAGRC PPTTWLGSLL LLVCLLASRS ITEEVSEYCS HMIGSGHLQS LQRLIDSQME    60
TSCQITFEFV DQEQLKDPVC YLKKAFLLVQ DIMEDTMRFR DNTPNAIAIV QLQELSLRLK   120
SCFTKDYEEH DKACVRTFYE TPLQLLEKVK NVFNETKNLL DKDWNIFSKN CNNSFAECSS   180
QDVVTKPDCN CLYPKAIPSS DPASVSPHQP LAPSMAPVAG LTWEDSEGTE GSSLLPGEQP   240
LHTVDPGSAK QRPPRSTCQS FEPPETPVVK DSTIGGSPQP RPSVGAFNPG MEDILDSAMG   300
TNWVPEEASG EASEIPVPQG TELSPSRPGG GSMQTEPARP SNFLSASSPL PASAKGQQPA   360
DVTGHERQSE GSSSPQLQES VFHLLVPSVI LVLLAVGGLL FYRWRRRSHQ EPQRADSPLE   420
QPEGSPLTQD DRQVELPV                                                 438

SEQ ID NO: 8              moltype = AA   length = 406
FEATURE                   Location/Qualifiers
source                    1..406
                          mol_type = protein
                          organism = Homo sapiens
SEQUENCE: 8
EEVSEYCSHM IGSGHLQSLQ RLIDSQMETS CQITFEFVDQ EQLKDPVCYL KKAFLLVQDI    60
MEDTMRFRDN TPNAIAIVQL QELSLRLKSC FTKDYEEHDK ACVRTFYETP LQLLEKVKNV   120
FNETKNLLDK DWNIFSKNCN NSFAECSSQD VVTKPDCNCL YPKAIPSSDP ASVSPHQPLA   180
PSMAPVAGLT WEDSEGTEGS SLLPGEQPLH TVDPGSAKQR PPRSTCQSFE PPETPVVKDS   240
TIGGSPQPRP SVGAFNPGME DILDSAMGTN WVPEEASGEA SEIPVPQGTE LSPSRPGGGS   300
MQTEPARPSN FLSASSPLPA SAKGQQPADV TGHERQSEGS SSPQLQESVF HLLVPSVILV   360
LLAVGGLLFY RWRRRSHQEP QRADSPLEQP EGSPLTQDDR QVELPV                  406
```

```
SEQ ID NO: 9              moltype = AA   length = 256
FEATURE                   Location/Qualifiers
source                    1..256
                          mol_type = protein
                          organism = Homo sapiens
SEQUENCE: 9
MTAPGAAGRC PPTTWLGSLL LLVCLLASRS ITEEVSEYCS HMIGSGHLQS LQRLIDSQME   60
TSCQITFEFV DQEQLKDPVC YLKKAFLLVQ DIMEDTMRFR DNTPNAIAIV QLQELSLRLK  120
SCFTKDYEEH DKACVRTFYE TPLQLLEKVK NVFNETKNLL DKDWNIFSKN CNNSFAECSS  180
QGHERQSEGS SSPQLQESVF HLLVPSVILV LLAVGGLLFY RWRRRSHQEP QRADSPLEQP  240
EGSPLTQDDR QVELPV                                                 256

SEQ ID NO: 10             moltype = AA   length = 224
FEATURE                   Location/Qualifiers
source                    1..224
                          mol_type = protein
                          organism = Homo sapiens
SEQUENCE: 10
EEVSEYCSHM IGSGHLQSLQ RLIDSQMETS CQITFEFVDQ EQLKDPVCYL KKAFLLVQDI   60
MEDTMRFRDN TPNAIAIVQL QELSRLKSC FTKDYEEHDK ACVRTFYETP LQLLEKVKNV  120
FNETKNLLDK DWNIFSKNCN NSFAECSSQG HERQSEGSSS PQLQESVFHL LVPSVILVLL  180
AVGGLLFYRW RRRSHQEPQR ADSPLEQPEG SPLTQDDRQV ELPV                  224

SEQ ID NO: 11             moltype = AA   length = 245
FEATURE                   Location/Qualifiers
source                    1..245
                          mol_type = protein
                          organism = Homo sapiens
SEQUENCE: 11
MKKTQTWILT CIYLQLLLFN PLVKTEGICR NRVTNNVKDV TKLVANLPKD YMITLKYVPG   60
MDVLPSHCWI SEMVVQLSDS LTDLLDKFSN ISEGLSNYSI IDKLVNIVDD LVECVKENSS  120
KDLKKSFKSP EPRLFTPEEF FRIFNRSIDA FKDFVVASET SDCVVSSTLS PEKGKAKNPP  180
GDSSLHWAAM ALPALFSLII GFAFGALYWK KRQPSLTRAV ENIQINEEDN EISMLQEKER  240
EFQEV                                                             245

SEQ ID NO: 12             moltype = DNA   length = 738
FEATURE                   Location/Qualifiers
source                    1..738
                          mol_type = genomic DNA
                          organism = Homo sapiens
SEQUENCE: 12
atgaagaaga cacaaacttg gattctcact tgcatttatc ttcagctgct cctatttaat   60
cctctcgtca aaactgaagg gatctgcagg aatcgtgtga ctaataatgt aaaagacgtc  120
actaaattgg tggcaaatct tccaaaagac tacatgataa ccctcaaata tgtccccggg  180
atggatgttt tgccaagtca ttgttggata agcgagatgg tagtacaatt gtcagacagc  240
ttgactgatc ttctggacaa gttttcaaat atttctgaag gctgagtaa ttattccatc  300
atagacaaac ttgtgaatat agtggatgac cttgtggagt gcgtgaaaga aaactcatct  360
aaggatctaa aaaatcatt caagagccca gaacccaggc tctttactcc tgaagaattc  420
tttagaattt taatagatc cattgatgcc ttcaaggact ttgtagtggc atctgaaact  480
agtgattgtg tggtttcttc aacattaagt cctgagaaag ggaaggccaa aaatcccct  540
ggagactcca gcctacactg ggcagccatg gcattgccag cattgttttc tcttataatt  600
ggctttgctt ttggagcctt atactggaag aagagacagc caagtcttac aagggcagtt  660
gaaaatatac aaattaatga agaggataat gagataagta tgttgcaaga aaagagagaa  720
gagtttcaag aagtgtaa                                               738

SEQ ID NO: 13             moltype = AA   length = 273
FEATURE                   Location/Qualifiers
source                    1..273
                          mol_type = protein
                          organism = Homo sapiens
SEQUENCE: 13
MKKTQTWILT CIYLQLLLFN PLVKTEGICR NRVTNNVKDV TKLVANLPKD YMITLKYVPG   60
MDVLPSHCWI SEMVVQLSDS LTDLLDKFSN ISEGLSNYSI IDKLVNIVDD LVECVKENSS  120
KDLKKSFKSP EPRLFTPEEF FRIFNRSIDA FKDFVVASET SDCVVSSTLS PEKDSRVSVT  180
KPFMLPPVAA SSLRNDSSSS NRKAKNPPGD SSLHWAAMAL PALFSLIIGF AFGALYWKKR  240
QPSLTRAVEN IQINEEDNEI SMLQEKEREF QEV                              273

SEQ ID NO: 14             moltype = DNA   length = 822
FEATURE                   Location/Qualifiers
source                    1..822
                          mol_type = genomic DNA
                          organism = Homo sapiens
SEQUENCE: 14
atgaagaaga cacaaacttg gattctcact tgcatttatc ttcagctgct cctatttaat   60
cctctcgtca aaactgaagg gatctgcagg aatcgtgtga ctaataatgt aaaagacgtc  120
actaaattgg tggcaaatct tccaaaagac tacatgataa ccctcaaata tgtccccggg  180
atggatgttt tgccaagtca ttgttggata agcgagatgg tagtacaatt gtcagacagc  240
ttgactgatc ttctggacaa gttttcaaat atttctgaag gctgagtaa ttattccatc  300
```

```
atagacaaac ttgtgaatat agtggatgac cttgtggagt gcgtgaaaga aaactcatct    360
aaggatctaa aaaatcatt caagagccca gaacccaggc tctttactcc tgaagaattc    420
tttagaattt ttaatagatc cattgatgcc ttcaaggact tgtgtagtgg atctgaaact    480
agtgattgtg tggtttcttc aacattaagt cctgagaaag attccagagt cagtgtcaca    540
aaaccattta tgttacccccc tgttgcagcc agctcccta ggaatgacag cagtagcagt    600
aataggaagg ccaaaaatcc ccctggagac tccagcctac actgggcagc catggcattg    660
ccagcattgt tttctcttat aattggcttt gcttttggag cctatactg gaagaagaga    720
cagccaagtc ttacaagggc agttgaaaat atacaaatta tgaagagga taatgagata    780
agtatgttgc aagagaaaga gagagagttt caagaagtgt aa                      822

SEQ ID NO: 15             moltype = DNA   length = 1405
FEATURE                   Location/Qualifiers
source                    1..1405
                          mol_type = genomic DNA
                          organism = Homo sapiens
SEQUENCE: 15
ccgcctcgcg ccgagactag aagcgctgcg ggaagcaggg acagtggaga gggcgctgcg     60
ctcgggctac ccaatgcgtg gactatctgc cgccgctgtt cgtcgcaatat gctggagctc    120
cagaacagct aaacggagtc gccacaccac tgtttgtgct ggatcgcagc gctgcctttc    180
cttatgaaga agacacaaac ttggattctc acttgcattt atcttcagct gctcctattt    240
aatcctctcg tcaaaactga agggatctgc aggaatcgtg tgactaataa tgtaaaagac    300
gtcactaaat tggtggcaaa tcttccaaaa gactacatga taaccctcaa atatgtcccc    360
gggatggatg ttttgccaag tcattgttgg ataagcgaga tggtagtaca attgtcagac    420
agcttgactg atcttctgga caagttttca aatatttctg aaggcttgag taattattcc    480
atcatagaca aacttgtgaa tatagtggat gaccttgtgg agtgcgtgaa agaaaactca    540
tctaaggatc taaaaaaatc attcaagagc ccagaaccca ggctctttac tcctgaagaa    600
ttctttagaa tttttaatag atccattgat gccttcaagg actttgtagt ggcatctgaa    660
actagtgatt gtgtggtttc ttcaacatta agtcctgaga agattccag agtcagtgtc    720
acaaaaccat ttatgttacc ccctgttgca gccagctccc ttaggaatga cagcagtagc    780
agtaataggaa aggccaaaaa tccccctgga gactccagcc tacactgggc agccatggca    840
ttgccagcat tgttttctct tataattggc tttgctttttg gagccttata ctggaagaag    900
agacagccaa gtcttacaag ggcagttgaa aatatacaaa ttaatgaaga ggataatgag    960
ataagtatgt tgcaagagaa agagagagag tttcaagaag tgtaaattgt ggcttgtatc   1020
aacactgtta ctttcgtaca ttggctggta acagttcgtc tttgcttcat aaatgaagca   1080
gctttaaaca aattcatatt ctgtctggag tgacagacca catctttatc tgttcttgct   1140
acccatgact ttatatggat gattcagaaa ttggaacaga atgttttact gtgaaactgg   1200
cactgaatta atcatctata aagaagaact tgcatggagc aggactctat tttaaggact   1260
gcgggacttg ggtctcattt agaacttgca gctgatgttg aagagaaag cacgtgtctc   1320
agactgcatg taccatttgc atggctccag aaatgtctaa atgctgaaaa aacacctagc   1380
tttattcttc agatacaaac tgcag                                         1405

SEQ ID NO: 16             moltype = AA   length = 189
FEATURE                   Location/Qualifiers
source                    1..189
                          mol_type = protein
                          organism = Homo sapiens
SEQUENCE: 16
MKKTQTWILT CIYLQLLLFN PLVKTEGICR NRVTNNVKDV TKLVANLPKD YMITLKYVPG     60
MDVLPSHCWI SEMVVQLSDS LTDLLDKFSN ISEGLSNYSI IDKLVNIVDD LVECVKENSS    120
KDLKKSFKSP EPRLFTPEEF FRIFNRSIDA FKDFVVASET SDCVVSSTLS PEKDSRVSVT    180
KPFMLPPVA                                                            189

SEQ ID NO: 17             moltype = DNA   length = 567
FEATURE                   Location/Qualifiers
source                    1..567
                          mol_type = genomic DNA
                          organism = Homo sapiens
SEQUENCE: 17
atgaagaaga cacaaacttg gattctcact tgcatttatc ttcagctgct cctatttaat     60
cctctcgtca aaactgaagg gatctgcagg aatcgtgtga ctaataatgt aaaagacgtc    120
actaaattgg tggcaaatct tccaaaagac tacatgataa ccctcaaata tgtccccggg    180
atggatgttt tgccaagtca ttgttggata agcgagatgg tagtacaatt gtcagacagc    240
ttgactgatc ttctggacaa gttttcaaat atttctgaag gcttgagtaa ttattccatc    300
atagacaaac ttgtgaatat agtggatgac cttgtggagt gcgtgaaaga aaactcatct    360
aaggatctaa aaaatcatt caagagccca gaacccaggc tctttactcc tgaagaattc    420
tttagaattt ttaatagatc cattgatgcc ttcaaggact tgtgtagtgg atctgaaact    480
agtgattgtg tggtttcttc aacattaagt cctgagaaag attccagagt cagtgtcaca    540
aaaccattta tgttacccccc tgttgca                                       567

SEQ ID NO: 18             moltype = AA   length = 144
FEATURE                   Location/Qualifiers
source                    1..144
                          mol_type = protein
                          organism = Homo sapiens
SEQUENCE: 18
MWLQSLLLLG TVACSISAPA RSPSPSTQPW EHVNAIQEAR RLLNLSRDTA AEMNETVEVI     60
SEMFDLQEPT CLQTRLELYK QGLRGSLTKL KGPLTMMASH YKQHCPPTPE TSCATQIITF    120
ESFKENLKDF LLVIPFDCWE PVQE                                           144
```

| SEQ ID NO: 19 | moltype = DNA length = 435 |
| --- | --- |
| FEATURE | Location/Qualifiers |
| source | 1..435 |
| | mol_type = genomic DNA |
| | organism = Homo sapiens |

SEQUENCE: 19

```
atgtggctgc agagcctgct gctcttgggc actgtggcct gcagcatctc tgcacccgcc    60
cgctcgccca gccccagcac gcagccctgg gagcatgtga atgccatcca ggaggcccgg   120
cgtctcctga acctgagtag agacactgct gctgagatga tgaaacagt agaagtcatc   180
tcagaaatgt ttgacctcca ggagccgacc tgcctacaga cccgcctgga gctgtacaag   240
cagggcctgc ggggcagcct caccaagctc aaggggcccct tgaccatgat ggccagccac   300
tacaagcagc actgccctcc aaccccggaa acttcctgtg caacccagat tatcaccttt   360
gaaagtttca agagaacctt gaaggacttt ctgcttgtca tccccttga ctgctgggag   420
ccagtccagg agtga                                                    435
```

| SEQ ID NO: 20 | moltype = AA length = 127 |
| --- | --- |
| FEATURE | Location/Qualifiers |
| source | 1..127 |
| | mol_type = protein |
| | organism = Homo sapiens |

SEQUENCE: 20

```
APARSPSPST QPWEHVNAIQ EARRLLNLSR DTAAEMNETV EVISEMFDLQ EPTCLQTRLE    60
LYKQGLRGSL TKLKGPLTMM ASHYKQHCPP TPETSCATQI ITFESFKENL KDFLLVIPFD   120
CWEPVQE                                                             127
```

| SEQ ID NO: 21 | moltype = DNA length = 352 |
| --- | --- |
| FEATURE | Location/Qualifiers |
| source | 1..352 |
| | mol_type = genomic DNA |
| | organism = Homo sapiens |

SEQUENCE: 21

```
gccctgggag catgtgaatg ccatccagga ggcccggcgt ctcctgaacc tgagtagaga    60
cactgctgct gagatgaatg aaacagtaga agtcatctca gaaatgtttg acctccagga   120
gccgacctgc ctacagaccc gcctggagct gtacaagcag ggcctgcggg gcagcctcac   180
caagctcaag ggcccttga ccatgatggc cagccacac aagcagc gccctccaac       240
cccggaaact tcctgtgcaa cccagattat cacctttgaa agtttcaaag agaacctgaa   300
ggactttctg cttgtcatcc cctttgactg ctgggagcca gtccaggagt ga           352
```

| SEQ ID NO: 22 | moltype = AA length = 152 |
| --- | --- |
| FEATURE | Location/Qualifiers |
| source | 1..152 |
| | mol_type = protein |
| | organism = Homo sapiens |

SEQUENCE: 22

```
MSRLPVLLLL QLLVRPGLQA PMTQTTPLKT SWVNCSNMID EIITHLKQPP LPLLDFNNLN    60
GEDQDILMEN NLRRPNLEAF NRAVKSLQNA SAIESILKNL LPCLPLATAA PTRHPIHIKD   120
GDWNEFRRKL TFYLKTLENA QAQQTTLSLA IF                                  152
```

| SEQ ID NO: 23 | moltype = DNA length = 459 |
| --- | --- |
| FEATURE | Location/Qualifiers |
| source | 1..459 |
| | mol_type = genomic DNA |
| | organism = Homo sapiens |

SEQUENCE: 23

```
atgagccgcc tgcccgtcct gctcctgctc caactcctgg tccgcccgg actccaagct    60
cccatgaccc agacaacgcc cttgaagaca agctgggtta actgctctaa catgatcgat   120
gaaattataa cacacttaaa gcagccacct ttgcctttgc tggacttcaa caacctcaat   180
ggggaagacc aagacattct gatggaaaat aaccttcgaa ggccaaacct ggaggcattc   240
aacagggctg tcaagagttt acagaacgca tcagcaattg agagcattct taaaaatctc   300
ctgccatgtc tgccccttgc cacggccgca cccacgcgca atccaatcca tatcaaggac   360
ggtgactgga tgaattccg gaggaaactg acgttctatc tgaaaaccct tgagaatgcg   420
caggctcaac agacgacttt gagcctcgcg atcttttga                          459
```

| SEQ ID NO: 24 | moltype = AA length = 133 |
| --- | --- |
| FEATURE | Location/Qualifiers |
| source | 1..133 |
| | mol_type = protein |
| | organism = Homo sapiens |

SEQUENCE: 24

```
APMTQTTPLK TSWVNCSNMI DEIITHLKQP PLPLLDFNNL NGEDQDILME NNLRRPNLEA    60
FNRAVKSLQN ASAIESILKN LLPCLPLATA APTRHPIHIK DGDWNEFRRK LTFYLKTLEN   120
AQAQQTTLSL AIF                                                      133
```

| SEQ ID NO: 25 | moltype = DNA length = 402 |
| --- | --- |
| FEATURE | Location/Qualifiers |
| source | 1..402 |
| | mol_type = genomic DNA |
| | organism = Homo sapiens |

SEQUENCE: 25

```
gctcccatga cccagacaac gcccttgaag acaagctggg ttaactgctc taacatgatc   60
gatgaaatta taacacactt aaagcagcca cctttgcctt tgctggactt caacaacctc  120
aatggggaag accaagacat tctgatggaa aataaccttc gaaggccaaa cctggaggca  180
ttcaacaggg ctgtcaagag tttacagaac gcatcagcaa ttgagagcat tcttaaaaat  240
ctcctgccat gtctgcccct ggccacggcc gcacccacgc gacatccaat ccatatcaag  300
gacggtgact ggaatgaatt ccggaggaaa ctgacgttct atctgaaaac cctttgagaat 360
gcgcaggctc aacagacgac tttgagcctc gcgatctttt ga                     402
```

METHODS AND MODELS FOR ASSESSING EFFICACY OF IMMUNOTHERAPIES

RELATED APPLICATIONS

This application is a continuation of U.S. application Ser. No. 16/465,006, filed May 29, 2019, which is a national stage filing under 35 U.S.C. § 371 of international application number PCT/US2017/063948, filed Nov. 30, 2017, which was published under PCT Article 21 (2) in English and claims priority to U.S. Provisional Application Ser. No. 62/428,131, filed Nov. 30, 2016 and U.S. Provisional Application Ser. No. 62/565,783, filed Sep. 29, 2017, each of which is herein incorporated by reference in its entirety.

GRANT REFERENCE

This invention was made with government support under Grant Nos. CA034196, OD018259, DK104218, and AI132963, awarded by the National Institutes of Health. The Government has certain rights in the invention.

REFERENCE TO AN ELECTRONIC SEQUENCE LISTING

The contents of the electronic sequence listing (J022770044US03-SEQ-HJD.xml; Size: 36,258 bytes; and Date of Creation: Jun. 24, 2024) is herein incorporated by reference in its entirety.

BACKGROUND OF THE INVENTION

There is a continuing need for new "humanized" mouse models that allow robust engraftment of human hematopoietic stem cells along with human-patient derived tumor xenografts and/or human tumor cell lines to enable in vivo investigation of the interactions between the human immune system and human cancer.

SUMMARY OF THE INVENTION

A method of identifying anti-tumor activity of a test substance according to aspects of the present invention includes providing a genetically-modified, immunodeficient mouse, wherein the genetically-modified, immunodeficient mouse includes (a) a nucleotide sequence encoding human stem cell factor (hSCF); (b) a nucleotide sequence encoding human granulocyte-macrophage colony-stimulating factor (hGM-CSF); (c) a nucleotide sequence encoding human interleukin-3 (hIL-3); and (d) a nucleotide sequence encoding human colony-stimulating factor 1 (hCSF1), wherein each of the nucleotide sequences is operably linked to a promoter, wherein the genetically-modified, immunodeficient mouse expresses hSCF, hGM-CSF, hIL-3, and hCSF1; and wherein the genetically-modified, immunodeficient mouse includes a human hematopoietic stem cell; administering a human tumor cell to the genetically-modified, immunodeficient mouse, wherein the human tumor cell forms a solid or non-solid tumor in the genetically-modified, immunodeficient mouse; administering a test substance to the genetically-modified, immunodeficient mouse; and assaying a response of the solid or non-solid tumor to the test substance, wherein an inhibitory effect of the test substance on the tumor and/or tumor cells identifies the test substance as having anti-tumor activity.

A method of identifying anti-tumor activity of a test substance according to aspects of the present invention includes providing a genetically-modified, immunodeficient mouse, wherein the genetically-modified, immunodeficient mouse includes (a) a nucleotide sequence encoding human stem cell factor (hSCF); (b) a nucleotide sequence encoding human granulocyte-macrophage colony-stimulating factor (hGM-CSF); (c) a nucleotide sequence encoding human interleukin-3 (hIL-3); and (d) a nucleotide sequence encoding human colony-stimulating factor 1 (hCSF1), wherein each of the nucleotide sequences is operably linked to a promoter, wherein the genetically-modified, immunodeficient mouse expresses hSCF, hGM-CSF, hIL-3, and hCSF1, wherein the mouse is a genetically modified NOD.Cg-Prkdc$^{scid}$ Il2rg$^{tm1Wjl}$/SzJ (NSG) mouse; a genetically modified NOD.Cg-Rag1$^{tm1Mom}$ Il2rg$^{tm1Wjl}$/SzJ (NRG) mouse or a genetically modified NOD.Cg-Prkdc$^{scid}$ Il2rg$^{tm1Sug}$/JicTac (NOG) mouse; and wherein the genetically-modified, immunodeficient mouse includes a human hematopoietic stem cell; administering a human tumor cell to the genetically-modified, immunodeficient mouse, wherein the human tumor cell forms a solid or non-solid tumor in the genetically-modified, immunodeficient mouse; administering a test substance to the genetically-modified, immunodeficient mouse; and assaying a response of the solid or non-solid tumor to the test substance, wherein an inhibitory effect of the test substance on the tumor and/or tumor cells identifies the test substance as having anti-tumor activity.

A method of identifying anti-tumor activity of a test substance according to aspects of the present invention includes providing a genetically-modified, immunodeficient mouse, wherein the genetically-modified, immunodeficient mouse includes (a) a nucleotide sequence encoding human stem cell factor (hSCF); (b) a nucleotide sequence encoding human granulocyte-macrophage colony-stimulating factor (hGM-CSF); (c) a nucleotide sequence encoding human interleukin-3 (hIL-3); and (d) a nucleotide sequence encoding human colony-stimulating factor 1 (hCSF1), wherein each of the nucleotide sequences is operably linked to a promoter, wherein the genetically-modified, immunodeficient mouse expresses hSCF, hGM-CSF, hIL-3, and hCSF1; and wherein the genetically-modified, immunodeficient mouse includes a CD34+ human hematopoietic stem cell; administering a human tumor cell to the genetically-modified, immunodeficient mouse, wherein the human tumor cell forms a solid or non-solid tumor in the genetically-modified, immunodeficient mouse; administering a test substance to the genetically-modified, immunodeficient mouse; and assaying a response of the solid or non-solid tumor to the test substance, wherein an inhibitory effect of the test substance on the tumor and/or tumor cells identifies the test substance as having anti-tumor activity.

A method of identifying anti-tumor activity of a test substance according to aspects of the present invention includes providing a genetically-modified, immunodeficient mouse, wherein the genetically-modified, immunodeficient mouse includes (a) a nucleotide sequence encoding human stem cell factor (hSCF); (b) a nucleotide sequence encoding human granulocyte-macrophage colony-stimulating factor (hGM-CSF); (c) a nucleotide sequence encoding human interleukin-3 (hIL-3); and (d) a nucleotide sequence encoding human colony-stimulating factor 1 (hCSF1), wherein each of the nucleotide sequences is operably linked to a promoter, wherein the genetically-modified, immunodeficient mouse expresses hSCF, hGM-CSF, hIL-3, and hCSF1, wherein the mouse is a genetically modified NOD.Cg-Prkdc$^{scid}$ Il2rg$^{tm1Wjl}$/SzJ (NSG) mouse; a genetically modified NOD.Cg-Rag1$^{tm1Mom}$ Il2rg$^{tm1Wjl}$/SzJ (NRG) mouse or a genetically modified NOD.Cg-Prkdc$^{scid}$ Il2rg$^{tm1Sus}$/JicTac (NOG) mouse; and wherein the genetically-modified, immunodeficient mouse includes a CD34+ human hematopoietic stem cell; administering a human tumor cell to the genetically-modified, immunodeficient mouse, wherein the human tumor cell forms a solid or non-solid tumor in the genetically-modified, immunodeficient mouse; administering a test substance to the genetically-modified, immunodeficient mouse; and assaying a response of the solid or non-solid tumor to the test substance, wherein an inhibitory effect of the test substance on the tumor and/or tumor cells identifies the test substance as having anti-tumor activity.

A method of identifying anti-tumor activity of a test substance according to aspects of the present invention includes providing a genetically-modified, immunodeficient mouse, wherein the genetically-modified, immunodeficient mouse includes (a) a nucleotide sequence encoding human stem cell factor (hSCF); (b) a nucleotide sequence encoding human granulocyte-macrophage colony-stimulating factor (hGM-CSF); (c) a nucleotide sequence encoding human interleukin-3 (hIL-3); and (d) a nucleotide sequence encoding human colony-stimulating factor 1 (hCSF1), wherein each of the nucleotide sequences is operably linked to a promoter, wherein the genetically-modified, immunodeficient mouse expresses hSCF, hGM-CSF, hIL-3, and hCSF1; and wherein the genetically-modified, immunodeficient mouse includes a differentiated human hematopoietic stem cell selected from the group consisting of a human myeloid progenitor cell, a human lymphoid progenitor cell, a human CD33+ myeloid cell, a human mast cell, a human monocyte, a human macrophage, human myeloid dendritic cell, a human B cell, a human plasma cell, a human T cell, a human T helper cell, a human cytotoxic T cell, a human Treg cell, a human natural killer cell, and any two or more thereof; administering a human tumor cell to the genetically-modified, immunodeficient mouse, wherein the human tumor cell forms a solid or non-solid tumor in the genetically-modified, immunodeficient mouse; administering a test substance to the genetically-modified, immunodeficient mouse; and assaying a response of the solid or non-solid tumor to the test substance, wherein an inhibitory effect of the test substance on the tumor and/or tumor cells identifies the test substance as having anti-tumor activity.

A method of identifying anti-tumor activity of a test substance according to aspects of the present invention includes providing a genetically-modified, immunodeficient mouse, wherein the genetically-modified, immunodeficient mouse includes (a) a nucleotide sequence encoding human stem cell factor (hSCF); (b) a nucleotide sequence encoding human granulocyte-macrophage colony-stimulating factor (hGM-CSF); (c) a nucleotide sequence encoding human interleukin-3 (hIL-3); and (d) a nucleotide sequence encoding human colony-stimulating factor 1 (hCSF1), wherein each of the nucleotide sequences is operably linked to a promoter, wherein the genetically-modified, immunodeficient mouse expresses hSCF, hGM-CSF, hIL-3, and hCSF1, wherein the mouse is a genetically modified NOD.Cg-Prkdc$^{scid}$ Il2rg$^{tm1Wjl}$/SzJ (NSG) mouse; a genetically modified NOD.Cg-Rag1$^{tm1Mom}$ Il2rg$^{tm1Wjl}$/SzJ (NRG) mouse or a genetically modified NOD.Cg-Prkdc$^{scid}$ Il2rg$^{tm1Sus}$/JicTac (NOG) mouse; and wherein the genetically-modified, immunodeficient mouse includes a differentiated human hematopoietic stem cell selected from the group consisting of a human myeloid progenitor cell, a human lymphoid progenitor cell, a human CD33+ myeloid cell, a human mast cell, a human monocyte, a human macrophage, human myeloid dendritic cell, a human B cell, a human plasma cell, a human T cell, a human T helper cell, a human cytotoxic T cell, a human Treg cell, a human natural killer cell, and any two or more thereof; administering a human tumor cell to the genetically-modified, immunodeficient mouse, wherein the human tumor cell forms a solid or non-solid tumor in the genetically-modified, immunodeficient mouse; administering a test substance to the genetically-modified, immunodeficient mouse; and assaying a response of the solid or non-solid tumor to the test substance, wherein an inhibitory effect of the test substance on the tumor and/or tumor cells identifies the test substance as having anti-tumor activity.

A method of identifying anti-tumor activity of a test substance according to aspects of the present invention includes providing a genetically-modified, immunodeficient mouse, wherein the genetically-modified, immunodeficient mouse includes (a) a nucleotide sequence encoding human stem cell factor (hSCF); (b) a nucleotide sequence encoding human granulocyte-macrophage colony-stimulating factor (hGM-CSF); (c) a nucleotide sequence encoding human interleukin-3 (hIL-3); and (d) a nucleotide sequence encoding human colony-stimulating factor 1 (hCSF1), wherein each of the nucleotide sequences is operably linked to a promoter, wherein the genetically-modified, immunodeficient mouse expresses hSCF, hGM-CSF, hIL-3, and hCSF1; and wherein the genetically-modified, immunodeficient mouse includes a human leukocyte selected from the group consisting of: CD45$^+$ leukocyte, CD20$^+$ leukocyte, CD20$^+$CD45$^+$ leukocyte, CD3$^+$ leukocyte, CD3$^+$CD45$^+$ leukocyte, CD33$^+$ leukocyte, CD33$^+$CD45$^+$ leukocyte, CD14$^+$ leukocyte, CD14$^+$CD45$^+$ leukocyte, CD56$^+$ leukocyte, CD56$^+$CD45$^+$ leukocyte, and any two or more thereof; administering a human tumor cell to the genetically-modified, immunodeficient mouse, wherein the human tumor cell forms a solid or non-solid tumor in the genetically-modified, immunodeficient mouse; administering a test substance to the genetically-modified, immunodeficient mouse; and assaying a response of the solid or non-solid tumor to the test substance, wherein an inhibitory effect of the test substance on the tumor and/or tumor cells identifies the test substance as having anti-tumor activity.

A method of identifying anti-tumor activity of a test substance according to aspects of the present invention includes providing a genetically-modified, immunodeficient mouse, wherein the genetically-modified, immunodeficient mouse includes (a) a nucleotide sequence encoding human stem cell factor (hSCF); (b) a nucleotide sequence encoding human granulocyte-macrophage colony-stimulating factor (hGM-CSF); (c) a nucleotide sequence encoding human interleukin-3 (hIL-3); and (d) a nucleotide sequence encoding human colony-stimulating factor 1 (hCSF1), wherein each of the nucleotide sequences is operably linked to a promoter, wherein the genetically-modified, immunodeficient mouse expresses hSCF, hGM-CSF, hIL-3, and hCSF1, wherein the mouse is a genetically modified NOD.Cg-Prkdc$^{scid}$ Il2rg$^{tm1Wjl}$/SzJ (NSG) mouse; a genetically modified NOD.Cg-Rag1$^{tm1Mom}$ Il2rg$^{tm1Wjl}$/SzJ (NRG) mouse or a genetically modified NOD.Cg-Prkdc$^{scid}$ Il2rg$^{tm1Sug}$/JicTac (NOG) mouse; and wherein the genetically-modified, immunodeficient mouse includes a human leukocyte selected from the group consisting of: CD45$^+$ leukocyte, CD20$^+$ leukocyte, CD20$^+$CD45$^+$ leukocyte, CD3$^+$ leukocyte, CD3$^+$CD45$^+$ leukocyte, CD33$^+$ leukocyte, CD33$^+$CD45$^+$ leukocyte, CD14$^+$ leukocyte, CD14$^+$CD45$^+$ leukocyte, CD56$^+$ leukocyte, CD56$^+$CD45$^+$ leukocyte, and any two or more thereof; administering a human tumor cell to the genetically-modified, immunodeficient mouse, wherein the human tumor cell forms a solid or non-solid tumor in the genetically-modified, immunodeficient mouse; administering a test substance to the genetically-modified, immunodeficient mouse; and assaying a response of the solid or non-solid tumor to the test substance, wherein an inhibitory effect of the test substance on the tumor and/or tumor cells identifies the test substance as having anti-tumor activity.

A method of identifying anti-tumor activity of a test substance according to aspects of the present invention optionally includes comparing the response to a standard to determine the effect of the test substance on the xenogeneic tumor cell, wherein an inhibitory effect of the test substance on the xenogeneic tumor cell identifies the test substance as having anti-tumor activity.

The test substance can be an immunotherapeutic agent, such as an immune checkpoint inhibitor. Immune checkpoint inhibitors include, but are not limited to, a PD-1 inhibitor, PD-L1 inhibitor, or CTLA-4 inhibitor. Immune checkpoint inhibitors include, but are not limited to, atezolizumab, avelumab, durvalumab, ipilimumab, nivolumab, or pembrolizumab, or an antigen-binding fragment of any one of the foregoing. The test substance can be an antibody. The test substance can be an anti-cancer agent.

A genetically-modified, immunodeficient mouse is provided according to aspects of the present invention, wherein the genetically-modified, immunodeficient mouse includes (a) a nucleotide sequence encoding human stem cell factor (hSCF); (b) a nucleotide sequence encoding human granulocyte-macrophage colony-stimulating factor (hGM-CSF); (c) a nucleotide sequence encoding human interleukin-3 (hIL-3); and (d) a nucleotide sequence encoding human colony-stimulating factor 1 (hCSF1), wherein each of the nucleotide sequences is operably linked to a promoter, and wherein the genetically-modified, immunodeficient mouse expresses hSCF, hGM-CSF, hIL-3, and hCSF1.

A genetically-modified, immunodeficient mouse is provided according to aspects of the present invention, wherein the genetically-modified, immunodeficient mouse includes (a) a nucleotide sequence encoding human stem cell factor (hSCF); (b) a nucleotide sequence encoding human granulocyte-macrophage colony-stimulating factor (hGM-CSF); (c) a nucleotide sequence encoding human interleukin-3 (hIL-3); and (d) a nucleotide sequence encoding human colony-stimulating factor 1 (hCSF1), wherein each of the nucleotide sequences is operably linked to a promoter, wherein the genetically-modified, immunodeficient mouse expresses hSCF, hGM-CSF, hIL-3, and hCSF1 and wherein the mouse is a genetically modified NOD.Cg-Prkdc$^{scid}$ Il2rg$^{tm1Wjl}$/SzJ (NSG) mouse; a genetically modified NOD.Cg-Rag1$^{tm1Mom}$ Il2rg$^{tm1Wjl}$/SzJ (NRG) mouse or a genetically modified NOD.Cg-Prkdc$^{scid}$ Il2rg$^{tm1Sug}$/JicTac (NOG) mouse.

A genetically-modified, immunodeficient mouse is provided according to aspects of the present invention, wherein the genetically-modified, immunodeficient mouse includes (a) a nucleotide sequence encoding human stem cell factor (hSCF); (b) a nucleotide sequence encoding human granulocyte-macrophage colony-stimulating factor (hGM-CSF); (c) a nucleotide sequence encoding human interleukin-3 (hIL-3); and (d) a nucleotide sequence encoding human colony-stimulating factor 1 (hCSF1), wherein each of the nucleotide sequences is operably linked to a promoter, wherein the genetically-modified, immunodeficient mouse expresses hSCF, hGM-CSF, hIL-3, and hCSF1; and wherein the genetically-modified, immunodeficient mouse includes a human hematopoietic stem cell.

A genetically-modified, immunodeficient mouse is provided according to aspects of the present invention, wherein the genetically-modified, immunodeficient mouse includes (a) a nucleotide sequence encoding human stem cell factor (hSCF); (b) a nucleotide sequence encoding human granulocyte-macrophage colony-stimulating factor (hGM-CSF); (c) a nucleotide sequence encoding human interleukin-3 (hIL-3); and (d) a nucleotide sequence encoding human colony-stimulating factor 1 (hCSF1), wherein each of the nucleotide sequences is operably linked to a promoter, wherein the genetically-modified, immunodeficient mouse expresses hSCF, hGM-CSF, hIL-3, and hCSF1, wherein the mouse is a genetically modified NOD.Cg-Prkdc$^{scid}$ Il2rg$^{tm1Wjl}$/SzJ (NSG) mouse; a genetically modified NOD.Cg-Rag1$^{tm1Mom}$ Il2rg$^{tm1Wjl}$/SzJ (NRG) mouse or a genetically modified NOD.Cg-Prkdc$^{scid}$ Il2rg$^{tm1Sug}$/JicTac (NOG) mouse; and wherein the genetically-modified, immunodeficient mouse includes a human hematopoietic stem cell.

A genetically-modified, immunodeficient mouse is provided according to aspects of the present invention, wherein the genetically-modified, immunodeficient mouse includes (a) a nucleotide sequence encoding human stem cell factor (hSCF); (b) a nucleotide sequence encoding human granulocyte-macrophage colony-stimulating factor (hGM-CSF); (c) a nucleotide sequence encoding human interleukin-3 (hIL-3); and (d) a nucleotide sequence encoding human colony-stimulating factor 1 (hCSF1), wherein each of the nucleotide sequences is operably linked to a promoter, wherein the genetically-modified, immunodeficient mouse expresses hSCF, hGM-CSF, hIL-3, and hCSF1; and wherein the genetically-modified, immunodeficient mouse includes a CD34$^+$ human hematopoietic stem cell.

A genetically-modified, immunodeficient mouse is provided according to aspects of the present invention, wherein the genetically-modified, immunodeficient mouse includes (a) a nucleotide sequence encoding human stem cell factor (hSCF); (b) a nucleotide sequence encoding human granulocyte-macrophage colony-stimulating factor (hGM-CSF); (c) a nucleotide sequence encoding human interleukin-3 (hIL-3); and (d) a nucleotide sequence encoding human colony-stimulating factor 1 (hCSF1), wherein each of the nucleotide sequences is operably linked to a promoter, wherein the genetically-modified, immunodeficient mouse expresses hSCF, hGM-CSF, hIL-3, and hCSF1, wherein the mouse is a genetically modified NOD.Cg-Prkdc$^{scid}$ Il2rg$^{tm1Wjl}$/SzJ (NSG) mouse; a genetically modified NOD.Cg-Rag1$^{tm1Mom}$ Il2rg$^{tm1Wjl}$/SzJ (NRG) mouse or a genetically modified NOD.Cg-Prkdc$^{scid}$ Il2rg$^{tm1Sug}$/JicTac (NOG) mouse; and wherein the genetically-modified, immunodeficient mouse includes a CD34$^+$ human hematopoietic stem cell.

A genetically-modified, immunodeficient mouse is provided according to aspects of the present invention, wherein the genetically-modified, immunodeficient mouse includes (a) a nucleotide sequence encoding human stem cell factor (hSCF); (b) a nucleotide sequence encoding human granulocyte-macrophage colony-stimulating factor (hGM-CSF); (c) a nucleotide sequence encoding human interleukin-3 (hIL-3); and (d) a nucleotide sequence encoding human colony-stimulating factor 1 (hCSF1), wherein each of the nucleotide sequences is operably linked to a promoter, wherein the genetically-modified, immunodeficient mouse expresses hSCF, hGM-CSF, hIL-3, and hCSF1; and wherein the genetically-modified, immunodeficient mouse includes a differentiated human hematopoietic stem cell selected from the group consisting of a human myeloid progenitor cell, a human lymphoid progenitor cell, a human CD33$^+$ myeloid cell, a human mast cell, a human monocyte, a human macrophage, human myeloid dendritic cell, a human B cell, a human plasma cell, a human T cell, a human T helper cell, a human cytotoxic T cell, a human Treg cell, a human natural killer cell, and any two or more thereof.

A genetically-modified, immunodeficient mouse is provided according to aspects of the present invention, wherein the genetically-modified, immunodeficient mouse includes (a) a nucleotide sequence encoding human stem cell factor (hSCF); (b) a nucleotide sequence encoding human granulocyte-macrophage colony-stimulating factor (hGM-CSF); (c) a nucleotide sequence encoding human interleukin-3 (hIL-3); and (d) a nucleotide sequence encoding human colony-stimulating factor 1 (hCSF1), wherein each of the nucleotide sequences is operably linked to a promoter, wherein the genetically-modified, immunodeficient mouse expresses hSCF, hGM-CSF, hIL-3, and hCSF1, wherein the mouse is a genetically modified NOD.Cg-Prkdc$^{scid}$ Il2rg$^{tm1Wjl}$/SzJ (NSG) mouse; a genetically modified NOD.Cg-Rag1$^{tm1Mom}$ Il2rg$^{tm1Wjl}$/SzJ (NRG) mouse or a genetically modified NOD.Cg-Prkdc$^{scid}$ Il2rg$^{tm1Sug}$/JicTac (NOG) mouse; and wherein the genetically-modified, immunodeficient mouse includes a differentiated human hematopoietic stem cell selected from the group consisting of a human myeloid progenitor cell, a human lymphoid progenitor cell, a human CD33$^+$ myeloid cell, a human mast cell, a human monocyte, a human macrophage, human myeloid dendritic cell, a human B cell, a human plasma cell, a human T cell, a human T helper cell, a human cytotoxic T cell, a human Treg cell, a human natural killer cell, and any two or more thereof.

A genetically-modified, immunodeficient mouse is provided according to aspects of the present invention, wherein the genetically-modified, immunodeficient mouse includes (a) a nucleotide sequence encoding human stem cell factor (hSCF); (b) a nucleotide sequence encoding human granulocyte-macrophage colony-stimulating factor (hGM-CSF); (c) a nucleotide sequence encoding human interleukin-3 (hIL-3); and (d) a nucleotide sequence encoding human colony-stimulating factor 1 (hCSF1), wherein each of the nucleotide sequences is operably linked to a promoter, wherein the genetically-modified, immunodeficient mouse expresses hSCF, hGM-CSF, hIL-3, and hCSF1; and wherein the genetically-modified, immunodeficient mouse includes a human leukocyte selected from the group consisting of: CD45$^+$ leukocyte, CD20$^+$ leukocyte, CD20$^+$CD45$^+$ leukocyte, CD3$^+$ leukocyte, CD3$^+$CD45$^+$ leukocyte, CD33$^+$ leukocyte, CD33$^+$CD45$^+$ leukocyte, CD14$^+$ leukocyte, CD14$^+$CD45$^+$ leukocyte, CD56$^+$ leukocyte, CD56$^+$CD45$^+$ leukocyte, and any two or more thereof.

A genetically-modified, immunodeficient mouse is provided according to aspects of the present invention, wherein the genetically-modified, immunodeficient mouse includes (a) a nucleotide sequence encoding human stem cell factor (hSCF); (b) a nucleotide sequence encoding human granulocyte-macrophage colony-stimulating factor (hGM-CSF); (c) a nucleotide sequence encoding human interleukin-3 (hIL-3); and (d) a nucleotide sequence encoding human colony-stimulating factor 1 (hCSF1), wherein each of the nucleotide sequences is operably linked to a promoter, wherein the genetically-modified, immunodeficient mouse expresses hSCF, hGM-CSF, hIL-3, and hCSF1, wherein the mouse is a genetically modified NOD.Cg-Prkdc$^{scid}$ Il2rg$^{tm1Wjl}$/SzJ (NSG) mouse; a genetically modified NOD.Cg-Rag1$^{tm1Mom}$ Il2rg$^{tm1Wjl}$/SzJ (NRG) mouse or a genetically modified NOD.Cg-Prkdc$^{scid}$ Il2rg$^{tm1Sug}$/JicTac (NOG) mouse; and wherein the genetically-modified, immunodeficient mouse includes a human leukocyte selected from the group consisting of: CD45$^+$ leukocyte, CD20$^+$ leukocyte, CD20$^+$CD45$^+$ leukocyte, CD3$^+$ leukocyte, CD3$^+$CD45$^+$ leukocyte, CD33$^+$ leukocyte, CD33$^+$CD45$^+$ leukocyte, CD14$^+$ leukocyte, CD14$^+$CD45$^+$ leukocyte, CD56$^+$ leukocyte, CD56$^+$CD45$^+$ leukocyte, and any two or more thereof.

A genetically-modified, immunodeficient mouse is provided according to aspects of the present invention, wherein the genetically-modified, immunodeficient mouse includes (a) a nucleotide sequence encoding human stem cell factor (hSCF); (b) a nucleotide sequence encoding human granulocyte-macrophage colony-stimulating factor (hGM-CSF); (c) a nucleotide sequence encoding human interleukin-3 (hIL-3); and (d) a nucleotide sequence encoding human colony-stimulating factor 1 (hCSF1), wherein each of the nucleotide sequences is operably linked to a promoter, wherein the genetically-modified, immunodeficient mouse expresses hSCF, hGM-CSF, hIL-3, and hCSF1, and further comprises a human xenograft comprising a human tumor cell.

A genetically-modified, immunodeficient mouse is provided according to aspects of the present invention, wherein the genetically-modified, immunodeficient mouse includes (a) a nucleotide sequence encoding human stem cell factor (hSCF); (b) a nucleotide sequence encoding human granulocyte-macrophage colony-stimulating factor (hGM-CSF); (c) a nucleotide sequence encoding human interleukin-3 (hIL-3); and (d) a nucleotide sequence encoding human colony-stimulating factor 1 (hCSF1), wherein each of the nucleotide sequences is operably linked to a promoter, wherein the genetically-modified, immunodeficient mouse expresses hSCF, hGM-CSF, hIL-3, and hCSF1 wherein the mouse is a genetically modified NOD.Cg-Prkdc$^{scid}$ Il2rg$^{tm1Wjl}$/SzJ (NSG) mouse; a genetically modified NOD.Cg-Rag1$^{tm1Mom}$ Il2rg$^{tm1Wjl}$/SzJ (NRG) mouse or a genetically modified NOD.Cg-Prkdc$^{scid}$ Il2rg$^{tm1Sug}$/JicTac (NOG) mouse, and further comprises a human xenograft comprising a human tumor cell.

A genetically-modified, immunodeficient mouse is provided according to aspects of the present invention, wherein the genetically-modified, immunodeficient mouse includes (a) a nucleotide sequence encoding human stem cell factor (hSCF); (b) a nucleotide sequence encoding human granulocyte-macrophage colony-stimulating factor (hGM-CSF); (c) a nucleotide sequence encoding human interleukin-3 (hIL-3); and (d) a nucleotide sequence encoding human colony-stimulating factor 1 (hCSF1), wherein each of the nucleotide sequences is operably linked to a promoter, wherein the genetically-modified, immunodeficient mouse expresses hSCF, hGM-CSF, hIL-3, and hCSF1; wherein the genetically-modified, immunodeficient mouse includes a human hematopoietic stem cell, and further comprises a human xenograft comprising a human tumor cell.

A genetically-modified, immunodeficient mouse is provided according to aspects of the present invention, wherein the genetically-modified, immunodeficient mouse includes (a) a nucleotide sequence encoding human stem cell factor (hSCF); (b) a nucleotide sequence encoding human granulocyte-macrophage colony-stimulating factor (hGM-CSF); (c) a nucleotide sequence encoding human interleukin-3 (hIL-3); and (d) a nucleotide sequence encoding human colony-stimulating factor 1 (hCSF1), wherein each of the nucleotide sequences is operably linked to a promoter, wherein the genetically-modified, immunodeficient mouse expresses hSCF, hGM-CSF, hIL-3, and hCSF1, wherein the mouse is a genetically modified NOD.Cg-Prkdc$^{scid}$ Il2rg$^{tm1Wjl}$/SzJ (NSG) mouse; a genetically modified NOD.Cg-Rag1$^{tm1Mom}$ Il2rg$^{tm1Wjl}$/SzJ (NRG) mouse or a genetically modified NOD.Cg-Prkdc$^{scid}$ Il2rg$^{tm1Sug}$/JicTac (NOG) mouse; wherein the genetically-modified, immunodeficient mouse includes a human hematopoietic stem cell, and further comprises a human xenograft comprising a human tumor cell.

A genetically-modified, immunodeficient mouse is provided according to aspects of the present invention, wherein the genetically-modified, immunodeficient mouse includes (a) a nucleotide sequence encoding human stem cell factor (hSCF); (b) a nucleotide sequence encoding human granulocyte-macrophage colony-stimulating factor (hGM-CSF); (c) a nucleotide sequence encoding human interleukin-3 (hIL-3); and (d) a nucleotide sequence encoding human colony-stimulating factor 1 (hCSF1), wherein each of the nucleotide sequences is operably linked to a promoter, wherein the genetically-modified, immunodeficient mouse expresses hSCF, hGM-CSF, hIL-3, and hCSF1; wherein the genetically-modified, immunodeficient mouse includes a CD34$^+$ human hematopoietic stem cell, and further comprises a human xenograft comprising a human tumor cell.

A genetically-modified, immunodeficient mouse is provided according to aspects of the present invention, wherein the genetically-modified, immunodeficient mouse includes (a) a nucleotide sequence encoding human stem cell factor (hSCF); (b) a nucleotide sequence encoding human granulocyte-macrophage colony-stimulating factor (hGM-CSF); (c) a nucleotide sequence encoding human interleukin-3 (hIL-3); and (d) a nucleotide sequence encoding human colony-stimulating factor 1 (hCSF1), wherein each of the nucleotide sequences is operably linked to a promoter, wherein the genetically-modified, immunodeficient mouse expresses hSCF, hGM-CSF, hIL-3, and hCSF1, wherein the mouse is a genetically modified NOD.Cg-Prkdc$^{scid}$ Il2rg$^{tm1Wjl}$/SzJ (NSG) mouse; a genetically modified NOD.Cg-Rag1$^{tm1Mom}$ Il2rg$^{tm1Wjl}$/SzJ (NRG) mouse or a genetically modified NOD.Cg-Prkdc$^{scid}$ Il2rg$^{tm1Sus}$/JicTac (NOG) mouse; wherein the genetically-modified, immunodeficient mouse includes a CD34$^+$ human hematopoietic stem cell, and further comprises a human xenograft comprising a human tumor cell.

A genetically-modified, immunodeficient mouse is provided according to aspects of the present invention, wherein the genetically-modified, immunodeficient mouse includes (a) a nucleotide sequence encoding human stem cell factor (hSCF); (b) a nucleotide sequence encoding human granulocyte-macrophage colony-stimulating factor (hGM-CSF); (c) a nucleotide sequence encoding human interleukin-3 (hIL-3); and (d) a nucleotide sequence encoding human colony-stimulating factor 1 (hCSF1), wherein each of the nucleotide sequences is operably linked to a promoter, wherein the genetically-modified, immunodeficient mouse expresses hSCF, hGM-CSF, hIL-3, and hCSF1; wherein the genetically-modified, immunodeficient mouse includes a differentiated human hematopoietic stem cell selected from the group consisting of: a human myeloid progenitor cell, a human lymphoid progenitor cell, a human CD33$^+$ myeloid cell, a human mast cell, a human monocyte, a human macrophage, human myeloid dendritic cell, a human B cell, a human plasma cell, a human T cell, a human T helper cell, a human cytotoxic T cell, a human Treg cell, a human natural killer cell, and any two or more thereof, and further comprises a human xenograft comprising a human tumor cell.

A genetically-modified, immunodeficient mouse is provided according to aspects of the present invention, wherein the genetically-modified, immunodeficient mouse includes (a) a nucleotide sequence encoding human stem cell factor (hSCF); (b) a nucleotide sequence encoding human granulocyte-macrophage colony-stimulating factor (hGM-CSF); (c) a nucleotide sequence encoding human interleukin-3 (hIL-3); and (d) a nucleotide sequence encoding human colony-stimulating factor 1 (hCSF1), wherein each of the nucleotide sequences is operably linked to a promoter, wherein the genetically-modified, immunodeficient mouse expresses hSCF, hGM-CSF, hIL-3, and hCSF1, wherein the mouse is a genetically modified NOD.Cg-Prkdc$^{scid}$ Il2rg$^{tm1Wjl}$/SzJ (NSG) mouse; a genetically modified NOD.Cg-Rag1$^{tm1Mom}$ Il2rg$^{tm1Wjl}$/SzJ (NRG) mouse or a genetically modified NOD.Cg-Prkdc$^{scid}$ Il2rg$^{tm1Sug}$/JicTac (NOG) mouse; wherein the genetically-modified, immunodeficient mouse includes a differentiated human hematopoietic stem cell selected from the group consisting of: a human myeloid progenitor cell, a human lymphoid progenitor cell, a human CD33$^+$ myeloid cell, a human mast cell, a human monocyte, a human macrophage, human myeloid dendritic cell, a human B cell, a human plasma cell, a human T cell, a human T helper cell, a human cytotoxic T cell, a human Treg cell, a human natural killer cell, and any two or more thereof, and further comprises a human xenograft comprising a human tumor cell.

A genetically-modified, immunodeficient mouse is provided according to aspects of the present invention, wherein the genetically-modified, immunodeficient mouse includes (a) a nucleotide sequence encoding human stem cell factor (hSCF); (b) a nucleotide sequence encoding human granulocyte-macrophage colony-stimulating factor (hGM-CSF); (c) a nucleotide sequence encoding human interleukin-3 (hIL-3); and (d) a nucleotide sequence encoding human colony-stimulating factor 1 (hCSF1), wherein each of the nucleotide sequences is operably linked to a promoter, wherein the genetically-modified, immunodeficient mouse expresses hSCF, hGM-CSF, hIL-3, and hCSF1; wherein the genetically-modified, immunodeficient mouse includes a human leukocyte selected from the group consisting of: CD45$^+$ leukocyte, CD20$^+$ leukocyte, CD20$^+$CD45$^+$ leukocyte, CD3$^+$ leukocyte, CD3$^+$CD45$^+$ leukocyte, CD33$^+$ leukocyte, CD33$^+$CD45$^+$ leukocyte, CD14$^+$ leukocyte, CD14$^+$CD45$^+$ leukocyte, CD56$^+$ leukocyte, CD56$^+$CD45$^+$ leukocyte, and any two or more thereof, and further comprises a human xenograft comprising a human tumor cell.

A genetically-modified, immunodeficient mouse is provided according to aspects of the present invention, wherein the genetically-modified, immunodeficient mouse includes (a) a nucleotide sequence encoding human stem cell factor (hSCF); (b) a nucleotide sequence encoding human granulocyte-macrophage colony-stimulating factor (hGM-CSF); (c) a nucleotide sequence encoding human interleukin-3 (hIL-3); and (d) a nucleotide sequence encoding human colony-stimulating factor 1 (hCSF1), wherein each of the nucleotide sequences is operably linked to a promoter, wherein the genetically-modified, immunodeficient mouse expresses hSCF, hGM-CSF, hIL-3, and hCSF1, wherein the mouse is a genetically modified NOD.Cg-Prkdc$^{scid}$ Il2rg$^{tm1Wjl}$/SzJ (NSG) mouse; a genetically modified NOD.Cg-Rag1$^{tm1Mom}$ Il2rg$^{tm1Wjl}$/SzJ (NRG) mouse or a genetically modified NOD.Cg-Prkdc$^{scid}$ Il2rg$^{tm1Sug}$/JicTac (NOG) mouse; wherein the genetically-modified, immunodeficient mouse includes a human leukocyte selected from the group consisting of: CD45$^+$ leukocyte, CD20$^+$ leukocyte, CD20$^+$CD45$^+$ leukocyte, CD3$^+$ leukocyte, CD3$^+$CD45$^+$ leukocyte, CD33$^+$ leukocyte, CD33$^+$CD45$^+$ leukocyte, CD14$^+$ leukocyte, CD14$^+$CD45$^+$ leukocyte, CD56$^+$ leukocyte, CD56$^+$CD45$^+$ leukocyte, and any two or more thereof, and further comprises a human xenograft comprising a human tumor cell.

According to aspects of the present invention, a genetically-modified, immunodeficient mouse is provided wherein any one or more of the nucleotide sequences encoding hSCF, hGM-CSF, hIL-3, or hCSF1 is operably-linked to a constitutive promoter.

According to aspects of the present invention, a genetically-modified, immunodeficient mouse is provided wherein said mouse comprises, in the absence of an immunological challenge, one, two, three or all of: at least about 20% of the human CD45$^+$ leukocytes of the mouse are CD3$^+$CD45$^+$ leukocytes; at least about 10% of the human CD45$^+$ leukocytes of the mouse are CD33$^+$CD45$^+$ leukocytes; at least about 5% of the human CD45$^+$ leukocytes of the mouse are CD14$^+$CD45$^+$ leukocytes; at least about 0.5% of the human CD45$^+$ leukocytes of the mouse are CD56$^+$CD45$^+$ leukocytes.

According to aspects of the present invention, a genetically-modified, immunodeficient mouse is provided wherein the mouse expresses one or more of: a human cytokine selected from the group consisting of human interleukin-8, human interleukin-1B, human tumor-necrosis factor, human interleukin-12p70, and human interleukin-6.

A method of making a genetically-modified, immunodeficient humanized mouse model according to aspects of the present invention includes providing a genetically-modified, immunodeficient mouse, wherein the genetically-modified, immunodeficient mouse includes (a) a nucleotide sequence encoding human stem cell factor (hSCF); (b) a nucleotide sequence encoding human granulocyte-macrophage colony-stimulating factor (hGM-CSF); (c) a nucleotide sequence encoding human interleukin-3 (hIL-3); and (d) a nucleotide sequence encoding human colony-stimulating factor 1 (hCSF1), wherein each of the nucleotide sequences is operably linked to a promoter, and wherein the genetically-modified, immunodeficient mouse expresses hSCF, hGM-CSF, hIL-3, and hCSF1; and administering human hematopoietic stem cells to the genetically-modified, immunodeficient mouse.

A method of making a genetically-modified, immunodeficient humanized mouse model according to aspects of the present invention includes providing a genetically-modified, immunodeficient mouse, wherein the genetically-modified, immunodeficient mouse includes (a) a nucleotide sequence encoding human stem cell factor (hSCF); (b) a nucleotide sequence encoding human granulocyte-macrophage colony-stimulating factor (hGM-CSF); (c) a nucleotide sequence encoding human interleukin-3 (hIL-3); and (d) a nucleotide sequence encoding human colony-stimulating factor 1 (hCSF1), wherein each of the nucleotide sequences is operably linked to a promoter, wherein the genetically-modified, immunodeficient mouse expresses hSCF, hGM-CSF, hIL-3, and hCSF1 and wherein the mouse is a genetically modified NOD.Cg-Prkdc$^{scid}$ Il2rg$^{tm1Wjl}$/SzJ (NSG) mouse; a genetically modified NOD.Cg-Rag1$^{tm1Mom}$ Il2rg$^{tm1Wjl}$/SzJ (NRG) mouse or a genetically modified NOD.Cg-Prkdc$^{scid}$ Il2rg$^{tm1Sus}$/JicTac (NOG) mouse; and administering human hematopoietic stem cells to the genetically-modified, immunodeficient mouse.

A method of making a genetically-modified, immunodeficient humanized mouse model according to aspects of the present invention includes providing a genetically-modified, immunodeficient mouse, wherein the genetically-modified, immunodeficient mouse includes (a) a nucleotide sequence encoding human stem cell factor (hSCF); (b) a nucleotide sequence encoding human granulocyte-macrophage colony-stimulating factor (hGM-CSF); (c) a nucleotide sequence encoding human interleukin-3 (hIL-3); and (d) a nucleotide sequence encoding human colony-stimulating factor 1 (hCSF1), wherein each of the nucleotide sequences is operably linked to a promoter, and wherein the genetically-modified, immunodeficient mouse expresses hSCF, hGM-CSF, hIL-3, and hCSF1; administering human hematopoietic stem cells to the genetically-modified, immunodeficient mouse; and administering a human xenograft comprising a human tumor cell to the genetically-modified, immunodeficient mouse.

A method of making a genetically-modified, immunodeficient humanized mouse model according to aspects of the present invention includes providing a genetically-modified, immunodeficient mouse, wherein the genetically-modified, immunodeficient mouse includes (a) a nucleotide sequence encoding human stem cell factor (hSCF); (b) a nucleotide sequence encoding human granulocyte-macrophage colony-stimulating factor (hGM-CSF); (c) a nucleotide sequence encoding human interleukin-3 (hIL-3); and (d) a nucleotide sequence encoding human colony-stimulating factor 1 (hCSF1), wherein each of the nucleotide sequences is operably linked to a promoter, wherein the genetically-modified, immunodeficient mouse expresses hSCF, hGM-CSF, hIL-3, and hCSF1 and wherein the mouse is a genetically modified NOD.Cg-Prkdc$^{scid}$ Il2rg$^{tm1Wjl}$/SzJ (NSG) mouse; a genetically modified NOD.Cg-Rag1$^{tm1Mom}$ Il2rg$^{tm1Wjl}$/SzJ (NRG) mouse or a genetically modified NOD.Cg-Prkdc$^{scid}$ Il2rg$^{tm1Sus}$/JicTac (NOG) mouse; administering human hematopoietic stem cells to the genetically-modified, immunodeficient mouse; and administering a human xenograft comprising a human tumor cell to the genetically-modified, immunodeficient mouse.

A method of making a genetically-modified, immunodeficient humanized mouse model according to aspects of the present invention optionally includes conditioning the genetically-modified, immunodeficient mouse to reduce mouse hematopoietic cells of the mouse prior to administering human hematopoietic stem cells. For example, a method of making a genetically-modified, immunodeficient humanized mouse model according to aspects of the present invention optionally includes irradiating the genetically-modified, immunodeficient mouse and/or administering a radiomimetic drug to the genetically-modified, immunodeficient mouse.

A method of making a genetically-modified, immunodeficient humanized mouse model according to aspects of the present invention includes providing a genetically-modified, immunodeficient mouse, wherein the genetically-modified, immunodeficient mouse includes (a) a nucleotide sequence encoding human stem cell factor (hSCF); (b) a nucleotide sequence encoding human granulocyte-macrophage colony-stimulating factor (hGM-CSF); (c) a nucleotide sequence encoding human interleukin-3 (hIL-3); and (d) a nucleotide sequence encoding human colony-stimulating factor 1 (hCSF1), wherein each of the nucleotide sequences is operably linked to a promoter, and wherein the genetically-modified, immunodeficient mouse expresses hSCF, hGM-CSF, hIL-3, and hCSF1; administering human hematopoietic stem cells to the genetically-modified, immunodeficient mouse; and administering a human xenograft comprising a human tumor cell to the genetically-modified, immunodeficient mouse, wherein the human hematopoietic stem cell and the human tumor cell comprise at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, or at least 20 matching HLA alleles.

A method of making a genetically-modified, immunodeficient humanized mouse model according to aspects of the present invention includes providing a genetically-modified, immunodeficient mouse, wherein the genetically-modified, immunodeficient mouse includes (a) a nucleotide sequence encoding human stem cell factor (hSCF); (b) a nucleotide sequence encoding human granulocyte-macrophage colony-stimulating factor (hGM-CSF); (c) a nucleotide sequence encoding human interleukin-3 (hIL-3); and (d) a nucleotide sequence encoding human colony-stimulating factor 1 (hCSF1), wherein each of the nucleotide sequences is operably linked to a promoter, wherein the genetically-modified, immunodeficient mouse expresses hSCF, hGM-CSF, hIL-3, and hCSF1 and wherein the mouse is a genetically modified NOD.Cg-Prkdc$^{scid}$ Il2rg$^{tm1Wjl}$/SzJ (NSG) mouse; a genetically modified NOD.Cg-Rag1$^{tm1Mom}$ Il2rg$^{tm1Wjl}$/SzJ (NRG) mouse or a genetically modified NOD.Cg-Prkdc$^{scid}$ Il2rg$^{tm1Sug}$/JicTac (NOG) mouse; administering human hematopoietic stem cells to the genetically-modified, immunodeficient mouse; and administering a human xenograft comprising a human tumor cell to the genetically-modified, immunodeficient mouse, wherein the human hematopoietic stem cell and the human tumor cell comprise at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, or at least 20 matching HLA alleles.

General aspects of the disclosure related to mouse models of interactions between the human immune system and human cancer. According to specific aspects, a genetically-modified, immunodeficient mouse is provided which expresses hSCF, hGM-CSF, hIL-3, and hCSF1, along with methods of use thereof.

DETAILED DESCRIPTION OF THE INVENTION

Figure 1A:
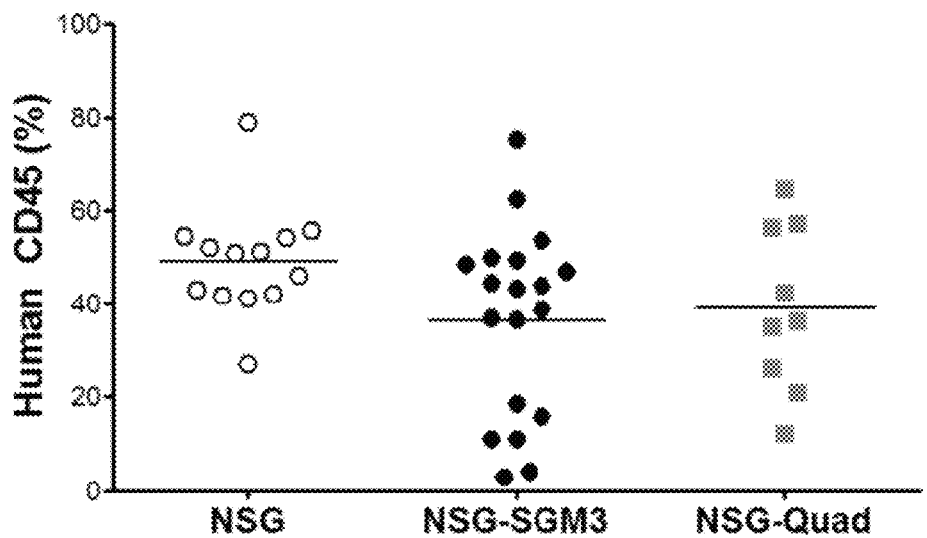
FIG. 1A is a chart depicting percentages of flow-cytometry-gated blood cells expressing human CD45 as a percentage of total blood cells in samples from NSG mice, NSG-SGM3 mice and NSG-QUAD mice 10-weeks after administration of 100,000 human CD34$^+$ hematopoietic stem cells.
Figure 1B:
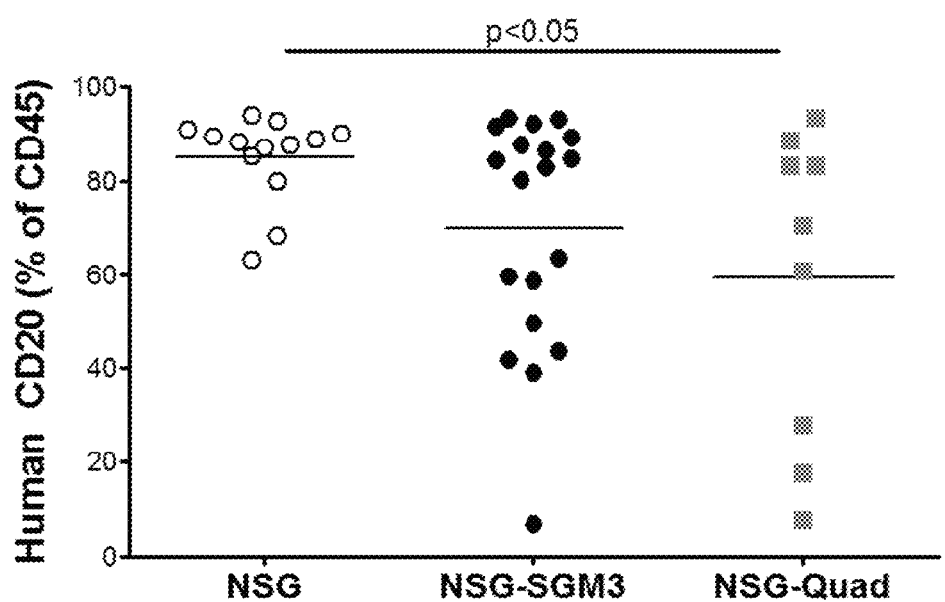
FIG. 1B is a chart depicting percentages of flow-cytometry-gated blood cells expressing human CD20 as a percentage of CD45-positive blood cells in samples from NSG mice, NSG-SGM3 mice and NSG-QUAD mice 10-weeks after administration of 100,000 human CD34$^+$ hematopoietic stem cells.

Scientific and technical terms used herein are intended to have the meanings commonly understood by those of ordinary skill in the art. Such terms are found defined and used in context in various standard references illustratively including J. Sambrook and D. W. Russell, Molecular Cloning: A Laboratory Manual, Cold Spring Harbor Laboratory Press; 3rd Ed., 2001; F. M. Ausubel, Ed., Short Protocols in Molecular Biology, Current Protocols; 5th Ed., 2002; B. Alberts et al., Molecular Biology of the Cell, 4th Ed., Garland, 2002; D. L. Nelson and M. M. Cox, Lehninger Principles of Biochemistry, 4th Ed., W.H. Freeman & Company, 2004; Herdewijn, P. (Ed.), Oligonucleotide Synthesis: Methods and Applications, Methods in Molecular Biology, Humana Press, 2004; A. Nagy, M. Gertsenstein, K. Vintersten, R. Behringer, Manipulating the Mouse Embryo: A Laboratory Manual, 3rd edition, Cold Spring Harbor Laboratory Press; Dec. 15, 2002, ISBN-10:0879695919; and Kursad Turksen (Ed.), Embryonic stem cells: methods and protocols in Methods Mol Biol. 2002; 185, Humana Press; Current Protocols in Stem Cell Biology, ISBN: 9780470151808.

The singular terms "a," "an," and "the" are not intended to be limiting and include plural referents unless explicitly stated otherwise or the context clearly indicates otherwise.

The term "comprising" refers to an open group, e.g., a group comprising members A, B, and C can also include additional members. The term "consisting of" refers to a closed group, e.g., a group consisting of members A, B, and C does not include any additional members.

The term "xenogeneic" is used herein with reference to a host cell or organism to indicate that the material referred to as "xenogeneic" is derived from another species than that of the host cell or organism.

A genetically-modified, immunodeficient mouse which expresses human stem cell factor (hSCF), human granulocyte-macrophage colony-stimulating factor (hGM-CSF), human interleukin-3 (hIL-3), and human colony-stimulating factor 1 (hCSF1) (called an "immunodeficient QUAD mouse" herein) is provided according to aspects of the present invention.

Various aspects of the invention relate to an immunodeficient QUAD mouse including nucleotide sequences encoding hSCF, hGM-CSF, hIL-3, and hCSF1 in its genome wherein the immunodeficient QUAD mouse expresses hSCF, hGM-CSF, hIL-3, and hCSF1 proteins. Nucleic acid sequences are shown and described herein which encode hSCF, hGM-CSF, hIL-3, hCSF1 proteins and variants thereof. It will be appreciated by those of ordinary skill in the art that, due to the degenerate nature of the genetic code, alternate nucleic acid sequences encode hCSF1, hGM-SCF, hSCF, hIL-3 and variants thereof and that such alternate nucleic acids may be used in compositions and methods described herein.

The terms "human colony-stimulating factor 1," "human CSF1," and "hCSF1" are used synonymously herein to refer to a cytokine involved in the proliferation, differentiation, and survival of monocytes, macrophages, and bone marrow progenitor cells. The human CSF1 gene locus resides on chromosome 1, and it occurs as nucleotides 109,910,242-109,930,992 of the Genome Reference Consortium Human Reference 38 genome (GRCh38/hg38). The human CSF1 gene is expressed as at least four transcript variants (see, e.g., NCBI Reference Sequences NM_000757.5, NM_172210.2, NM_172211.3, and NM_172212.2), which produce at least three protein isoforms, a, b, and c (see, e.g., NCBI Reference Sequences NP_000748.3, NP_757349.1, NP_757350.1, and NP_757351.1). The term "hCSF1" includes variants of hCSF1 amino acid sequences specifically identified herein. Human CSF1 proteins are identified herein as SEQ ID NO:5, SEQ ID NO:6, SEQ ID NO:7, SEQ ID NO:8, SEQ ID NO:9, SEQ ID NO: 10, and variants thereof are useful in the present invention.

An immunodeficient QUAD mouse according to aspects of the present invention includes in its genome a nucleic acid encoding hCSF1 operably linked to a promoter wherein the hCSF1 includes the amino acid sequence of SEQ ID NO:5, SEQ ID NO:6, SEQ ID NO:7, SEQ ID NO:8, SEQ ID NO:9, SEQ ID NO: 10, the amino acid sequence encoded by the complement of a nucleic acid which hybridizes to SEQ ID NO: 1 under high stringency hybridization conditions, the amino acid sequence encoded by the complement of a nucleic acid which hybridizes to SEQ ID NO:2 under high stringency hybridization conditions, the amino acid sequence encoded by the complement of a nucleic acid which hybridizes to SEQ ID NO:3 under high stringency hybridization conditions, or the amino acid sequence encoded by the complement of a nucleic acid which hybridizes to SEQ ID NO:4 under high stringency hybridization conditions.

The terms "human stem cell factor," "human SCF," and "hSCF" are used synonymously herein to refer to a well-known cytokine that binds to the c-Kit receptor (CD117). SCF is also known as kit ligand, SF, Kitl, KL-1 and other names. Various isoforms of SCF are known including transmembrane and soluble isoforms generated by alternative splicing. Particular isoforms include human membrane-associated stem cell factor 248 ($SCF^{248}$), human membrane-associated stem cell factor 220 ($SCF^{220}$) and soluble stem cell factor (SCF), see Anderson, D. M. et al., 1990, Cell 63, 235; Flannagan, J. G. et al., 1991, Cell 64, 1025; Anderson, D. M. et al., 1991, Cell Growth Differ. 2, 373; Martin, F. H. et al., Cell, 63:203, 1990; Huang E. J. et al., Mol. Biol. Cell, 3:349, 1992; and Huang E. et al., Cell, 63:225, 1990. Amino acid sequences of human soluble SCF, human $SCF^{220}$ and human $SCF^{248}$ along with exemplary nucleic acid sequences encoding human soluble SCF, human $SCF^{220}$ or human $SCF^{248}$ are shown herein. The term "hSCF" includes variants of hSCF amino acid sequences specifically identified herein. Human SCF proteins are identified herein as SEQ ID NO:11, SEQ ID NO:13, and SEQ ID NO: 16, and variants thereof are useful in the present invention.

An immunodeficient QUAD mouse according to aspects of the present invention includes in its genome a nucleic acid encoding hSCF operably linked to a promoter wherein the hSCF includes the amino acid sequence of SEQ ID NO:11, SEQ ID NO:13, SEQ ID NO:16, the amino acid sequence encoded by the complement of a nucleic acid which hybridizes to SEQ ID NO: 12 under high stringency hybridization conditions, the amino acid sequence encoded by the complement of a nucleic acid which hybridizes to SEQ ID NO: 14 under high stringency hybridization conditions, the amino acid sequence encoded by the complement of a nucleic acid which hybridizes to SEQ ID NO:15 under high stringency hybridization conditions, or the amino acid sequence encoded by the complement of a nucleic acid which hybridizes to SEQ ID NO: 17 under high stringency hybridization conditions.

The terms "human granulocyte-macrophage colony-stimulating factor," "human GM-CSF," and "hGM-CSF" are used synonymously herein. Human GM-CSF is a well-known cytokine that controls the production, differentiation, and function of granulocytes and macrophages. The term "GM-CSF" includes variants of GM-CSF amino acid sequences specifically identified herein. Human GM-CSF proteins are identified herein as SEQ ID NO:18, and SEQ ID NO:20 and variants thereof in the present invention.

An immunodeficient QUAD mouse according to aspects of the present invention includes in its genome a nucleic acid encoding hGM-CSF operably linked to a promoter wherein the hGM-CSF includes the amino acid sequence of SEQ ID NO:18, SEQ ID NO: 20, the amino acid sequence encoded by the complement of a nucleic acid which hybridizes to SEQ ID NO:19 under high stringency hybridization conditions, or the amino acid sequence encoded by the complement of a nucleic acid which hybridizes to SEQ ID NO:21 under high stringency hybridization conditions.

The terms "human interleukin-3," "human IL-3," and "hIL-3" are used synonymously herein. IL-3 is a well-known cytokine that regulates blood-cell production by controlling the production, differentiation and function of granulocytes and macrophages. The term "hIL-3" includes variants of hIL-3 amino acid sequences specifically identified herein. Human IL-3 proteins are identified herein as SEQ ID NO: 22, and SEQ ID NO: 24 and variants thereof in the present invention.

An immunodeficient QUAD mouse according to aspects of the present invention includes in its genome a nucleic acid encoding hIL-3 operably linked to a promoter wherein the hIL-3 includes the amino acid sequence of SEQ ID NO:22, SEQ ID NO:24, the amino acid sequence encoded by the complement of a nucleic acid which hybridizes to SEQ ID NO:23 under high stringency hybridization conditions, or the amino acid sequence encoded by the complement of a nucleic acid which hybridizes to SEQ ID NO: 25 under high stringency hybridization conditions.

Aspects of the present invention relate to an immunodeficient QUAD mouse whose genome includes a nucleotide sequence encoding hCSF1, a nucleotide sequence encoding hSCF, a nucleotide sequence encoding hGM-CSF, and a nucleotide sequence encoding hIL-3, wherein the immunodeficient QUAD mouse expresses hCSF1, hSCF, hGM-CSF, and hIL-3.

According to aspects of the present invention, the included nucleotide sequence encoding hCSF1 has a nucleotide sequence that has at least about 85%, 90%, 91%, 92%, 93%, 94%, 95%, 96%, 97%, 98%, 99%, 99.5%, 99.7%, 99.8% or greater sequence identity with the nucleotide sequence set forth in SEQ ID NO:1, SEQ ID NO:2, SEQ ID NO: 3, or SEQ ID NO:4 and encodes hCSF1 having an amino acid sequence that has at least about 85%, 90%, 91%, 92%, 93%, 94%, 95%, 96%, 97%, 98%, 99%, 99.5%, 99.7%, 99.8% or greater sequence identity with the amino acid sequence set forth in SEQ ID NO: 5, SEQ ID NO:6, SEQ ID NO:7, SEQ ID NO:8, SEQ ID NO:9, or SEQ ID NO: 10.

According to aspects of the present invention, the included nucleotide sequence encoding hCSF1 encodes an mRNA transcript having at least about 85%, 90%, 91%, 92%, 93%, 94%, 95%, 96%, 97%, 98%, 99%, 99.5%, 99.7%, 99.8% or greater sequence identity with the nucleotide sequence set forth in SEQ ID NO:1, SEQ ID NO:2, SEQ ID NO: 3, or SEQ ID NO:4 wherein the deoxythymidine bases of the foregoing sequences are substituted with uridine and wherein the mRNA encodes hCSF1 having an amino acid sequence that has at least about 85%, 90%, 91%, 92%, 93%, 94%, 95%, 96%, 97%, 98%, 99%, 99.5%, 99.7%, 99.8% or greater sequence identity with the amino acid sequence set forth in SEQ ID NO:5, SEQ ID NO:6, SEQ ID NO:7, SEQ ID NO:8, SEQ ID NO: 9, or SEQ ID NO:10.

According to aspects of the present invention, the included nucleotide sequence encoding hSCF has a nucleotide sequence that has at least about 85%, 90%, 91%, 92%, 93%, 94%, 95%, 96%, 97%, 98%, 99%, 99.5%, 99.7%, 99.8% or greater sequence identity with the nucleotide sequence set forth in SEQ ID NO: 12, SEQ ID NO:14, SEQ ID NO: 15, or SEQ ID NO:17 and encodes hSCF having an amino acid sequence that has at least about 85%, 90%, 91%, 92%, 93%, 94%, 95%, 96%, 97%, 98%, 99%, 99.5%, 99.7%, 99.8% or greater sequence identity with the amino acid sequence set forth in SEQ ID NO: 11, SEQ ID NO:13, or SEQ ID NO:16.

According to aspects of the present invention, the included nucleotide sequence encoding hSCF encodes an mRNA transcript having at least about 85%, 90%, 91%, 92%, 93%, 94%, 95%, 96%, 97%, 98%, 99%, 99.5%, 99.7%, 99.8% or greater sequence identity with the nucleotide sequence set forth in SEQ ID NO: 12, SEQ ID NO:14, SEQ ID NO: 15, or SEQ ID NO:17 wherein the deoxythymidine bases of the foregoing sequences are substituted with uridine and wherein the mRNA encodes hSCF having an amino acid sequence that has at least about 85%, 90%, 91%, 92%, 93%, 94%, 95%, 96%, 97%, 98%, 99%, 99.5%, 99.7%, 99.8% or greater sequence identity with the amino acid sequence set forth in SEQ ID NO: 11, SEQ ID NO:13, or SEQ ID NO: 16.

According to aspects of the present invention, the included nucleotide sequence encoding hGM-CSF has a nucleotide sequence that has at least about 85%, 90%, 91%, 92%, 93%, 94%, 95%, 96%, 97%, 98%, 99%, 99.5%, 99.7%, 99.8% or greater sequence identity with the nucleotide sequence set forth in SEQ ID NO: 19, or SEQ ID NO:21 and encodes hGM-CSF having an amino acid sequence that has at least about 85%, 90%, 91%, 92%, 93%, 94%, 95%, 96%, 97%, 98%, 99%, 99.5%, 99.7%, 99.8% or greater sequence identity with the amino acid sequence set forth in SEQ ID NO:18, or SEQ ID NO: 20.

According to aspects of the present invention, the included nucleotide sequence encoding hGM-CSF encodes an mRNA transcript having at least about 85%, 90%, 91%, 92%, 93%, 94%, 95%, 96%, 97%, 98%, 99%, 99.5%, 99.7%, 99.8% or greater sequence identity with the nucleotide sequence set forth in SEQ ID NO:19, or SEQ ID NO:21 wherein the deoxythymidine bases of the foregoing sequences are substituted with uridine and wherein the mRNA encodes hGM-CSF having an amino acid sequence that has at least about 85%, 90%, 91%, 92%, 93%, 94%, 95%, 96%, 97%, 98%, 99%, 99.5%, 99.7%, 99.8% or greater sequence identity with the amino acid sequence set forth in SEQ ID NO: 18, or SEQ ID NO:20.

According to aspects of the present invention, the included nucleotide sequence encoding hIL-3 has a nucleotide sequence that has at least about 85%, 90%, 91%, 92%, 93%, 94%, 95%, 96%, 97%, 98%, 99%, 99.5%, 99.7%, 99.8% or greater sequence identity with the nucleotide sequence set forth in SEQ ID NO:23, or SEQ ID NO:25 and encodes hIL-3 having an amino acid sequence that has at least about 85%, 90%, 91%, 92%, 93%, 94%, 95%, 96%, 97%, 98%, 99%, 99.5%, 99.7%, 99.8% or greater sequence identity with the amino acid sequence set forth in SEQ ID NO:22, or SEQ ID NO:24.

According to aspects of the present invention, the included nucleotide sequence encoding hIL-3 encodes an mRNA transcript having at least about 85%, 90%, 91%, 92%, 93%, 94%, 95%, 96%, 97%, 98%, 99%, 99.5%, 99.7%, 99.8% or greater sequence identity with the nucleotide sequence set forth in SEQ ID NO:23, or SEQ ID NO:25 wherein the deoxythymidine bases of the foregoing sequences are substituted with uridine and wherein the mRNA encodes hIL-3 having an amino acid sequence that has at least about 85%, 90%, 91%, 92%, 93%, 94%, 95%, 96%, 97%, 98%, 99%, 99.5%, 99.7%, 99.8% or greater sequence identity with the amino acid sequence set forth in SEQ ID NO: 22, or SEQ ID NO:24.

To determine the percent identity of two amino acid sequences or two nucleotide sequences, the sequences are aligned for optimal comparison purposes (e.g., gaps can be introduced in a first amino acid or nucleotide sequence for optimal alignment with a second amino acid or nucleotide sequence using the default parameters of an alignment software program). The amino acids or nucleotides at corresponding amino acid positions or nucleotide positions are then compared. When a position in the first sequence is occupied by the same amino acid or nucleotide as the corresponding position in the second sequence, then the molecules are identical at that position. The percent identity between the two sequences is a function of the number of identical positions shared by the sequences (i.e., % identity=number of identical aligned positions÷total number of aligned positions×100%). In some embodiments, the two sequences have the same length.

The determination of percent identity between two sequences can be accomplished using a mathematical algorithm. A non-limiting example of a mathematical algorithm utilized for the comparison of two sequences is the algorithm of Karlin and Altschul, 1990, PNAS USA 87:2264-68, modified as in Karlin and Altschul, 1993, PNAS USA 90:5873-77. Such an algorithm is incorporated into the NBLAST and XBLAST programs of Altschul et al, 1990, J. Mol. Biol. 215:403. BLAST nucleotide searches can optionally be performed with the NBLAST nucleotide program parameter set, e.g., for score=100, wordlength=12 to obtain nucleotide sequences homologous to a nucleic acid molecules of the present invention. BLAST protein searches can optionally be performed with the XBLAST program parameter set, e.g., to score 50, wordlength=3 to obtain amino acid sequences homologous to a protein molecule of the present invention. To obtain gapped alignments for comparison purposes, Gapped BLAST can be utilized as described in Altschul et al, 1997, Nucleic Acids Res. 25:3389-02. Alternatively, PSI BLAST can be used to perform an iterated search that detects distant relationships between molecules (id.). When utilizing BLAST, Gapped BLAST, and PSI Blast, the default parameters of the respective programs (e.g., of XBLAST and NBLAST) are used (see, e.g., the NCBI website). Another preferred, non-limiting example of a mathematical algorithm utilized to compare sequences is the algorithm of Myers and Miller, 1988, CABIOS 4:11-17. Such an algorithm is incorporated in the ALIGN program (version 2.0) which is part of the GCG sequence alignment software package. When utilizing the ALIGN program for comparing amino acid sequences, a PAM120 weight residue table, a gap length penalty of 12, and a gap penalty of 4 is used. The Clustal suite of software programs provides an additional method for aligning sequences to determine percent sequence identity.

The percent identity between two sequences is determined using techniques similar to those described above with or without allowing gaps. In calculating percent identity, only exact matches are typically counted.

The terms "hybridization" and "hybridizes" refer to pairing and binding of complementary nucleic acids. Hybridization occurs to varying extents between two nucleic acids depending on factors such as the degree of complementarity of the nucleic acids, the melting temperature, Tm, of the nucleic acids and the stringency of hybridization conditions, as is well known in the art. The term "stringency of hybridization conditions" refers to conditions of temperature, ionic strength, and composition of a hybridization medium with respect to particular common additives such as formamide and Denhardt's solution. Determination of particular hybridization conditions relating to a specified nucleic acid is routine and is well known in the art, for instance, as described in J. Sambrook and D. W. Russell, Molecular Cloning: A Laboratory Manual, Cold Spring Harbor Laboratory Press; 3rd Ed., 2001; and F. M. Ausubel, Ed., Short Protocols in Molecular Biology, Current Protocols; 5th Ed., 2002. High stringency hybridization conditions are those which only allow hybridization of substantially complementary nucleic acids. Typically, nucleic acids having about 85-100% complementarity are considered highly complementary and hybridize under high stringency conditions. Intermediate stringency conditions are exemplified by conditions under which nucleic acids having intermediate complementarity, about 50-84% complementarity, as well as those having a high degree of complementarity, hybridize. In contrast, low stringency hybridization conditions are those in which nucleic acids having a low degree of complementarity hybridize.

The terms "specific hybridization" and "specifically hybridizes" refer to hybridization of a particular nucleic acid to a target nucleic acid without substantial hybridization to nucleic acids other than the target nucleic acid in a sample.

Stringency of hybridization and washing conditions depends on several factors, including the Tm of the probe and target and ionic strength of the hybridization and wash conditions, as is well-known to the skilled artisan. Hybridization and conditions to achieve a desired hybridization stringency are described, for example, in Sambrook et al., Molecular Cloning: A Laboratory Manual, Cold Spring Harbor Laboratory Press, 2001; and Ausubel, F. et al., (Eds.), Short Protocols in Molecular Biology, Wiley, 2002.

Mutations can be introduced using standard molecular biology techniques, such as site-directed mutagenesis and PCR-mediated mutagenesis. One of skill in the art will recognize that one or more amino acid mutations can be introduced without altering the functional properties of the hSCF, hGM-CSF, hIL-3, or hCSF1 proteins.

Conservative amino acid substitutions can be made in the hSCF, hGM-CSF, hIL-3, or hCSF1 proteins to produce hSCF, hGM-CSF, hIL-3, or hCSF1 protein variants. Conservative amino acid substitutions are art recognized substitutions of one amino acid for another amino acid having similar characteristics. For example, each amino acid can be described as having one or more of the following characteristics: electropositive, electronegative, aliphatic, aromatic, polar, hydrophobic, and hydrophilic. A conservative substitution is a substitution of one amino acid having a specified structural or functional characteristic for another amino acid having the same characteristic. Acidic amino acids include aspartate, glutamate; basic amino acids include histidine, lysine, arginine; aliphatic amino acids include isoleucine, leucine, and valine; aromatic amino acids include phenylalanine, tyrosine, and tryptophan; polar amino acids include aspartate, glutamate, histidine, lysine, asparagine, glutamine, arginine, serine, threonine, and tyrosine; and hydrophobic amino acids include alanine, cysteine, phenylalanine, glycine, isoleucine, leucine, methionine, proline, valine, and tryptophan; and conservative substitutions include substitutions among amino acids within each group. Amino acids can also be described in terms of sterics or relative size, alanine, cysteine, aspartate, glycine, asparagine, proline, threonine, serine, and valine are all typically considered to be small.

The term "nucleic acid" refers to RNA or DNA molecules having more than one nucleotide in any form including single-stranded, double-stranded, oligonucleotide, or polynucleotide. The term "nucleotide sequence" refers to the ordering of nucleotides in a nucleic acid.

Nucleic acids encoding hSCF, hGM-CSF, hIL-3, hCSF1, and variants thereof can be isolated or generated recombinantly or synthetically using well-known methodology.

A nucleotide sequence encoding hSCF, hGM-CSF, hIL-3, or hCSF1 can be operably-linked to a promoter. The promoter can be a constitutive promoter. The promoter can be capable of driving gene expression in a host mouse (e.g., an immunodeficient mouse). For example, the promoter can be the CAG promoter. The CAG promoter includes the cytomegalovirus early enhancer element ("C"), the first exon and the first intron of the chicken beta-actin gene ("A"), and the splice acceptor of the rabbit beta-globulin gene ("G"). The CAG promoter is well known and displays robust expression in mouse cells (see, e.g., Jun-ichi et al, 1989, Gene, 79 (2): 269). The CAG promoter can be modified, for example, to remove exons. Other promoters are known to drive robust gene expression in mice including the cytomegalovirus (CMV) immediate-early promoter and the simian virus 40 (SV40) early promoter. Methods for designing genes and positioning promoters in expression constructs are known (see, e.g., Haruyama et al, 2009, Curr. Protoc. Cell Biol., 19.10).

An immunodeficient QUAD mouse can includes nucleic acids encoding hSCF, hGM-CSF, hIL-3, and hCSF1, and each nucleic acid can be operably-linked to a constitutive promoter.

Immunodeficient mice are provided according to embodiments of the present invention whose genomes include an expression cassette including a nucleotide sequence encoding xenogeneic CSF1, wherein the nucleotide sequence is operably-linked to a promoter and a polyadenylation signal, and the mouse expresses the encoded xenogeneic CSF1.

The terms "expression construct" and "expression cassette" are used herein to refer to a double-stranded recombinant nucleotide sequence containing a desired coding sequence and containing one or more regulatory elements necessary or desirable for the expression of the operably-linked coding sequence. The term "regulatory element" as used herein refers to a nucleotide sequence that controls some aspect of the expression of nucleotide sequences. Exemplary regulatory elements illustratively include an enhancer, an internal ribosome entry site (IRES), an intron, an origin of replication, a polyadenylation signal (pA), a promoter, a transcription termination sequence, and an upstream regulatory domain, which contribute to the replication, transcription, and post-transcriptional processing of a nucleotide sequence. Those of ordinary skill in the art are capable of selecting and using these and other regulatory elements in an expression construct with no more than routine experimentation. Expression constructs can be generated recombinantly or synthetically using well-known methodology.

The term "operably-linked" as used herein refers to a nucleotide sequence in a functional relationship with a second nucleotide sequence.

A regulatory element included in an expression cassette can be a promoter. The term "promoter" as used herein refers to a regulatory nucleotide sequence operably-linked to a coding nucleotide sequence to be transcribed such as a nucleotide sequence encoding a desired amino acid. A promoter is generally positioned upstream of a nucleotide sequence to be transcribed and provides a site for specific-binding by RNA polymerase and other transcription factors. A promoter can be a constitutive promoter or an inducible promoter. A promoter can optionally provide ubiquitous, tissue-specific, or cell-type specific expression.

Ubiquitous promoters that can be included in an expression construct include, but are not limited to, a 3-phosphoglycerate kinase (PGK-1) promoter, a beta-actin promoter, a ROSA26 promoter, a heat shock protein 70 (Hsp70) promoter, an EF-1 alpha gene encoding elongation factor 1 alpha (EF-1) promoter, an eukaryotic initiation factor 4A (eIF-4A1) promoter, a chloramphenicol acetyltransferase (CAT) promoter, and a cytomegalovirus (CMV) promoter.

Tissue-specific promoters that can be included in an expression construct include, but are not limited to, a promoter of a gene expressed in the hematopoietic system, such as an hSCF promoter, an hCSF1 promoter, a hIL-3 promoter, a hGM-CSF, an IFN-β promoter, a Wiskott-Aldrich syndrome protein (WASP) promoter, a CD45 (also called leukocyte common antigen) promoter, a Flt-1 (fms-like tyrosine kinase, VEGF Receptor 1) promoter, an endoglin (CD105) promoter, and an ICAM-2 (Intracellular Adhesion Molecule 2) promoter.

These and other promoters are known in the art as exemplified in Abboud et al, 2003, J. Histochem & Cytochem., 51 (7): 941-49; Schorpp et al, 1996, Nucl. Acids Res., 24 (9): 1787-88; McBurney et al, 1994, Devel. Dynamics, 200:278-93; and Majumder et al, 1996, Blood, 87 (8): 3203-11.

In addition to a promoter, one or more enhancer sequences can be included such as, but not limited to, the cytomegalovirus (CMV) early enhancer element and the SV40 enhancer element.

Additional included sequences include an intron sequence such as the beta globin intron or a generic intron, a transcription termination sequence, and an mRNA polyadenylation (pA) sequence such as, but not limited to SV40-pA, beta-globin-pA, hIL-3-pA, hGM-CSF-pA, hSCF-pA, and hCSF1-pA.

An expression construct can optionally include sequences necessary for amplification in bacterial cells, such as a selection marker (e.g., kanamycin or ampicillin resistance gene) and an origin of replication.

For methods of DNA injection of an expression construct into a mouse preimplantation embryo, the expression construct can be linearized before injection into the embryo. Preferably, the expression construct is injected into fertilized oocytes. Fertilized oocytes are collected from superovulated females the day after mating (0.5 days post coitum) and injected with the expression construct. The injected oocytes are either cultured overnight or transferred directly into oviducts of 0.5-day post coitum pseudopregnant females. Methods for superovulation, harvesting of oocytes, expression construct injection, and embryo transfer are known in the art and described, for example, in Manipulating the Mouse Embryo: A Laboratory Manual, 3rd edition, Cold Spring Harbor Laboratory Press; Dec. 15, 2002, ISBN-10: 0879695919. Offspring can be tested for the presence of the expression construct, or relevant portion thereof, by DNA analysis, such as by PCR, Southern blot, or nucleic acid sequencing. Mice that carry the expression construct, or relevant portion thereof, can be tested for protein expression such as by ELISA or Western blot analysis.

The xenogeneic nucleotide sequences encoding hSCF, hGM-CSF, hIL-3, and hCSF1 can be integrated into the genome of some or all of the cells of the mouse. For example, the xenogeneic nucleotide sequences are integrated into the genomes of germline cells of the mouse according to aspects of the present invention thereby enabling the inheritance of the genes to progeny of the mouse.

Alternatively, an expression construct can be transfected into stem cells (embryonic stem cells or induced pluripotent stem cells) using well-known methods, such as electroporation, calcium-phosphate precipitation, or lipofection. The cells are screened for integration of the expression construct, or relevant portion thereof, by DNA analysis, such as PCR, Southern blot, or nucleic acid sequencing. Cells with the correct integration can be tested for functional expression by protein analysis for hSCF, hGM-CSF, hIL-3, and/or hCSF1 using, for example, ELISA or Western blot analysis.

Embryonic stem cells are grown in media optimized for the particular cell line. Typically, embryonic stem cell media contains 15% fetal bovine serum (FBS) or synthetic or semi-synthetic equivalents, 2 mM glutamine, 1 mM sodium pyruvate, 0.1 mM non-essential amino acids, 50 U/mL penicillin and streptomycin, 0.1 mM 2-mercaptocthanol, and 1000 U/mL LIF (plus, for some cell lines chemical inhibitors of differentiation) in Dulbecco's Modified Eagle Media (DMEM). A detailed description is known in the art (Tremml et al, 2008, Current Protocols in Stem Cell Biology, Chapter 1: Unit 1C.4). For a review of inhibitors of embryonic stem cell differentiation, see Buchr et al, 2003, Genesis of embryonic stem cells, Philosophical Transactions of the Royal Society B: Biological Sciences 358:1397-1402.

Selected cells incorporating the expression construct can be injected into preimplantation embryos. For microinjection, embryonic stem cells or induced pluripotent stem cells are rendered to single cells using a mixture of trypsin and EDTA, followed by resuspension in embryonic stem cell media. Groups of single cells are selected using a finely drawn-out glass needle (20-25 micrometer inside diameter) and introduced through the embryo's zona pellucida and into the blastocysts cavity (blastocoel) using an inverted microscope fitted with micromanipulators. Stem cells can also be injected into early stage embryos (e.g., 2-cell, 4-cell, 8-cell, premorula, or morula). Injection can be assisted with a laser or piezo-pulsed drilled opening in the zona pellucida. Approximately 9-10 selected stem cells (embryonic stem cells or induced pluripotent stem cells) are injected per blastocyst, or 8-cell stage embryo, 6-9 stem cells per 4-cell stage embryo, and about 6 stem cells per 2-cell stage embryo. Following stem cell introduction, embryos are allowed to recover for a few hours at 37° C. in 5% $CO_2$, 5% $O_2$ in nitrogen or cultured overnight before transfer into pseudopregnant recipient females. In a further alternative to stem cell injection, stem cells can be aggregated with morula stage embryos. All of these methods are well established and can be used to produce stem cell chimeras. For a more detailed description, see, e.g., Manipulating the Mouse Embryo: A Laboratory Manual, $3^{rd}$ edition (Nagy, Gertsenstein, Vintersten, and Behringer, Cold Spring Harbor Laboratory Press, Dec. 15, 2002, ISBN-10:0879695919; see also Nagy et al, 1990, Development 110:815-821; Kraus et al, 2010, Genesis 48:394-399; and U.S. Pat. Nos. 7,576,259, 7,659,442, and 7,294,754).

Pseudopregnant embryo recipients are prepared using methods known in the art. Briefly, fertile female animals between 6-8 weeks of age are mated with vasectomized or sterile males to induce a hormonal state conductive to supporting surgically introduced embryos. At 2.5 days post coitum (dpc) up to 15 of the stem cell containing blastocysts are introduced into the uterine horn very near to the uterus-oviduct junction. For early stage embryos and morula, such embryos are either cultured in vitro into blastocysts or implanted into the oviducts of 0.5 dpc or 1.5 dpc pseudopregnant females according to the embryo stage. Chimeric pups from the implanted embryos are born 16-20 days after the transfer depending on the embryo age at implantation. Chimeric males are selected for breeding. Offspring can be analyzed for transmission of the embryonic stem cell genome by coat color and genetic analysis, such as PCR, Southern blot, or nucleic acid sequencing. Protein expression (e.g., of hSCF, hGM-SCF, hIL-3, and/or hCSF1) can be analyzed by protein analysis (Western blot, ELISA) or other functional assays. Offspring expressing the desired genetic modification can be intercrossed to create non-human animals homozygous for the genetic modification. The genetically modified mice can be crossed with immunodeficient mice to create a congenic immunodeficient strain genetically modified to express hSCF, hGM-SCF, hIL-3, and hCSF1.

A nucleotide sequence encoding a protein to be expressed can be targeted into a specific locus of the stem cell genome that is known to result in reliable expression such as the Hprt or the ROSA26 locus. For targeted transgenics, a targeting construct can be made using recombinant DNA techniques. The targeting construct can optionally include 5' and 3' sequences that are homologous to the endogenous gene target. The targeting construct can optionally further include a selectable marker such as neomycin phosphotransferase, hygromycin, or puromycin, a nucleic acid encoding hSCF, hGM-SCF, hIL-3, and/or hCSF1, and a polyadenylation signal, for example. To ensure correct transcription and translation of a nucleotide sequence encoding a desired xenogeneic protein, for example, the sequence is either in frame with the endogenous gene locus, or a splice acceptor site and internal ribosome entry site (IRES) sequence are included. Such a targeting construct can be transfected into stem cells, and the stem cells can be screened to detect the homologous recombination event using PCR, Southern blot, or nucleic acid sequencing. Cells with the correct homologous recombination event can be further analyzed for transgene expression by protein analysis, such as by ELISA or Western blot analysis. If desired, the selectable marker can be removed by treating the stem cells with Cre recombinase. After Cre recombinase treatment, the cells are analyzed for the presence of the nucleotide sequence encoding the expression construct or relevant portion thereof. Cells with the correct genomic event can be selected and injected into preimplantation embryos as described above. Chimeric males are selected for breeding. Offspring can be analyzed for transmission of the embryonic stem cell genome by coat color and genetic analysis, such as PCR, Southern blot, or nucleotide sequencing, and can be tested for xenogeneic protein expression such as by protein analysis (Western blot, ELISA) or other functional assays. Offspring expressing the desired genetic modification can be intercrossed to create animals homozygous for the genetic modification. Mice genetically modified to express hSCF, hGM-SCF, hIL-3, and hCSF1 can then be crossed with immunodeficient animals to create a congenic immunodeficient strain genetically modified to express hSCF, hGM-SCF, hIL-3, and hCSF1.

Embodiments of the invention provide a genetically modified immunodeficient QUAD mouse that includes a nucleotide sequence encoding hSCF, a nucleotide sequence encoding hGM-CSF, a nucleotide sequence encoding hIL-3, and a nucleotide sequence encoding hCSF1 in substantially all of their cells, as well as a genetically modified immunodeficient QUAD mouse that includes a nucleotide sequence encoding hSCF, a nucleotide sequence encoding hGM-CSF, a nucleotide sequence encoding hIL-3, and a nucleotide sequence encoding hCSF1 in some, but not all of their cells. One or multiple copies (such as concatamers) of the nucleotide sequence encoding hSCF, the nucleotide sequence encoding hGM-CSF, the nucleotide sequence encoding hIL-3, and/or the nucleotide sequence encoding hCSF1 can be integrated into the genomes of the cells of the immunodeficient QUAD mouse.

Any of various methods can be used to introduce a nucleotide sequence encoding hSCF, a nucleotide sequence encoding hGM-CSF, a nucleotide sequence encoding hIL-3, and a nucleotide sequence encoding hCSF1 into an immunodeficient mouse to produce an immunodeficient QUAD mouse. Such techniques are well-known in the art and include, but are not limited to, pronuclear microinjection and transformation of embryonic stem cells. Methods for generating genetically modified mice that can be used include, but are not limited to, those described in Sundberg and Ichiki, (Eds.), Genetically Engineered Mice Handbook, CRC Press, 2006; Hofker and van Deursen, (Eds.), Transgenic Mouse Methods and Protocols, Humana Press, 2002; Joyner, Gene Targeting: A Practical Approach, Oxford University Press, 2000; Manipulating the Mouse Embryo: A Laboratory Manual, $3^{rd}$ edition, Cold Spring Harbor Laboratory Press, Dec. 15, 2002, ISBN-10:0879695919; Turksen (Ed.), Embryonic stem cells: methods and protocols in Methods Mol Biol. 2002, 185, Humana Press; Current Protocols in Stem Cell Biology, ISBN: 978047015180; Meyer et al, PNAS USA, 107 (34): 15022-26.

Homology-based recombination gene modification strategies can be used to genetically modify an immunodeficient mouse by "knock-in" to introduce a nucleic acid encoding an exogenous protein or proteins e.g., a nucleotide sequence encoding hSCF, a nucleotide sequence encoding hGM-CSF, a nucleotide sequence encoding hIL-3, and a nucleotide sequence encoding hCSF1 into the genome of the immunodeficient mouse, such as homing endonucleases, integrases, meganucleases, transposons, nuclease-mediated processes using a zinc finger nuclease (ZFN), a Transcription Activator-Like (TAL), a Clustered Regularly Interspaced Short Palindromic Repeats (CRISPR)-Cas, or a *Drosophila* Recombination-Associated Protein (DRAP) approach. See, for example, Cerbini et al., PLOS One. 2015; 10 (1): c0116032; Shen et al., PLOS ONE 8 (10): c77696; and Wang et al., Protein & Cell, February 2016, Volume 7, Issue 2, pp 152-156.

An immunodeficient QUAD mouse according to aspects of the present invention expresses hSCF, hGM-CSF, hIL-3, and hCSF1, each at a serum concentration of at least about 0.1 pg/mL, 0.5 pg/mL, 1 pg/mL, 2 pg/mL, 5 pg/mL, 10 pg/mL, 15 pg/mL, 20 pg/mL, 25 pg/mL, 30 pg/mL, 40 pg/mL, 50 pg/mL, 60 pg/mL, 75 pg/mL, 100 pg/mL, 150 pg/mL, 200 pg/mL, 250 pg/mL, 300 pg/mL, 400 pg/mL, 500 pg/mL, 600 pg/mL, 750 pg/mL, 1 ng/mL, 2 ng/mL, 5 ng/mL, 10 ng/mL, 15 ng/mL, 20 ng/ml, 25 ng/ml, 30 ng/ml, 40 ng/mL, 50 ng/ml, 60 ng/ml, 75 ng/mL, 100 ng/mL, 150 ng/ml, 200 ng/ml, 250 ng/ml, 300 ng/mL, 400 ng/mL, 500 ng/mL, 600 ng/mL, or 750 ng/mL.

An immunodeficient QUAD mouse according to aspects of the present invention expresses hSCF, hGM-CSF, hIL-3, and hCSF1, each at a serum concentration of about 0.1 pg/mL to about 1000 ng/ml, about 0.1 pg/mL to about 100 ng/ml, about 0.5 pg/mL to about 50 ng/ml, about 1 pg/mL to about 10 ng/ml, about 0.1 pg/mL to about 100 pg/mL, about 1 pg/mL to about 1 ng/ml, about 10 pg/mL to about 10 ng/mL, about 100 pg/mL to about 100 ng/ml, about 0.1 pg/mL to about 10 pg/mL, about 1 pg/mL to about 100 pg/mL, about 10 pg/mL to about 1 ng/ml, about 100 pg/mL to about 10 ng/mL, about 1 ng/ml to about 100 ng/ml, about 0.1 pg/mL to about 1 pg/mL, about 0.5 pg/mL to about 5 pg/mL, about 1 pg/mL to about 10 pg/mL, about 5 pg/mL to about 50 pg/mL, about 10 pg/mL to about 100 pg/mL, about 50 pg/mL to about 500 pg/mL, about 100 pg/mL to about 1 ng/mL, about 500 pg/mL to about 5 ng/ml, about 1 ng/mL to about 10 ng/ml, about 5 ng/ml to about 50 ng/ml, about 10 ng/ml to about 100 ng/mL, about 50 ng/mL to about 500 ng/ml, about 0.5 ng/ml to about 50 ng/ml, about 1 ng/mL to about 25 ng/ml, about 0.5 ng/ml to about 20 ng/ml, about 0.1 ng/ml to about 5 ng/ml, about 0.5 ng/ml to about 10 ng/ml, about 2 ng/ml to about 20 ng/mL, about 1 ng/mL to about 5 ng/ml, or about 2 ng/ml to about 4 ng/mL.

Aspects of the present invention, an immunodeficient QUAD mouse expresses hSCF, hGM-CSF, hIL-3, and hCSF1, each at a serum concentration of about 1 ng/ml to about 10 ng/mL.

Immunodeficiency

The term "immunodeficient mouse" refers to a mouse characterized by one or more of: a lack of functional immune cells, such as T cells and B cells; a DNA repair defect; a defect in the rearrangement of genes encoding antigen-specific receptors on lymphocytes; and a lack of immune functional molecules such as IgM, IgG1, IgG2a, IgG2b, IgG3 and IgA. Immunodeficient mice can be characterized by one or more deficiencies in a gene involved in immune function, such as Rag1 and Rag2 (Oettinger, M. A et al., Science, 248:1517-1523, 1990; and Schatz, D. G. et al., Cell, 59:1035-1048, 1989) Immunodeficient mice may have any of these or other defects which result in abnormal immune function in the mice.

According to particular aspects, an immunodeficient QUAD mouse has a defect in its endogenous gene encoding interleukin-2 receptor γ subunit (IL-2RG) which causes the mouse to express a defective endogenous interleukin-2 receptor γ subunit and/or a reduced amount of endogenous interleukin-2 receptor γ subunit, or the mouse may not express an endogenous interleukin-2 receptor γ subunit at all. The immunodeficient QUAD can optionally be IL-2RG null such that it lacks a functional endogenous IL-2RG gene.

In further aspects, a immunodeficient QUAD mouse has a defect in its endogenous gene encoding DNA-dependent protein kinase, catalytic subunit (Prkdc) which causes the mouse to express a defective endogenous DNA-dependent protein kinase, catalytic subunit and/or a reduced amount of endogenous DNA-dependent protein kinase, catalytic subunit, or the mouse may not express endogenous DNA-dependent protein kinase, catalytic subunit at all. The immunodeficient QUAD mouse can optionally be Prkdc null such that it lacks a functional endogenous Prkdc gene).

"Endogenous," as used herein in relation to genes and the proteins they encode, refers to genes present in the genome of the mouse at their native gene locus.

In various aspects of the present invention, an immunodeficient QUAD mouse is IL-2rg null and/or Prkdc null, lacking functional endogenous IL-2rg and Prkdc genes. The immunodeficient QUAD mouse can optionally include a Prkdc knockout and/or an IL-2rg knockout. In various aspects of the present invention, the immunodeficient QUAD mouse does not express IL-2RG, does not express Prkdc, or does not express both IL-2RG and Prkdc.

In various aspects of the present invention, an immunodeficient QUAD mouse has severe-combined immunodeficiency. The term "severe combined immune deficiency" or "SCID" refers to a condition characterized by the absence or severe reduction of function of T cells and B cells.

Common forms of SCID include: X-linked SCID, which is characterized by gamma chain gene mutations in the IL-2RG gene and the lymphocyte phenotype T (−) B (+) NK(−). and autosomal recessive SCID. Autosomal recessive SCID can be characterized by Jak3 gene mutations and the lymphocyte phenotype T (−) B (+) NK (−), ADA gene mutations and the lymphocyte phenotype T (−) B (−) NK (−), IL-7R alpha-chain mutations and the lymphocyte phenotype T (−) B (+) NK (+), CD3 delta or epsilon mutations and the lymphocyte phenotype T (−) B (+) NK (+), RAG1/RAG2 mutations and the lymphocyte phenotype T (−) B (−) NK (+), Artemis gene mutations and the lymphocyte phenotype T (−) B (−) NK (+), and CD45 gene mutations and the lymphocyte phenotype T (−) B (+) NK (+).

According to aspects of the present invention, an immunodeficient QUAD mouse has the severe combined immunodeficiency mutation (Prkdc$^{scid}$), commonly referred to as the scid mutation. The seid mutation is well-known and located on mouse chromosome 16 as described in Bosma et al, 1989, Immunogenetics 29:54-56. Mice homozygous for the scid mutation are characterized by an absence of functional T cells and B cells, lymphopenia, hypoglobulinemia, and a normal hematopoctic microenvironment. The scid mutation can be detected, for example, by the detection of markers for the scid mutation using well-known methods such as PCR or flow cytometry.

A genetically modified immunodeficient mouse according to aspects of the present invention has an IL-2 receptor gamma chain deficiency. The term "IL-2 receptor gamma chain deficiency" refers to decreased IL-2 receptor gamma chain. Decreased IL-2 receptor gamma chain can be due to gene deletion or mutation. Decreased IL-2 receptor gamma chain can be detected, for example, by detection of IL-2 receptor gamma chain gene deletion or mutation and/or detection of decreased IL-2 receptor gamma chain expression using well-known methods.

An immunodeficient QUAD mouse according to aspects of the present invention has severe combined immunodeficiency or an IL-2 receptor gamma chain deficiency in combination with severe combined immunodeficiency.

An immunodeficient QUAD mouse according to aspects of the present invention has the scid mutation or an IL-2 receptor gamma chain deficiency in combination with the scid mutation.

In various aspects of the present invention, the immunodeficient QUAD mouse is a genetically modified NSG mouse, a genetically modified NRG mouse or a genetically modified NOG mouse, wherein the genome of the genetically-modified NSG, NRG or NOG mouse includes a nucleotide sequence encoding hSCF, a nucleotide sequence encoding hGM-CSF, a nucleotide sequence encoding hIL-3, and a nucleotide sequence encoding hCSF1, wherein the mouse expresses hSCF, hGM-CSF, hIL-3, and hCSF1 proteins.

The terms "NOD scid gamma," "NOD-scid IL2rg$^{null}$" and "NSG" are used interchangeably herein to refer to a well-known immunodeficient mouse strain NOD.Cg-Prkdc$^{scid}$ IL-2rg$^{tm1Wjl}$/SzJ, described in detail in Shultz L D et al, 2005, J. Immunol, 174:6477-89. NSG mice combine multiple immune deficits from the NOD/ShiLtJ background, the severe combined immune deficiency (scid) mutation, and a complete knockout of the interleukin-2 receptor gamma chain. As a result, NSG mice lack mature mouse T, B, and NK cells, and they are deficient in multiple mouse cytokine signaling pathways. NSG mice are characterized by a lack of mouse IL-2R-γ (gamma c) expression, no detectable mouse serum immunoglobulin, no mouse hemolytic complement, no mature mouse T lymphocytes, and no mature mouse natural killer cells.

An NSG mouse that expresses hSCF, hGM-CSF, hIL-3, and hCSF1 is referred to as a "NSG-QUAD" mouse, which indicates that the genome of the genetically-modified NSG, mouse includes a nucleotide sequence encoding hSCF, a nucleotide sequence encoding hGM-CSF, a nucleotide sequence encoding hIL-3, and a nucleotide sequence encoding hCSF1, on the NOD.Cg-Prkdc$^{scid}$ IL-2rg$^{tm1Wjl}$/SzJ background, wherein the mouse expresses hSCF, hGM-CSF, hIL-3, and hCSF1 proteins.

NRG mice are well-known as NOD.Cg-Rag1$^{tm1Mom}$ Il2rg$^{tm1Wjl}$/SzJ, described in detail in Shultz L D et al, 2008 Clin Exp Immunol 154 (2): 270-84.

Advantageously. NSG-QUAD mice exhibit a significantly hightened level of CD33$^+$/CD14$^+$ human monocytes and CD56$^+$ human NK cells in the blood when engrafted with human hematopoietic stem cells when compared with NSG mice.

NSG-QUAD mice also exhibit a surprising property of an enhanced development of human monocytes and NK cells when engrafted with human hematopoictic stem cells. There is disclosed an enhanced functional human immune response to innate stimulation with lipopolysaccharide (LPS) in the HSC-engrafted NSG-QUAD mice, making this mouse model particularly valuable in the study of human immune responses to various stimuli.

An NRG mouse that expresses hSCF, hGM-CSF, hIL-3, and hCSF1 is referred to as a "NRG-QUAD" mouse, which indicates that the genome of the genetically-modified NRG, mouse includes a nucleotide sequence encoding hSCF, a nucleotide sequence encoding hGM-CSF, a nucleotide sequence encoding hIL-3, and a nucleotide sequence encoding hCSF1, on the NOD.Cg-Rag1$^{tm1Mom}$ Il2rg$^{tm1Wjl}$/SzJ background, wherein the mouse expresses hSCF, hGM-CSF, hIL-3, and hCSF1 proteins.

NOG mice are well-known as NOD.Cg-Prkdc$^{scid}$ Il2rg$^{tm1Sug}$/JicTac, described in detail in Ito, M. et al., Blood 100, 3175-3182 (2002).

A NOG mouse that expresses hSCF, hGM-CSF, hIL-3, and hCSF1 is referred to as a "NOG-QUAD" mouse, which indicates that the genome of the genetically-modified NOG, mouse includes a nucleotide sequence encoding hSCF, a nucleotide sequence encoding hGM-CSF, a nucleotide sequence encoding hIL-3, and a nucleotide sequence encoding hCSF1, on the NOD.Cg-Prkdc$^{scid}$ Il2rg$^{tm1Sug}$/JicTac background.

Hematopoietic Stem Cell Xenografts

Various aspects of the invention relate to administering xenogeneic hematopoietic stem cells (HSC) to an immunodeficient QUAD mouse, producing an immunodeficient QUAD mouse having engrafted HSC.

The xenogeneic HSC are human HSC according to aspects of the present invention.

The term "xenogeneic HSC" as used herein refers to multipotent stem cells expressing c-Kit receptor. Examples of multipotent stem cells expressing c-Kit receptor include, but are not limited to, hematopoietic stem cells, also known as hemocytoblasts. C-Kit receptor is well-known in the art, for example as described in Vandenbark G R et al., 1992, Cloning and structural analysis of the human c-kit gene, Oncogene 7 (7): 1259-66; and Edling C E, Hallberg B, 2007, c-Kit—a hematopoietic cell essential receptor tyrosine kinase, Int. J. Biochem. Cell Biol. 39 (11): 1995-8.

Isolation of xenogeneic HSC, administration of the xenogeneic HSC to a host mouse and methods for assessing engraftment in the host mouse thereof are well-known in the art.

Hematopoietic stem cells for administration to an immunodeficient QUAD mouse can be obtained from any tissue containing HSC such as, but not limited to, umbilical cord blood, bone marrow, GM-CSF-mobilized peripheral blood and fetal liver.

Xenogeneic HSC can be administered into newborn mice by administration via various routes, such as, but not limited to, into the heart, liver and/or facial vein. Xenogencic HSC can be administered into adult mice by various routes, such as, but not limited to, administration into the tail vein, into the femur bone marrow cavity or into the spleen. In a further example, fetal liver containing the xenogeneic HSC can be engrafted under the renal capsule.

Administering xenogeneic cells to a mouse can include administering a composition comprising xenogeneic cells to the mouse. The composition can further include, for example, water, a tonicity-adjusting agent (e.g., a salt such as sodium chloride), a pH buffer (e.g., citrate), and/or a sugar (e.g., glucose).

Engraftment of xenogeneic hematopoietic stem cells in immunodeficient animals is characterized by the presence of differentiated xenogeneic hematopoietic cells in the immunodeficient QUAD mice. Engraftment of xenogeneic HSC can be assessed by any of various methods, such as, but not limited to, flow cytometric analysis of cells in the animals to which the xenogeneic HSC are administered at one or more time points following the administration of HSC.

Exemplary methods for isolation of xenogeneic HSC, administration of the xenogeneic HSC to a host mouse and methods for assessing engraftment thereof are described herein and in T. Pearson et al., Curr. Protoc. Immunol. 81:15.21.1-15.21.21, 2008; Ito, M. et al, Blood 100:3175-3182; Traggiai, E. et al, Science 304:104-107; Ishikawa, F. et al, Blood 106:1565-1573; Shultz, L. D. et al, J. Immunol. 174:6477-6489; Holyoake T L et al, Exp Hematol., 1999, 27 (9): 1418-27.

According to aspects of the present invention, the xenogeneic HSC administered to an immunodeficient QUAD mouse are isolated from an original source material to obtain a population of cells enriched in HSCs. The isolated xenogeneic HSCs may or may not be pure. According to aspects, xenogeneic HSCs are purified by selection for a cell marker, such as CD34. According to aspects, administered xenogeneic HSCs are a population of cells in which CD34$^+$ cells constitute about 1-100% of total cells, although a population of cells in which CD34$^+$ cells constitute fewer than about 1% of total cells can be used. According to embodiments, administered xenogeneic HSCs are T cell depleted cord blood cells in which CD34$^+$ cells make up about 1-3% of total cells, lineage depleted cord blood cells in which CD34$^+$ cells make up about 50% of total cells, or CD34$^+$ positively selected cells in which CD34$^+$ cells make up about 90% of total cells.

The number of xenogeneic HSCs administered is not considered limiting with regard to generation of a xenogeneic hematopoietic and immune system in an immunodeficient QUAD mouse. A single xenogeneic HSC can generate a hematopoietic and immune system in a host immunodeficient QUAD mouse. Thus, the number of administered xenogeneic HSCs is generally in the range of about $1\times10^3$ to $1\times10^6$ (1,000 to 1,000,000) CD34$^+$ cells where the recipient is a mouse, although more or fewer can be used.

Thus, a method according to aspects of the present invention can include administering about $10^3$ (1000) to about 106 (1,000,000), about $10^3$ to about $10^5$, about $10^4$ to about $10^6$, about $10^5$ to about $10^7$, about $1\times10^3$ to about $1\times10^4$, about $5\times10^3$ to about $5\times10^4$, about $1\times10^4$ to about $1\times10^5$, about $5\times10^4$ to about $5\times10^5$, about $1\times10^5$ to about $1\times10^6$, about $5\times10^5$ to about $5\times10^6$, about $1\times10^6$ to about $1 \times 10^7$, about $2 \times 10^4$ to about $5 \times 10^5$, or about $5 \times 10^4$ to about $2 \times 10^5$ xenogeneic HSC, such as human hematopoietic stem cells, to the immunodeficient QUAD mouse. The method can include administering at least about $1 \times 10^2$, about $2 \times 10^2$, about $3 \times 10^2$, about $4 \times 10^2$, about $5 \times 10^2$, about $6 \times 10^2$, about $7 \times 10^2$, about $8 \times 10^2$, about $9 \times 10^2$, about $1 \times 10^3$, about $2 \times 10^3$, about $3 \times 10^3$, about $4 \times 10^3$, about $5 \times 10^3$, about $6 \times 10^3$, about $7 \times 10^3$, about $8 \times 10^3$, about $9 \times 10^3$, about $1 \times 10^4$, about $2 \times 10^4$, about $3 \times 10^4$, about $4 \times 10^4$, about $5 \times 10^4$, about $6 \times 10^4$, about $7 \times 10^4$, about $8 \times 10^4$, about $9 \times 10^4$, about $1 \times 10^5$, about $2 \times 10^5$, about $3 \times 10^5$, about $4 \times 10^5$, about $5 \times 10^5$, about $6 \times 10^5$, about $7 \times 10^5$, about $8 \times 10^5$, about $9 \times 10^5$, about $1 \times 10^6$, about $2 \times 10^6$, about $3 \times 10^6$, about $4 \times 10^6$, about $5 \times 10^6$, about $6 \times 10^6$, about $7 \times 10^6$, about $8 \times 10^6$, about $9 \times 10^6$, or about $1 \times 10^7$ xenogeneic HSC, such as human hematopoietic stem cells, to the immunodeficient QUAD mouse. The method can include administering about $1 \times 10^2$, about $2 \times 10^2$, about $3 \times 10^2$, about $4 \times 10^2$, about $5 \times 10^2$, about $6 \times 10^2$, about $7 \times 10^2$, about $8 \times 10^2$, about $9 \times 10^2$, about $1 \times 10^3$, about $2 \times 10^3$, about $3 \times 10^3$, about $4 \times 10^3$, about $5 \times 10^3$, about $6 \times 10^3$, about $7 \times 10^3$, about $8 \times 10^3$, about $9 \times 10^3$, about $1 \times 10^4$, about $2 \times 10^4$, about $3 \times 10^4$, about $4 \times 10^4$, about $5 \times 10^4$, about $6 \times 10^4$, about $7 \times 10^4$, about $8 \times 10^4$, about $9 \times 10^4$, about $1 \times 10^5$, about $2 \times 10^5$, about $3 \times 10^5$, about $4 \times 10^5$, about $5 \times 10^5$, about $6 \times 10^5$, about $7 \times 10^5$, about $8 \times 10^5$, about $9 \times 10^5$, about $1 \times 10^6$, about $2 \times 10^6$, about $3 \times 10^6$, about $4 \times 10^6$, about $5 \times 10^6$, about $6 \times 10^6$, about $7 \times 10^6$, about $8 \times 10^6$, about $9 \times 10^6$, or about $1 \times 10^7$ xenogeneic HSC, such as human HSC, to the immunodeficient QUAD mouse. Those of ordinary skill will be able to determine a number of xenogeneic cells that should be administered to a specific mouse using no more than routine experimentation.

Engraftment is successful where xenogenic HSCs and/or cells differentiated from the xenogeneic HSCs in the recipient immunodeficient QUAD mouse are detected at a time when the majority of any administered non-HSC have degenerated. Detection of differentiated xenogeneic HSC cells can be achieved by detection of xenogeneic DNA in the recipient immunodeficient QUAD mouse or detection of intact xenogeneic HSCs and cells differentiated from the xenogeneic HSCs, for example. Serial transfer of $CD34^+$ cells into a secondary recipient and engraftment of a xenogeneic hematopoietic system is a further test of HSC engraftment in the primary recipient. Engraftment can be detected by flow cytometry as 0.05% or greater xenogeneic $CD45^+$ cells in the blood, spleen or bone marrow of the recipient immunodeficient QUAD mouse at 6-12 weeks after administration of the xenogeneic HSC.

Engraftment of xenogeneic haematopoietic stem cells (HSC) in an immunodeficient QUAD mouse according to aspects of the present invention includes "conditioning" of the immunodeficient QUAD mouse prior to administration of the xenogencic HSC, for example by sub-lethal irradiation of the recipient animal with high frequency electromagnetic radiation, or gamma radiation, or treatment with a radiomimetic drug such as busulfan or nitrogen mustard. Conditioning is believed to reduce numbers of host hematopoietic cells, create appropriate microenvironmental factors for engraftment of xenogeneic HSC, and/or create microenvironmental niches for engraftment of xenogeneic HSC. Standard methods for conditioning are known in the art, such as described herein and in J. Hayakawa et al, 2009, Stem Cells, 27 (1): 175-182.

Methods are provided according to aspects of the present invention which include administration of xenogeneic HSC to an immunodeficient QUAD mouse without "conditioning" the immunodeficient QUAD mouse prior to administration of the xenogeneic HSC. Methods are provided according to aspects of the present invention which include administration of xenogeneic HSC to an immunodeficient QUAD mouse without "conditioning" by radiation or radiomimetic drugs of the immunodeficient QUAD mouse prior to administration of the xenogeneic HSC.

Various aspects of the invention relate to administering xenogeneic hematopoietic stem cells (HSC) to an immunodeficient QUAD mouse, producing an immunodeficient QUAD mouse having engrafted HSC. The engrafted xenogeneic HSC differentiate to produce an immunodeficient QUAD mouse with a xenogeneic immune system or components thereof.

Administration of xenogeneic HSC to an immunodeficient QUAD mouse results in the production of differentiated xenogeneic cells of hematopoietic lineage in the mouse. For example, administration of xenogeneic HSC to an immunodeficient QUAD mouse results in the production of xenogeneic myeloid-lineage and xenogeneic lymphoid-lineage cells by the mouse such as xenogeneic $CD33^+$ myeloid cells, xenogeneic myeloid progenitor cells, xenogeneic mast cells, xenogeneic myeloid dendritic cells, xenogeneic B cells, xenogeneic T cells, xenogeneic T helper cells, xenogeneic cytotoxic T cells, and/or xenogeneic Treg cells. According to aspects of the present invention, human HSC are administered to an immunodeficient QUAD mouse which differentiate such that the mouse includes one or more of: human $CD33^+$ myeloid cells, human myeloid progenitor cells, human mast cells, human myeloid dendritic cells, human B cells, human T cells, human T helper cells, human cytotoxic T cells, and/or human Treg cells.

Administration of xenogeneic HSC to an immunodeficient QUAD mouse results in the production of differentiated xenogeneic cells of hematopoietic lineage that can be characterized by flow cytometry. For example, administration of human HSC to an immunodeficient QUAD mouse results in the production of differentiated human cells of hematopoietic lineage that can be characterized by flow cytometry, including human leukocytes selected from 1, 2, 3, 4, 5, 6, 7, 8, 9, 10, or all of $CD45^+$, $CD20^+$, $CD20^+CD45^+$, $CD3^+$, $CD3^+CD45^+$, $CD33^+$, $CD33^+CD45^+$, $CD14^+$, $CD14^+CD45+$, $CD56^+$, and $CD56^+CD45^+$ human leukocytes.

According to aspects disclosed herein, administration of human HSC to an immunodeficient QUAD mouse results in the production of differentiated human cells of hematopoietic lineage such as human $CD45^+$ leukocytes, wherein at least about 20%, 25%, 30%, 35%, 40%, 45%, 50%, 55%, 60%, or more of the human $CD45^+$ leukocytes of the mouse are $CD3^+CD45^+$ leukocytes; at least about 10%, 15%, 20%, 25%, 30%, 35%, or more of the human $CD45^+$ leukocytes of the mouse are $CD33^+CD45^+$ leukocytes; at least about 5%, 10%, 15%, 20%, or more of the human $CD45^+$ leukocytes of the mouse are $CD14^+CD45^+$ leukocytes; and/or at least about 0.5%, 0.6%, 0.7%, 0.8%, 0.9%, 1.0%, 1.1%, 1.2%, 1.3%, 1.4%, 1.5%, 1.6%, 1.7%, 1.8%, 1.9%, 2.0%, or more of the human $CD45^+$ leukocytes of the mouse are $CD56^+CD45^+$ leukocytes (e.g., in the absence of an immunological challenge such as a tumor or antigen challenge).

According to aspects disclosed herein, administration of human HSC to an immunodeficient QUAD mouse results in the production of differentiated human cells of hematopoietic lineage such as human leukocytes, wherein at least about 20%, 25%, 30%, 35%, 40%, 45%, 50%, 55%, 60%, or more of the human leukocytes of the mouse are either cytotoxic T-cells or T-helper cells; at least about 10%, 15%, 20%, 25%, 30%, 35%, or more of the human leukocytes of the mouse are myeloid-lineage cells; at least about 5%, 10%, 15%, 20%, or more of the human leukocytes of the mouse are macrophages; and/or at least about 0.5%, 0.6%, 0.7%, 0.8%, 0.9%, 1.0%, 1.1%, 1.2%, 1.3%, 1.4%, 1.5%, 1.6%, 1.7%, 1.8%, 1.9%, 2.0%, or more of the human leukocytes of the mouse are natural killer cells (e.g., in the absence of an immunological challenge such as a tumor or antigen challenge).

According to aspects disclosed herein, administration of xenogeneic HSC to an immunodeficient QUAD mouse results in the production of xenogeneic cytokines by the mouse such as interleukin-8, interleukin-1β, tumor-necrosis factor, interleukin-12p70, and/or interleukin-6. For example, administration of human HSC to an immunodeficient QUAD mouse results in the production of 1, 2, 3, 4, or all of human interleukin-8, human interleukin-1ß, human tumor-necrosis factor, human interleukin-12p70, and human interleukin-6.

According to aspects disclosed herein, administration of xenogeneic HSC to an immunodeficient QUAD mouse results in the production of xenogeneic cytokines in response to an immune challenge, e.g., at a detectable level and/or at a level capable of mediating a xenogeneic immune response against the challenge. According to aspects disclosed herein, administration of human HSC to an immunodeficient QUAD mouse results in at least about 0.1 pg/mL, 0.5 pg/mL, 1 pg/mL, 2 pg/mL, 5 pg/mL, 10 pg/mL, 15 pg/mL, 20 pg/mL, 25 pg/mL, 30 pg/mL, 40 pg/mL, 50 pg/mL, 60 pg/mL, 75 pg/mL, 100 pg/mL, 150 pg/mL, 200 pg/mL, 250 pg/mL, 300 pg/mL, 400 pg/mL, 500 pg/mL, 600 pg/mL, 750 pg/mL, 1 ng/mL, 2 ng/mL, 5 ng/ml, 10 ng/mL, 15 ng/mL, or more serum human interleukin-8 in the mouse. According to aspects disclosed herein, administration of human HSC to an immunodeficient QUAD mouse results in the production of at least about 0.1 pg/mL, 0.5 pg/mL, 1 pg/mL, 2 pg/mL, 5 pg/mL, 10 pg/mL, 15 pg/mL, 20 pg/mL, 25 pg/mL, 30 pg/mL, 40 pg/mL, 50 pg/mL, 60 pg/mL, 75 pg/mL, 100 pg/mL, 150 pg/mL, 200 pg/mL, 250 pg/mL, or more serum human interleukin-1ß in the mouse. According to aspects disclosed herein, administration of human HSC to an immunodeficient QUAD mouse results in at least about 0.1 pg/mL, 0.5 pg/mL, 1 pg/mL, 2 pg/mL, 5 pg/mL, 10 pg/mL, 15 pg/mL, 20 pg/mL, 25 pg/mL, 30 pg/mL, 40 pg/mL, 50 pg/mL, 60 pg/mL, 75 pg/mL, 100 pg/mL, 150 pg/mL, 200 pg/mL, 250 pg/mL, 300 pg/mL, 400 pg/mL, 500 pg/mL, 600 pg/mL, 750 pg/mL, 1 ng/ml, 2 ng/mL, 5 ng/mL, 10 ng/mL, 15 ng/mL, 20 ng/mL, 25 ng/mL, 30 ng/mL, 40 ng/ml, 50 ng/mL, or more serum human tumor-necrosis factor in the mouse. According to aspects disclosed herein, administration of human HSC to an immunodeficient QUAD mouse results in at least about 0.1 pg/mL, 0.5 pg/mL, 1 pg/mL, 2 pg/mL, 5 pg/mL, 10 pg/mL, 15 pg/mL, 20 pg/mL, 25 pg/mL, 30 pg/mL, 40 pg/mL, 50 pg/mL, 60 pg/mL, 75 pg/mL, 100 pg/mL, or more serum human interleukin-12p70 in the mouse. According to aspects disclosed herein, administration of human HSC to an immunodeficient QUAD mouse results in at least about 0.1 pg/mL, 0.5 pg/mL, 1 pg/mL, 2 pg/mL, 5 pg/mL, 10 pg/mL, 15 pg/mL, 20 pg/mL, 25 pg/mL, 30 pg/mL, 40 pg/mL, 50 pg/mL, 60 pg/mL, 75 pg/mL, 100 pg/mL, 150 pg/mL, 200 pg/mL, 250 pg/mL, 300 pg/mL, 400 pg/mL, 500 pg/mL, 600 pg/mL, 750 pg/mL, 1 ng/mL, 2 ng/ml, 5 ng/mL, 10 ng/mL, 15 ng/ml, 20 ng/ml, 25 ng/ml, 30 ng/mL, or more serum human interleukin-6 in the mouse.

According to aspects disclosed herein, administration of human HSC to an immunodeficient QUAD mouse results in about 0.1 pg/mL to about 1000 ng/ml, about 0.1 pg/mL to about 100 ng/ml, about 0.5 pg/mL to about 50 ng/ml, about 1 pg/mL to about 10 ng/mL, about 0.1 pg/mL to about 100 pg/mL, about 1 pg/mL to about 1 ng/mL, about 10 pg/mL to about 10 ng/ml, about 100 pg/mL to about 100 ng/ml, about 0.1 pg/mL to about 10 pg/mL, about 1 pg/mL to about 100 pg/mL, about 10 pg/mL to about 1 ng/ml, about 100 pg/mL to about 10 ng/ml, about 1 ng/ml to about 100 ng/mL, about 0.1 pg/mL to about 1 pg/mL, about 0.5 pg/mL to about 5 pg/mL, about 1 pg/mL to about 10 pg/mL, about 5 pg/mL to about 50 pg/mL, about 10 pg/mL to about 100 pg/mL, about 50 pg/mL to about 500 pg/mL, about 100 pg/mL to about 1 ng/ml, about 500 pg/mL to about 5 ng/ml, about 1 ng/mL to about 10 ng/ml, about 5 ng/ml to about 50 ng/ml, about 10 ng/mL to about 100 ng/ml, about 50 ng/mL to about 500 ng/ml, about 0.5 ng/ml to about 50 ng/ml, about 1 ng/mL to about 25 ng/ml, about 0.5 ng/ml to about 20 ng/mL, about 0.1 ng/mL to about 5 ng/mL, about 0.5 ng/mL to about 10 ng/mL, or about 2 ng/mL to about 20 ng/mL serum human interleukin-8 in the mouse.

According to aspects disclosed herein, administration of human HSC to an immunodeficient QUAD mouse results in about 0.1 pg/mL to about 1000 ng/ml, about 0.1 pg/mL to about 100 ng/ml, about 0.5 pg/mL to about 50 ng/ml, about 1 pg/mL to about 10 ng/ml, about 0.1 pg/mL to about 100 pg/mL, about 1 pg/mL to about 1 ng/mL, about 10 pg/mL to about 10 ng/ml, about 100 pg/mL to about 100 ng/ml, about 0.1 pg/mL to about 10 pg/mL, about 1 pg/mL to about 100 pg/mL, about 10 pg/mL to about 1 ng/mL, about 100 pg/mL to about 10 ng/ml, about 1 ng/mL to about 100 ng/ml, about 0.1 pg/mL to about 1 pg/mL, about 0.5 pg/mL to about 5 pg/mL, about 1 pg/mL to about 10 pg/mL, about 5 pg/mL to about 50 pg/mL, about 10 pg/mL to about 100 pg/mL, about 50 pg/mL to about 500 pg/mL, or about 100 pg/mL to about 1 ng/ml serum human interleukin-1β in the mouse.

According to aspects disclosed herein, administration of human HSC to an immunodeficient QUAD mouse results in about 0.1 pg/mL to about 1000 ng/ml, about 0.1 pg/mL to about 100 ng/ml, about 0.5 pg/mL to about 50 ng/ml, about 1 pg/mL to about 10 ng/ml, about 0.1 pg/mL to about 100 pg/mL, about 1 pg/mL to about 1 ng/ml, about 10 pg/mL to about 10 ng/ml, about 100 pg/mL to about 100 ng/ml, about 0.1 pg/mL to about 10 pg/mL, about 1 pg/mL to about 100 pg/mL, about 10 pg/mL to about 1 ng/mL, about 100 pg/mL to about 10 ng/ml, about 1 ng/ml to about 100 ng/ml, about 0.1 pg/mL to about 1 pg/mL, about 0.5 pg/mL to about 5 pg/mL, about 1 pg/mL to about 10 pg/mL, about 5 pg/mL to about 50 pg/mL, about 10 pg/mL to about 100 pg/mL, about 50 pg/mL to about 500 pg/mL, about 100 pg/mL to about 1 ng/ml, about 500 pg/mL to about 5 ng/ml, about 1 ng/ml to about 10 ng/ml, about 5 ng/ml to about 50 ng/ml, about 10 ng/ml to about 100 ng/ml, about 50 ng/mL to about 500 ng/ml, about 0.5 ng/ml to about 50 ng/ml, about 1 ng/ml to about 25 ng/ml, or about 0.5 ng/ml to about 20 ng/mL serum human tumor-necrosis factor in the mouse.

According to aspects disclosed herein, administration of human HSC to an immunodeficient QUAD mouse results in about 0.1 pg/mL to about 1000 ng/ml, about 0.1 pg/mL to about 100 ng/ml, about 0.5 pg/mL to about 50 ng/ml, about 1 pg/mL to about 10 ng/mL, about 0.1 pg/mL to about 100 pg/mL, about 1 pg/mL to about 1 ng/mL, about 10 pg/mL to about 10 ng/ml, about 100 pg/mL to about 100 ng/mL, about 0.1 pg/mL to about 10 pg/mL, about 1 pg/mL to about 100 pg/mL, about 10 pg/mL to about 1 ng/mL, about 100 pg/mL to about 10 ng/ml, about 0.1 pg/mL to about 1 pg/mL, about 0.5 pg/mL to about 5 pg/mL, about 1 pg/mL to about 10 pg/mL, about 5 pg/mL to about 50 pg/mL, about 10 pg/mL to about 100 pg/mL, or about 50 pg/mL to about 500 pg/mL serum human interleukin-12p70 in the mouse.

According to aspects disclosed herein, administration of human HSC to an immunodeficient QUAD mouse results in about 0.1 pg/mL to about 1000 ng/ml, about 0.1 pg/mL to about 100 ng/ml, about 0.5 pg/mL to about 50 ng/ml, about 1 pg/mL to about 10 ng/ml, about 0.1 pg/mL to about 100 pg/mL, about 1 pg/mL to about 1 ng/ml, about 10 pg/mL to about 10 ng/ml, about 100 pg/mL to about 100 ng/ml, about 0.1 pg/mL to about 10 pg/mL, about 1 pg/mL to about 100 pg/mL, about 10 pg/mL to about 1 ng/ml, about 100 pg/mL to about 10 ng/ml, about 1 ng/ml to about 100 ng/mL, about 0.1 pg/mL to about 1 pg/mL, about 0.5 pg/mL to about 5 pg/mL, about 1 pg/mL to about 10 pg/mL, about 5 pg/mL to about 50 pg/mL, about 10 pg/mL to about 100 pg/mL, about 50 pg/mL to about 500 pg/mL, about 100 pg/mL to about 1 ng/ml, about 500 pg/mL to about 5 ng/ml, about 1 ng/mL to about 10 ng/mL, about 5 ng/ml to about 50 ng/ml, about 10 ng/ml to about 100 ng/ml, about 50 ng/ml to about 500 ng/ml, about 0.5 ng/ml to about 50 ng/ml, about 1 ng/mL to about 25 ng/ml, about 0.5 ng/mL to about 20 ng/mL, about 0.1 ng/ml to about 5 ng/ml, about 0.5 ng/ml to about 10 ng/ml, or about 2 ng/mL to about 20 ng/ml serum human interleukin-6 in the mouse.

According to aspects disclosed herein, administration of human HSC to an immunodeficient QUAD mouse results in about 5-15 ng/ml serum human interleukin-8, about 5-250 pg/mL serum human interleukin-1B, about 10-50 ng/ml serum human tumor-necrosis factor, about 20-100 pg/mL serum human interleukin-12p70, and/or about 15-30 ng/ml serum human interleukin-6 (e.g., when challenged with about 50-250 ng intravenous lipopolysaccharide) in the mouse.

According to aspects disclosed herein, administration of xenogeneic HSC to an immunodeficient QUAD mouse results in production of xenogeneic leukocytes that migrate into a tumor, such as xenogeneic tumor-infiltrating lymphocytes and xenogeneic myeloid-derived suppressor cells, in the immunodeficient QUAD mouse. According to aspects disclosed herein, administration of human HSC to an immunodeficient QUAD mouse results in production of human leukocytes that migrate into a tumor, such as human tumor-infiltrating lymphocytes and human myeloid-derived suppressor cells, in the immunodeficient QUAD mouse. For example, such tumor-infiltrating leukocytes are selected from $CD20^+$, $CD3^+$, $CD33^+$, $CD14^+$, and $CD56^+$ leukocytes.

Tumor Xenograft

Various aspects of the invention relate to administering xenogeneic tumor cells to an immunodeficient QUAD mouse.

Xenogeneic tumor cells administered to immunodeficient QUAD mice of the present invention can be any of various tumor cells, including but not limited to, cells of a tumor cell line and primary tumor cells. The xenogeneic tumor cells may be derived from any of various organisms, preferably mammalian, including human, non-human primate, rat, guinea pig, rabbit, cat, dog, horse, cow, goat, pig and sheep.

According to specific aspects of the present invention, the xenogeneic tumor cells are human tumor cells. According to specific aspects of the present invention, the human tumor cells are present in a sample obtained from the human, such as, but not limited to, in a blood sample, tissue sample, or sample obtained by biopsy of a human tumor.

Tumor cells obtained from a human can be administered directly to an immunodeficient QUAD mouse of the present invention or may be cultured in vitro prior to administration to the immunodeficient QUAD mouse.

As used herein, the term "tumor" refers to cells characterized by unregulated growth including, but not limited to, pre-neoplastic hyperproliferation, cancer in-situ, neoplasms, metastases and solid and non-solid tumors. Examples of tumors are those caused by cancer include, but are not limited to, lymphoma, leukemia, squamous cell cancer, small-cell lung cancer, non-small cell lung cancer, adenocarcinoma of the lung, squamous carcinoma of the lung, cancer of the peritoneum, adrenal cancer, anal cancer, bile duct cancer, bladder cancer, brain cancer, breast cancer, triple negative breast cancer, central or peripheral nervous system cancers, cervical cancer, colon cancer, colorectal cancer, endometrial cancer, esophageal cancer, gall bladder cancer, gastrointestinal cancer, glioblastoma, head and neck cancer, kidney cancer, liver cancer, nasopharyngeal cancer, nasal cavity cancer, oropharyngeal cancer, oral cavity cancer, osteosarcoma, ovarian cancer, pancreatic cancer, parathyroid cancer, pituitary cancer, prostate cancer, retinoblastoma, sarcoma, salivary gland cancer, skin cancer, small intestine cancer, stomach cancer, testicular cancer, thymus cancer, thyroid cancer, uterine cancer, vaginal cancer and vulval cancer.

The tumor cells can include BR1126, MDA-MB-231, TM1149, or BL0293 cells.

Administering the tumor cells to the immunodeficient QUAD mouse can be any method that is suitable as recognized in the art. For example, administration can include administering cells into an organ, body cavity, or blood vessel such as by injection or implantation, such as subcutaneous and/or intraperitoneal implantation. The tumor cells may be administered as a tumor mass, clumps of tumor cells or as dissociated cells.

Tumor cells can be administered by various routes, such as, but not limited to, by subcutaneous injection, intraperitoneal injection or injection into the tail vein.

Engraftment of xenogeneic tumor cells can be assessed by any of various methods, such as, but not limited to, visual inspection of the mouse for signs of tumor formation.

Any of various methods can be used to measure growth of xenogeneic tumors, including but not limited to, measurement in living mice, measurement of tumors excised from living mice or measurement of tumors in situ or excised from dead mice. Measurements can be obtained using a measuring instrument such as a caliper, measurement using one or more imaging techniques such as ultrasonography, computed tomography, positron emission tomography, fluorescence imaging, bioluminescence imaging, magnetic resonance imaging and combinations of any two or more of these or other tumor measurement methods. The number of tumor cells in a sample obtained from a mouse bearing xenogeneic tumor cells can be used to measure tumor growth, particularly for non-solid tumors. For example, the number of non-solid tumor cells in a blood sample can be assessed to obtain a measurement of growth of a non-solid tumor in a mouse.

The number of tumor cells administered is not considered limiting. A single tumor cell can expand into a detectable tumor in the genetically modified immunodeficient animals described herein. The number of administered tumor cells is generally in the range of $1,000-1\times10^6$ tumor cells, although more or fewer can be administered.

Thus, a method according to aspects of the present invention can include administering about $10^2$ (100) to about $10^7$ (10,000,000), about $10^3$ to about $10^5$, about $10^4$ to about $10^6$, about $10^5$ to about $10^7$, about $1\times10^3$ to about $1\times10^4$, about $5\times10^3$ to about $5\times10^4$, about $1\times10^4$ to about $1\times10^5$, about $5\times10^4$ to about $5\times10^5$, about $1\times10^5$ to about $1\times10^6$, about $5\times10^5$ to about $5\times10^6$, about $1\times10^6$ to about $1\times10^7$, about $2\times10^4$ to about $5\times10^5$, or about $5\times10^4$ to about $2\times10^5$ xenogeneic tumor cells, such as human tumor cells, to the immunodeficient QUAD mouse. The method can include administering at least about $1\times10^2$, about $2\times10^2$, about $3\times10^2$, about $4\times10^2$, about $5\times10^2$, about $6\times10^2$, about $7\times10^2$, about $8\times10^2$, about $9\times10^2$, about $1\times10^3$, about $2\times10^3$, about $3\times10^3$, about $4\times10^3$, about $5\times10^3$, about $6\times10^3$, about $7\times10^3$, about $8\times10^3$, about $9\times10^3$, about $1\times10^4$, about $2\times10^4$, about $3\times10^4$, about $4\times10^4$, about $5\times10^4$, about $6\times10^4$, about $7\times10^4$, about $8\times10^4$, about $9\times10^4$, about $1\times10^5$, about $2\times10^5$, about $3\times10^5$, about $4\times10^5$, about $5\times10^5$, about $6\times10^5$, about $7\times10^5$, about $8\times10^5$, about $9\times10^5$, about $1\times10^6$, about $2\times10^6$, about $3\times10^6$, about $4\times10^6$, about $5\times10^6$, about $6\times10^6$, about $7\times10^6$, about $8\times10^6$, about $9\times10^6$, or about $1\times10_7$ xenogeneic tumor cells, such as human tumor cells, to the immunodeficient QUAD mouse. The method can include administering about $1\times10^2$, about $2\times10^2$, about $3\times10^2$, about $4\times10^2$, about $5\times10^2$, about $6\times10^2$, about $7\times10^2$, about $8\times10^2$, about $9\times10^2$, about $1\times10^3$, about $2\times10^3$, about $3\times10^3$, about $4\times10^3$, about $5\times10^3$, about $6\times10^3$, about $7\times10^3$, about $8\times10^3$, about $9\times10^3$, about $1\times10^4$, about $2\times10^4$, about $3\times10^4$, about $4\times10^4$, about $5\times10^4$, about $6\times10^4$, about $7\times10^4$, about $8\times10^4$, about $9\times10^4$, about $1\times10^5$, about $2\times10^5$, about $3\times10^5$, about $4\times10^5$, about $5\times10^5$, about $6\times10^5$, about $7\times10^5$, about $8\times10^5$, about $9\times10^5$, about $1\times10^6$, about $2\times10^6$, about $3\times10^6$, about $4\times10^6$, about $5\times10^6$, about $6\times10^6$, about $7\times10^6$, about $8\times10^6$, about $9\times10^6$, or about $1\times10^7$ xenogeneic tumor cells, such as human tumor cells, to the immunodeficient QUAD mouse. Those of ordinary skill will be able to determine a number of xenogeneic tumor cells that should be administered to a specific mouse using no more than routine experimentation.

According to aspects of the present invention, xenogeneic tumor cells and xenogeneic HSC are administered to an immunodeficient QUAD mouse. The xenogeneic tumor cells and xenogeneic HSC can be administered at the same time or at different times.

According to aspects of the present invention, the tumor cells are derived from the same species as the administered HSC. According to aspects, both the tumor cells and the HSC administered to an immunodeficient QUAD mouse are human cells.

According to aspects of the present invention the administered HSC and tumor cells are human leukocyte antigen (HLA) matched (e.g., MHC Class I matched and/or MHC class II matched). HLA-matching may reduce the likelihood of a graft-versus-graft immune response against HLA cell-surface proteins. An immune response against HLA may falsely suggest that xenogeneic immune cells are successfully targeting xenogeneic cancer cells.

The administered HSC and tumor cells can include at least 2, 3, 4, 5, 6, 7, 8, 9, 10, 11, 12, 13, 14, 15, 16, 17, 18, 19, or 20 matching HLA alleles. The administered HSC and tumor cells can include at least 2, 3, 4, 5, 6, 7, or 8 matching HLA alleles selected from the alleles for HLA-A, HLA-B, HLA-C, and HLA-DRB1. Perfect HLA matching is rarely possible without genetic engineering, and perfect HLA matching may be unnecessary. Control experiments, for example, can account for any HLA-mediated graft-versus-graft immune response.

Assay Methods

Methods and immunodeficient QUAD mice provided according to aspects of the present invention have various utilities such as, in vivo testing of substances directed against human cancer.

Methods for identifying anti-tumor activity of a test substance according to aspects of the present invention include providing an immunodeficient QUAD mouse; administering xenogeneic tumor cells to the immunodeficient QUAD mouse, wherein the xenogeneic tumor cells form a solid or non-solid tumor in the immunodeficient QUAD mouse; administering a test substance to the immunodeficient QUAD mouse; assaying a response of the xenogeneic tumor and/or tumor cells to the test substance, wherein an inhibitory effect of the test substance on the tumor and/or tumor cells identifies the test substance as having anti-tumor activity.

Methods for identifying anti-tumor activity of a test substance according to aspects of the present invention include providing an immunodeficient QUAD mouse, wherein the immunodeficient QUAD mouse has engrafted xenogeneic HSC; administering xenogeneic tumor cells to the immunodeficient QUAD mouse, wherein the xenogencic tumor cells form a solid or non-solid tumor in the immunodeficient QUAD mouse; administering a test substance to the immunodeficient QUAD mouse; assaying a response of the xenogeneic tumor and/or tumor cells to the test substance, wherein an inhibitory effect of the test substance on the tumor and/or tumor cells identifies the test substance as having anti-tumor activity.

Methods for identifying anti-tumor activity of a test substance according to aspects of the present invention include providing an immunodeficient QUAD mouse, wherein the immunodeficient QUAD mouse has engrafted human HSC; administering human tumor cells to the immunodeficient QUAD mouse, wherein the human tumor cells form a solid or non-solid tumor in the immunodeficient QUAD mouse; administering a test substance to the immunodeficient QUAD mouse; assaying a response of the human tumor and/or tumor cells to the test substance, wherein an inhibitory effect of the test substance on the tumor and/or tumor cells identifies the test substance as having anti-tumor activity.

An immunodeficient QUAD mouse used in an assay for identifying anti-tumor activity of a test substance according to aspects of the present invention is an NSG-QUAD mouse, an NRG-QUAD mouse or a NOG-QUAD mouse.

The term "inhibitory effect" as used herein refers to an effect of the test substance to inhibit one or more of: tumor growth, tumor cell metabolism and tumor cell division.

Assaying a response of the xenogeneic tumor and/or tumor cells to the test substance includes comparing the response to a standard to determine the effect of the test substance on the xenogeneic tumor cells according to aspects of methods of the present invention, wherein an inhibitory effect of the test substance on the xenogeneic tumor cells identifies the test substance as an anti-tumor composition. Standards are well-known in the art and the standard used can be any appropriate standard. In one example, a standard is a compound known to have an anti-tumor effect. In a further example, non-treatment of a comparable xenogeneic tumor provides a base level indication of the tumor growth without treatment for comparison of the effect of a test substance. A standard may be a reference level of expected tumor growth previously determined in an individual comparable mouse or in a population of comparable mice and stored in a print or electronic medium for recall and comparison to an assay result.

Assay results can be analyzed using statistical analysis by any of various methods to determine whether the test substance has an inhibitory effect on a tumor, exemplified by parametric or non-parametric tests, analysis of variance, analysis of covariance, logistic regression for multivariate analysis, Fisher's exact test, the chi-square test, Student's T-test, the Mann-Whitney test, Wilcoxon signed ranks test, McNemar test, Friedman test and Page's L trend test. These and other statistical tests are well-known in the art as detailed in Hicks, CM, Research Methods for Clinical Therapists: Applied Project Design and Analysis, Churchill Livingstone (publisher); 5th Ed., 2009; and Freund, R J et al., Statistical Methods, Academic Press; 3rd Ed., 2010.

A test substance used in a method of the present invention can be any chemical entity, illustratively including a synthetic or naturally occurring compound or a combination of a synthetic or naturally occurring compound, a small organic or inorganic molecule, a protein, a peptide, a nucleic acid, a carbohydrate, an oligosaccharide, a lipid or a combination of any of these. According to aspects of the present invention, the test substance is an immunotherapeutic.

According to aspects of the present invention, a test substance is an anti-cancer agent. According to aspects of the present invention, the test substance is an anti-cancer immunotherapeutic, such as an anti-cancer antibody or antigen binding fragment thereof.

Anti-cancer agents are described, for example, in Brunton et al. (eds.), Goodman and Gilman's The Pharmacological Basis of Therapeutics, 12th Ed., Macmillan Publishing Co., 2011.

Anti-cancer agents illustratively include acivicin, aclarubicin, acodazole, acronine, adozelesin, aldesleukin, alitretinoin, allopurinol, altretamine, ambomycin, ametantrone, amifostine, aminoglutethimide, amsacrine, anastrozole, anthramycin, arsenic trioxide, asparaginase, asperlin, azacitidine, azetepa, azotomycin, batimastat, benzodepa, bicalutamide, bisantrene, bisnafide dimesylate, bizelesin, bleomycin, brequinar, bropirimine, busulfan, cactinomycin, calusterone, capecitabine, caracemide, carbetimer, carboplatin, carmustine, carubicin, carzelesin, cedefingol, celecoxib, chlorambucil, cirolemycin, cisplatin, cladribine, cobimetinib, crisnatol mesylate, cyclophosphamide, cytarabine, dacarbazine, dactinomycin, daunorubicin, decitabine, dexormaplatin, dezaguanine, dezaguanine mesylate, diaziquone, docetaxel, doxorubicin, droloxifene, dromostanolone, duazomycin, edatrexate, eflomithine, elsamitrucin, enloplatin, enpromate, epipropidine, epirubicin, erbulozole, esorubicin, estramustine, etanidazole, etoposide, etoprine, fadrozole, fazarabine, fenretinide, floxuridine, fludarabine, fluorouracil, flurocitabine, fosquidone, fostriecin, fulvestrant, gemcitabine, hydroxyurca, idarubicin, ifosfamide, ilmofosine, interleukin II (IL-2, including recombinant interleukin II or rIL2), interferon alfa-2a, interferon alfa-2b, interferon alfa-nl, interferon alfa-n3, interferon beta-Ia, interferon gamma-Ib, iproplatin, irinotecan, lanreotide, letrozole, leuprolide, liarozole, lometrexol, lomustine, losoxantrone, masoprocol, maytansine, mechlorethamine hydrochlride, megestrol, melengestrol acetate, melphalan, menogaril, mercaptopurine, methotrexate, metoprine, meturedepa, mitindomide, mitocarcin, mitocromin, mitogillin, mitomalcin, mitomycin, mitosper, mitotane, mitoxantrone, mycophenolic acid, nelarabine, nocodazole, nogalamycin, ormnaplatin, oxisuran, paclitaxel, pegaspargase, peliomycin, pentamustine, peplomycin, perfosfamide, pipobroman, piposulfan, piroxantrone hydrochloride, plicamycin, plomestane, porfimer, porfiromycin, prednimustine, procarbazine, puromycin, pyrazofurin, riboprine, rogletimide, safingol, semustine, simtrazene, sparfosate, sparsomycin, spirogermanium, spiromustine, spiroplatin, streptonigrin, streptozocin, sulofenur, talisomycin, tamoxifen, tecogalan, tegafur, teloxantrone, temoporfin, teniposide, teroxirone, testolactone, thiamiprine, thioguanine, thiotepa, tiazofurin, tirapazamine, topotecan, toremifene, trestolone, triciribine, trimetrexate, triptorelin, tubulozole, uracil mustard, uredepa, vapreotide, vemurafenib, verteporfin, vinblastine, vincristine sulfate, vindesine, vinepidine, vinglycinate, vinleurosine, vinorelbine, vinrosidine, vinzolidine, vorozole, zeniplatin, zinostatin, zoledronate, and zorubicin.

According to aspects of the present invention, an anti-cancer agent is an anti-cancer antibody. An anti-cancer antibody used can be any antibody effective to inhibit at least one type of tumor, particularly a human tumor. Anti-cancer antibodies include, but are not limited to, 3F8, 8H9, abagovomab, abituzumab, adalimumab, adecatumumab, aducanumab, afutuzumab, alacizumab pegol, alemtuzumab, amatuximab, anatumomab mafenatox, anctumab ravtansine, apolizumab, arcitumomab, ascrinvacumab, atezolizumab, bavituximab, belimumab, bevacizumab, bivatuzumab mertansine, brentuximab vedotin, brontictuzumab, cantuzumab mertansine, cantuzumab ravtansine, capromab pendetide, catumaxomab, cetuximab, citatuzumab bogatox, cixutumumab, clivatuzumab tetraxetan, coltuximab ravtansine, conatumumab, dacetuzumab, dalotuzumab, demcizumab, denintuzumab mafodotin, depatuxizumab mafodotin, durvalumab, dusigitumab, cdrecolomab, clotuzumab, cmactuzumab, emibetuzumab, enoblituzumab, enfortumab vedotin, enavatuzumab, epratuzumab, ertumaxomab, ctaracizumab, farletuzumab, ficlatuzumab, figitumumab, flanvotumab, futuximab, galiximab, ganitumab, gemtuzumab, girentuximab, glembatumumab vedotin, ibritumomab tiuxetan, igovomab, imab362, imalumab, imgatuzumab, indatuximab ravtansine, indusatumab vedotin, inebilizumab, inotuzumab ozogamicin, intetumumab, ipilimumab, iratumumab, isatuximab, labetuzumab, lexatumumab, lifastuzumab vedotin, lintuzumab, lirilumab, lorvotuzumab mertansine, lucatumumab, lumiliximab, lumretuzumab, mapatumumab, margetuximab, matuzumab, milatuzumab, mirvetuximab soravtansine, mitumomab, mogamulizumab, moxetumomab pasudotox, nacolomab tafenatox, naptumomab estafenatox, narnatumab, necitumumab, nesvacumab, nimotuzumab, nivolumab, ocaratuzumab, ofatumumab, olaratumab, onartuzumab, ontuxizumab, oregovomab, oportuzumab monatox, otlertuzumab, panitumumab, pankomab, parsatuzumab, patritumab, pembrolizumab, pemtumomab, pertuzumab, pidilizumab, pinatuzumab vedotin, polatuzumab vedotin, pritumumab, racotumomab, radretumab, ramucirumab, rilotumumab, rituximab, robatumumab, sacituzumab govitecan, samalizumab, seribantumab, sibrotuzumab, siltuximab, sofituzumab vedotin, tacatuzumab tetraxetan, tarextumab, tenatumomab, teprotumumab, tetulomab, tigatuzumab, tositumomab, tovetumab, trastuzumab, tremelimumab, tucotuzumab celmoleukin, ublituximab, utomilumab, vandortuzumab vedotin, vantictumab, vanucizumab, varlilumab, vesencumab, volociximab, vorsetuzumab mafodotin, votumumab, zalutumumab and zatuximab.

According to aspects of the present invention, a test substance is one that specifically binds one or more of: 1) a cell-surface protein such as a cluster of differentiation (CD) cell-surface molecule; 2) an intracellular protein such as a kinase; and 3) an extracellular protein such as a shed cell-surface receptor or the soluble ligand of a cell-surface receptor.

According to aspects of the present invention, a test substance is one that specifically binds a protein that is expressed by leukocytes (e.g., lymphocytes or myeloid-lineage leukocytes). In a further option, a test substance is one that specifically binds a ligand of a leukocyte. In a still further option, a test substance is one that specifically binds a molecule that is expressed by a cancer cell.

According to aspects of the present invention, a test substance is a chemotherapeutic agent or an immunotherapeutic agent. According to aspects of the present invention, a test substance can specifically binds PD-1, PD-L1, or CTLA-4. According to aspects of the present invention, a test substance can be an immune checkpoint inhibitor such as a PD-1 inhibitor, PD-L1 inhibitor, or CTLA-4 inhibitor. According to aspects of the present invention, a test substance is an immune checkpoint inhibitor selected from atezolizumab, avelumab, durvalumab, ipilimumab, nivolumab, pembrolizumab, and an antigen-binding fragment of any one of the foregoing.

The test substance can be administered by any suitable route of administration, such as, but not limited to, oral, rectal, buccal, nasal, intramuscular, vaginal, ocular, otic, subcutaneous, transdermal, intratumoral, intravenous, and intraperitoneal.

A genetically-modified, immunodeficient mouse is provided along with methods of use, wherein the mouse includes (a) a nucleotide sequence encoding human stem cell factor (hSCF); (b) a nucleotide sequence encoding human granulocyte-macrophage colony-stimulating factor (hGM-CSF); (c) a nucleotide sequence encoding human interleukin-3 (hIL-3); and (d) a nucleotide sequence encoding human colony-stimulating factor 1 (hCSF1), wherein each of the nucleotide sequences is operably linked to a promoter, and wherein the genetically-modified, immunodeficient mouse expresses hSCF, hGM-CSF, hIL-3, and hCSF1, wherein the genetically-modified, immunodeficient mouse allows engraftment of human hematopoietic stem cells along with engraftment of human-patient derived tumor xenografts and/or human tumor cell lines to enable in vivo investigation of the interactions between the human immune system and human cancer.

Embodiments of inventive compositions and methods are illustrated in the following examples. These examples are provided for illustrative purposes and are not considered limitations on the scope of inventive compositions and methods.

EXAMPLES

Example 1. Analysis of NSG-Quad Mice Having a Human Hematopoietic Stem Cell Xenograft Mice that constitutively express a transgene encoding human colony stimulating factor 1 (hCSF1) were generated in an NSG background using routine techniques and are referred to herein as "NSG-CSF1" mice. To make the NSG-CSF1 mice, a transgene encoding human CSF1 (hCSF1) is designed. Expression of hCSF1 is driven by a human cytomegalovirus promoter/enhancer sequence, and is followed by a human growth hormone cassette and a polyadenylation (polyA) sequence. The hCSF1 transgene is microinjected into fertilized C57BL/6xC3H/HeN oocytes. The resulting founders, carrying the hCSFltransgene are backcrossed to BALB/c-Prkdc$^{scid}$ mice for several generations and subsequently backcrossed to NOD.CB17-Prkdc$^{scid}$ mice for several generations. These mice are backcrossed to NOD.Cg-Prkdc$^{scid}$ Il2rg$^{tm1Wjl}$ mice, and are then intercrossed until all offspring are homozygous for the hCSF1 transgene and the IL2rg targeted mutation. These transgenic mice are bred to NOD.Cg-Prkdc$^{scid}$ Il2rg$^{tm1Wjl}$/SzJ mice (NSG mice, Jackson Laboratory Stock No. 005557) to establish the colony. Thereafter, females homozygous for Prkdc$^{scid}$, homozygous for Il2rg$^{tm1Wjl}$ and homozygous for the hCSF1 transgene were bred with males homozygous for Prkdc$^{scid}$, hemizygous for the X-linked Il2rg$^{tm1Wjl}$ and homozygous for the hCSF1 transgene.

NSG-CSF1 are maintained on the NOD.Cg-Prkdc$^{scid}$ Il2rg$^{tm1Wjl}$/SzJ mouse (Stock No. 005557) background and constitutively produce detectable serum levels of human CSF1.

NSG-SGM3 mice express human transgenes for stem cell factor (hSCF), granulocyte-macrophage-colony stimulating factor (hGM-CSF), and interleukin-3 (hIL-3). NSG-SGM3 mice contain three transgenes, human interleukin-3 (IL-3), human granulocyte/macrophage-stimulating factor (GM-CSF), and human Steel factor (SF) gene, each driven by a human cytomegalovirus promoter/enhancer sequence. To make the NSG-SGM3 mice, three separate transgenes were designed each carrying one of: the human interleukin-3 (IL-3) gene, the human granulocyte/macrophage-stimulating factor (GM-CSF) gene, or human Steel factor (SF) gene. Expression of each gene is driven by a human cytomegalovirus promoter/enhancer sequence, and is followed by a human growth hormone cassette and a polyadenylation (polyA) sequence. The three transgenes were microinjected into fertilized C57BL/6xC3H/HeN oocytes. The resulting founders, carrying all three transgenes (3GS) were backcrossed to BALB/c-Prkdc$^{scid}$ mice for several generations and subsequently backcrossed to NOD.CB17-Prkdc$^{scid}$ mice for at least 11 generations. These mice were bred to NOD.Cg-Prkdc$^{scid}$ Il2rg$^{tm1Wjl}$ mice, and were then intercrossed until all offspring were homozygous for 3GS and the IL2rg targeted mutation. These transgenic mice were bred to NOD.Cg-Prkdc$^{scid}$ Il2rg$^{tm1Wjl}$/SzJ mice (NSG mice, Jackson Laboratory Stock No. 005557) for one generation to establish the colony. Thereafter, females homozygous for Prkdc$^{scid}$, homozygous for Il2rg$^{tm1Wjl}$ and homozygous for the 3GS transgenes were bred with males homozygous for Prkdc$^{scid}$, hemizygous for the X-linked Il2rg$^{tm1Wjl}$ and homozygous for the 3GS transgenes.

NSG-SGM3 are maintained on the NOD.Cg-Prkdc$^{scid}$ Il2rg$^{tm1Wjl}$/SzJ mouse (Stock No. 005557) background and constitutively produce human IL-3, GM-CSF, and SCF. NSG-SGM3 can be obtained commercially from The Jackson Laboratory (Maine; Stock No. 013062).

NSG-Quad mice were irradiated with 50 cGy whole body radiation. NSG-SGM3 mice were irradiated with 50 cGy whole body radiation and NSG mice were irradiated with 100 cGy whole body radiation as controls. Each mouse received about 100,000 human CD34$^+$ hematopoietic stem cells from the same donor by injection. Blood cells obtained by retro-orbital bleeding at 10 weeks post-engraftment were assessed by flow cytometry for mouse CD45, human CD45, human CD20, human CD3, human CD33, human CD14, and human CD56 (FIG. 1A-F). Live cells were gated using LIVE/DEAD® (ThermFisher Scientific).

Figure 1C:
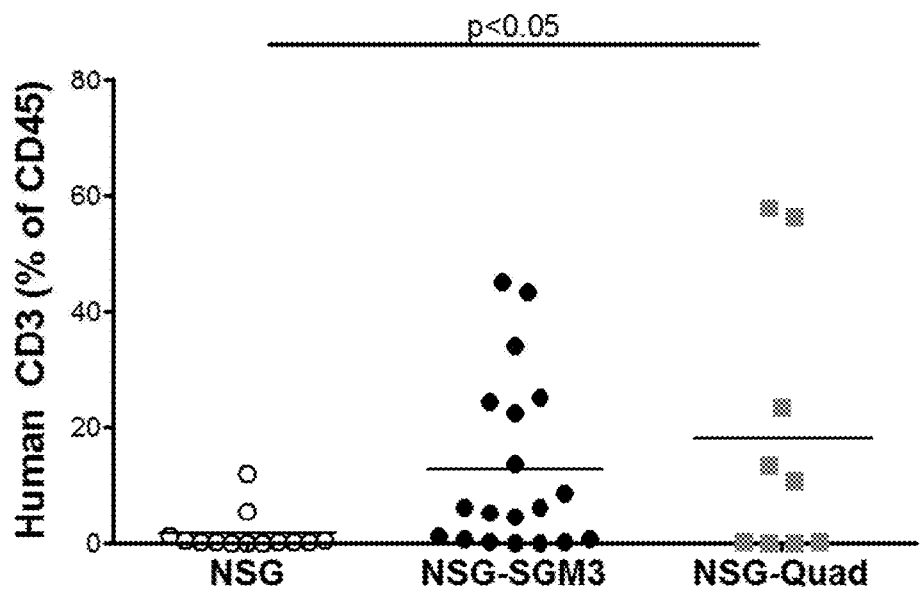
FIG. 1C is a chart depicting percentages of flow-cytometry-gated blood cells expressing human CD3 as a percentage of CD45-positive blood cells in samples from NSG mice, NSG-SGM3 mice and NSG-QUAD mice 10-weeks after administration of 100,000 human CD34$^+$ hematopoietic stem cells.
Figure 1D:
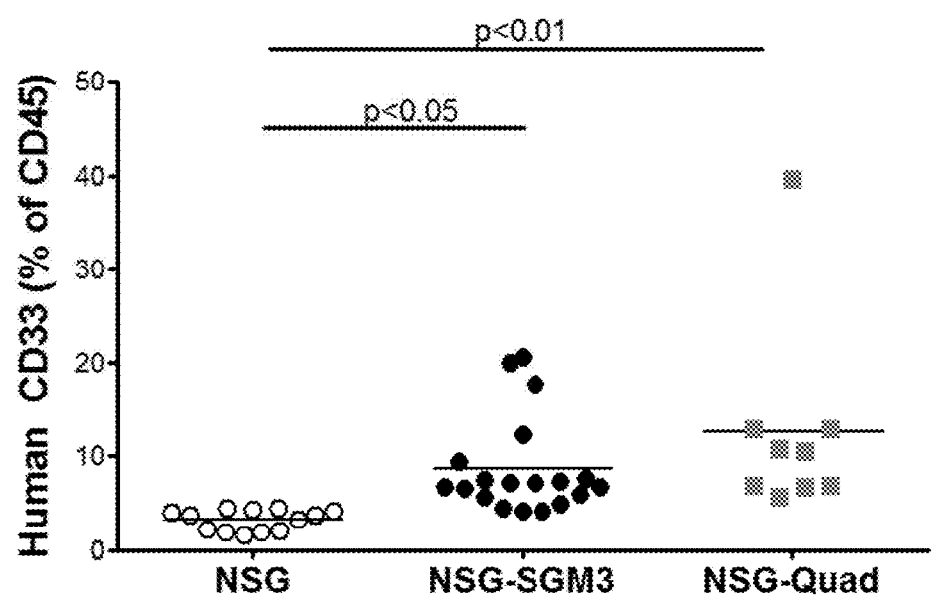
FIG. 1D is a chart depicting percentages of flow-cytometry-gated blood cells expressing human CD33 as a percentage of CD45-positive blood cells in samples from NSG mice, NSG-SGM3 mice and NSG-QUAD mice 10-weeks after administration of 100,000 human CD34$^+$ hematopoietic stem cells.
Figure 1E:
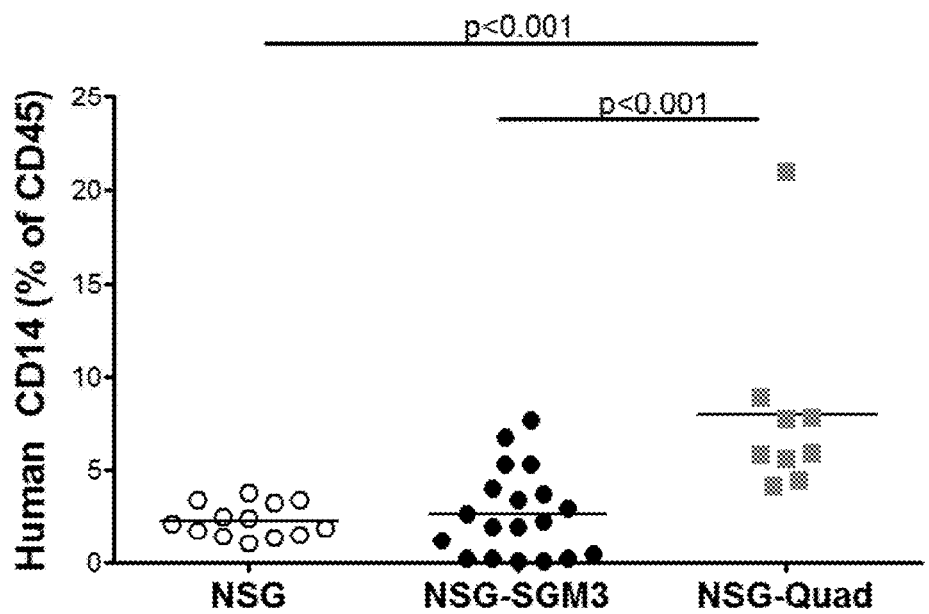
FIG. 1E is a chart depicting percentages of flow-cytometry-gated blood cells expressing human CD14 as a percentage of CD45-positive blood cells in samples from NSG mice, NSG-SGM3 mice and NSG-QUAD mice 10-weeks after administration of 100,000 human CD34$^+$ hematopoietic stem cells.
Figure 1F:
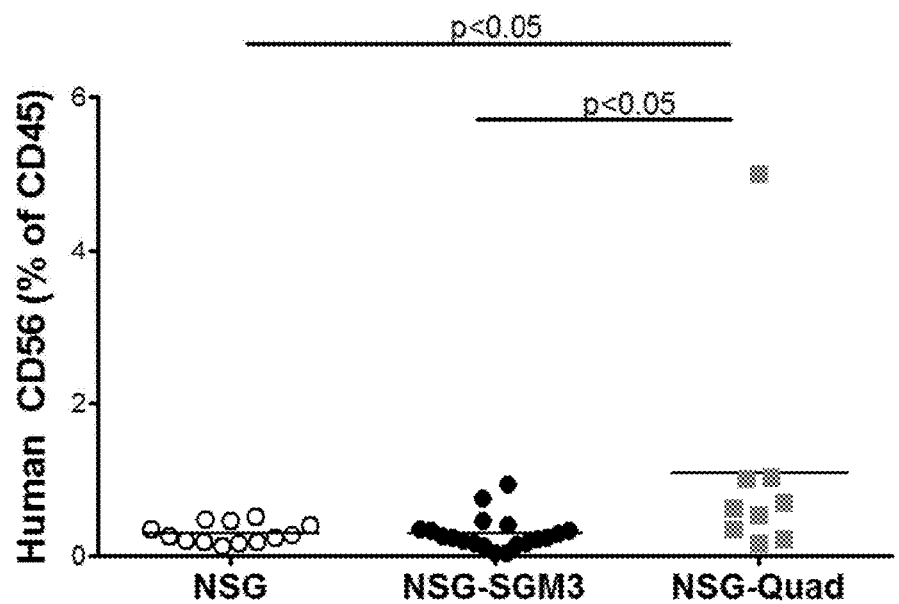
FIG. 1F is a chart depicting percentages of flow-cytometry-gated blood cells expressing human CD56 as a percentage of CD45-positive blood cells in samples from NSG mice, NSG-SGM3 mice and NSG-QUAD mice 10-weeks after administration of 100,000 human CD34$^+$ hematopoietic stem cells.
Figure 2A:
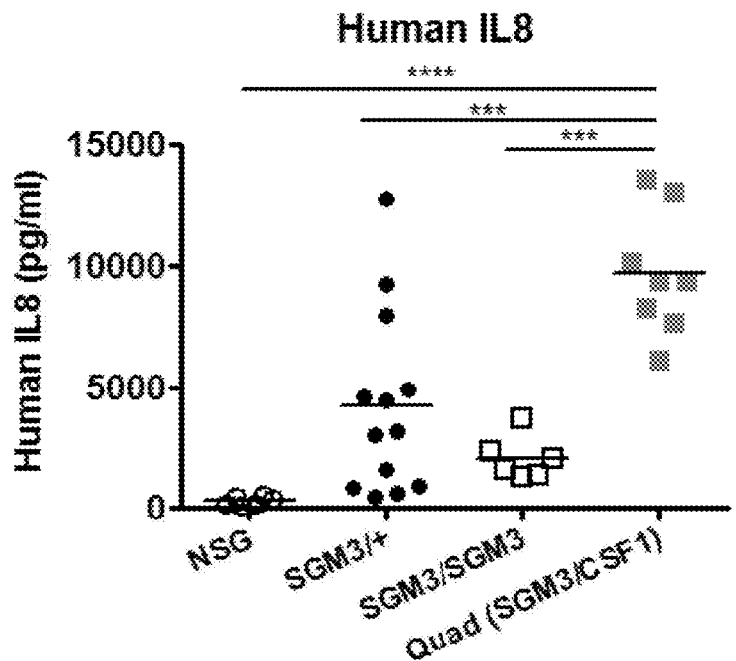
FIG. 2A is a chart depicting the concentration of human IL8 in serum samples from NSG mice, NSG-SGM3/+ mice, NSG-SGM3/SGM3, and NSG-QUAD mice which were administered 100,000 human CD34$^+$ hematopoietic stem cells followed by 0.15 µg intravenous lipopolysaccharide 10-weeks later. The serum samples were obtained 6 hours after administration of the lipopolysaccharide and the human IL8 was measured by bead-based immunoassay.
Figure 2B:
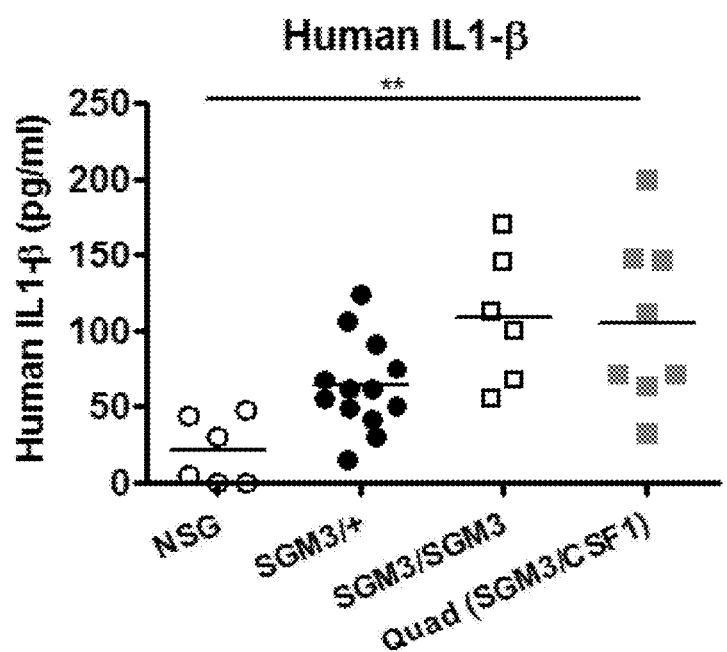
FIG. 2B is a chart depicting the concentration of human IL1-β in serum samples from NSG mice, NSG-SGM3/+ mice, NSG-SGM3/SGM3, and NSG-QUAD mice which were administered 100,000 human CD34$^+$ hematopoietic stem cells followed by 0.15 µg intravenous lipopolysaccharide 10-weeks later. The serum samples were obtained 6 hours after administration of the lipopolysaccharide and the human IL1-β was measured by bead-based immunoassay.
Figure 2C:
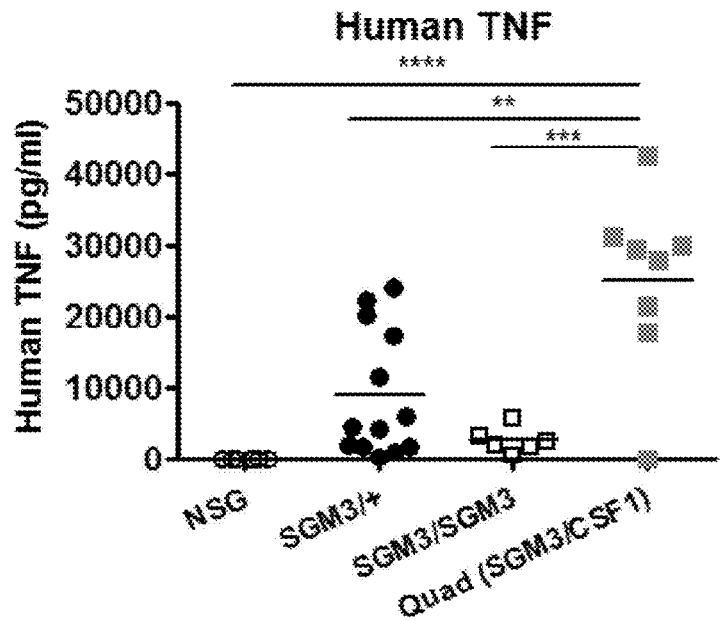
FIG. 2C is a chart depicting the concentration of human TNF in serum samples from NSG mice, NSG-SGM3/+ mice, NSG-SGM3/SGM3, and NSG-QUAD mice which were administered 100,000 human CD34$^+$ hematopoietic stem cells followed by 0.15 µg intravenous lipopolysaccharide 10-weeks later. The serum samples were obtained 6 hours after administration of the lipopolysaccharide and the human TNF was measured by bead-based immunoassay.
Figure 2D:
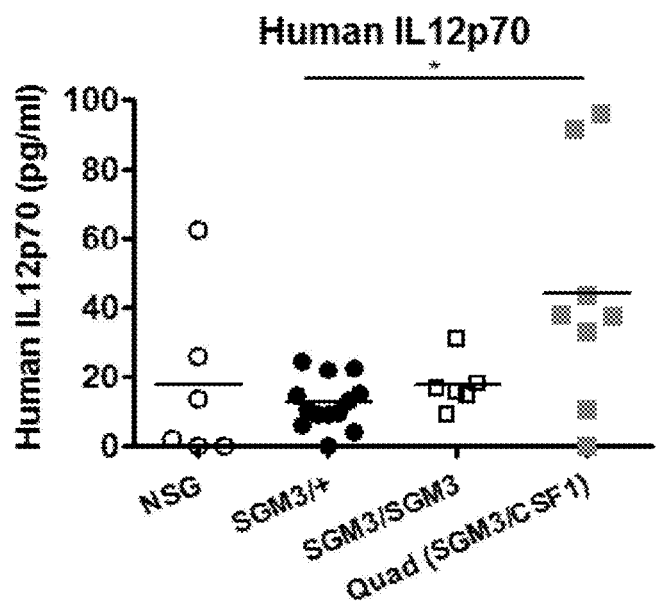
FIG. 2D is a chart depicting the concentration of human IL12p70 in serum samples from NSG mice, NSG-SGM3/+ mice, NSG-SGM3/SGM3, and NSG-QUAD mice which were administered 100,000 human CD34$^+$ hematopoietic stem cells followed by 0.15 µg intravenous lipopolysaccharide 10-weeks later. The serum samples were obtained 6 hours after administration of the lipopolysaccharide and the human IL12p70 was measured by bead-based immunoassay.
Figure 2E:
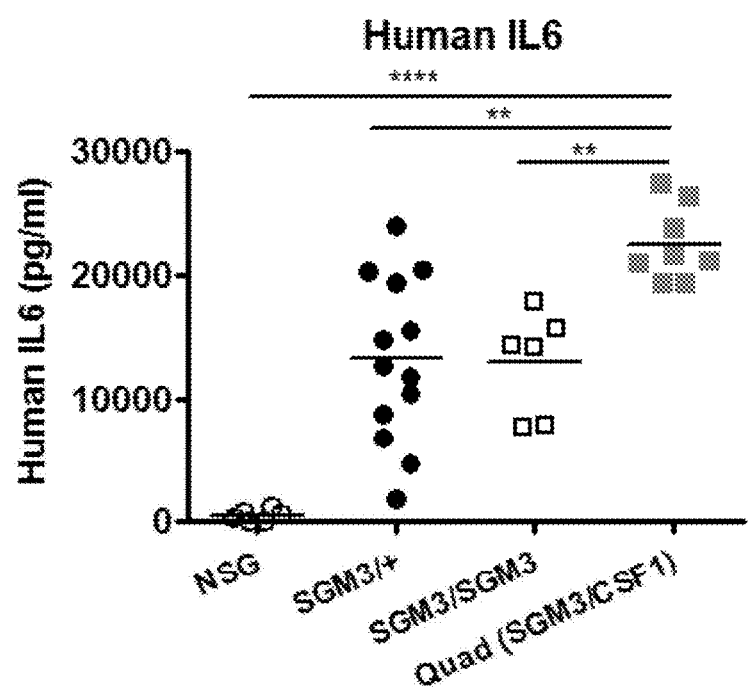
FIG. 2E is a chart depicting the concentration of human IL6 in serum samples from NSG mice, NSG-SGM3/+ mice, NSG-SGM3/SGM3, and NSG-QUAD mice which were administered 100,000 human CD34$^+$ hematopoietic stem cells followed by 0.15 µg intravenous lipopolysaccharide 10-weeks later. The serum samples were obtained 6 hours after administration of the lipopolysaccharide and the human IL6 was measured by bead-based immunoassay.

NSG-Quad mice displayed fewer numbers of human CD20$^+$ cells, increased numbers of human CD3$^+$ cells, CD33$^+$ cells, CD14$^+$ cells, and CD56$^+$ cells as a proportion of human CD45$^+$ cells relative to NSG mice, which suggests that NSG-Quad mice are better able to differentiate human hematopoietic progenitor cells into T-lymphocytes, macrophages, and natural killer cells than NSG mice (FIG. 1B-F). NSG-Quad mice displayed increased numbers of human CD14$^+$ cells and CD56$^+$ cells as a proportion of human CD45$^+$ cells relative to NSG-SGM3 mice, which suggests that NSG-Quad mice are better able to differentiate human hematopoietic progenitor cells into macrophages (myeloid lineage) and natural killer cells (lymphoid lineage) than NSG-SGM3 mice (FIG. 1E-F). NSG-Quad mice trended toward increased human CD3$^+$ cell counts and increased human CD33$^+$ cell counts as a proportion of human CD45$^+$ cells relative to NSG-SGM3 mice, although these trends did not display statistical significance (FIG. 1C-D). The trend toward increased human CD3+ cell counts nevertheless suggests that the addition of CSF1, which is believed to be a myeloid-lineage cytokine, to the NSG-SGM3 mouse had an effect on lymphoid-lineage cells.

Example 2. Immune Function of NSG-Quad Mice Having a Human Hematopoietic Stem Cell Xenograft NSG-Quad mice, NSG-SGM3 hemizygous mice, NSG-SGM3 homozygous mice, and NSG mice engrafted with human CD34+ cells as described in Example 1 were administered an intravenous injection of 0.15 µg lipopolysaccharide (LPS) 10-weeks post xenograft. Scrum was collected 6 hours after the LPS challenge, and human cytokine concentrations were determined using the BD™ Cytometric Bead Array (BD Biosciences). The NSG-Quad mice displayed increased concentrations of macrophage-secreted cytokines relative to NSG-SGM3 hemizygous mice, NSG-SGM3 homozygous mice, and NSG mice (FIG. 2A-E).

Example 3. Tumor Growth in NSG-Quad Mice

Figure 3A:
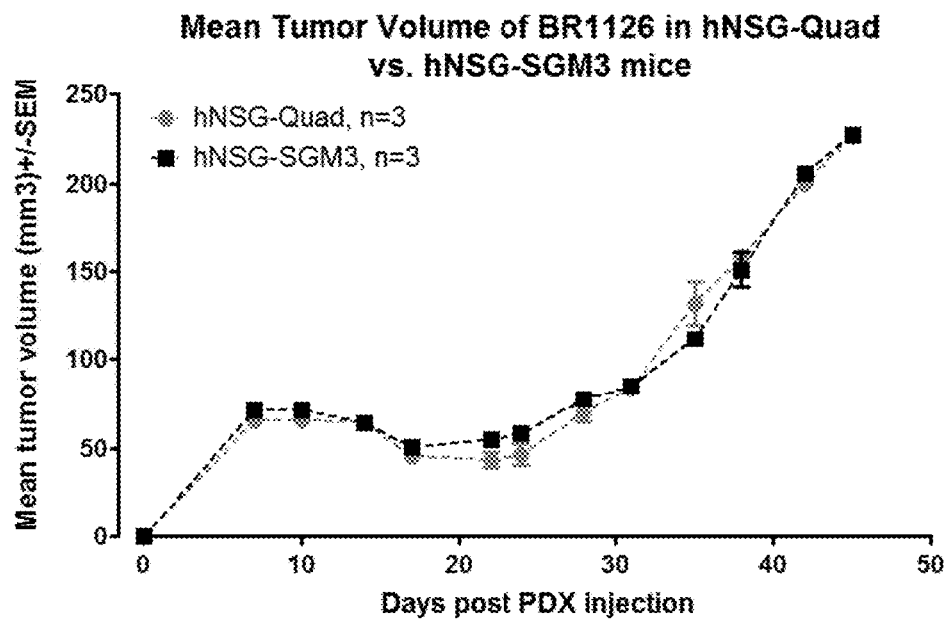
FIG. 3A is a graph depicting the mean tumor volume of tumors formed by a patient-derived xenograft (PDX) of human BR1126 breast cancer cells in NSG-QUAD mice (also called hNSG-Quad mice) compared to the mean tumor volume of tumors formed by a PDX of human BR1126 breast cancer cells NSG-SGM3 mice (also called hNSG-SGM3 mice).
Figure 3B:
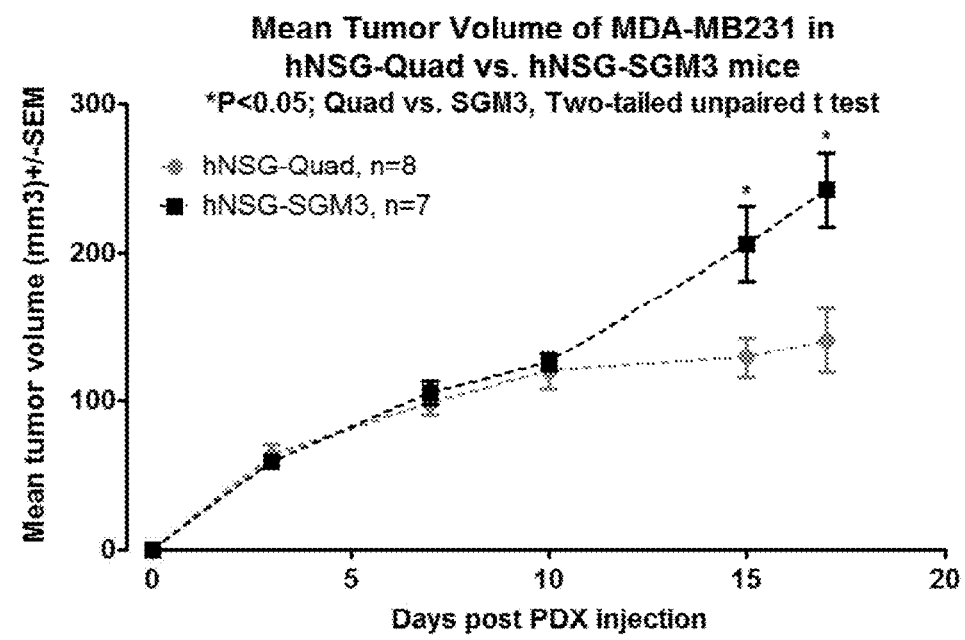
FIG. 3B is a graph depicting the mean tumor volume of tumors formed by a PDX of human MDA-MB231 breast cancer cells in NSG-QUAD mice compared to the mean tumor volume of tumors formed by a PDX of human MDA-MB231 breast cancer cells NSG-SGM3 mice.
Figure 3C:
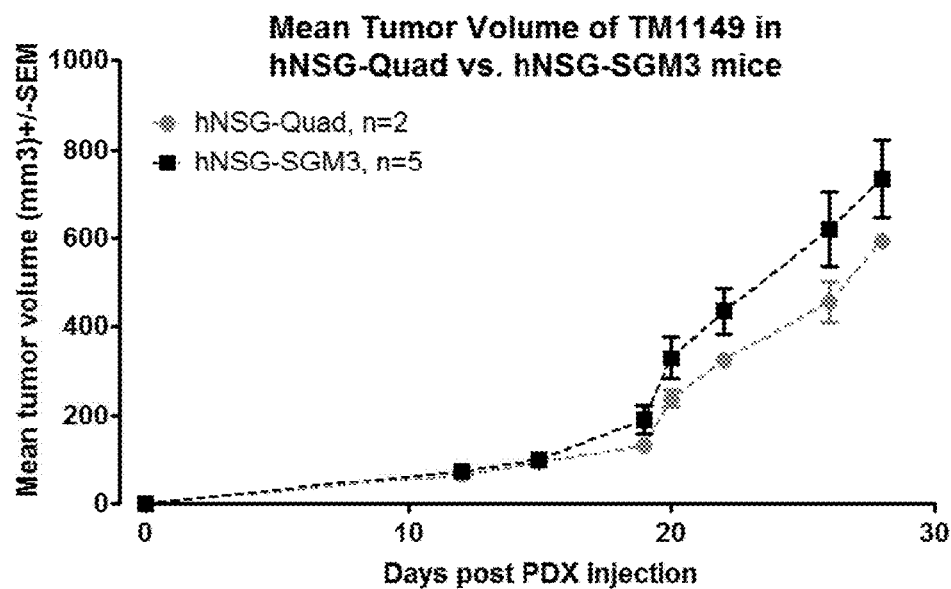
FIG. 3C is a graph depicting the mean tumor volume of tumors formed by a PDX of human TM1149 breast cancer cells in NSG-QUAD mice compared to the mean tumor volume of tumors formed by a PDX of human TM1149 breast cancer cells in NSG-SGM3 mice.
Figure 3D:
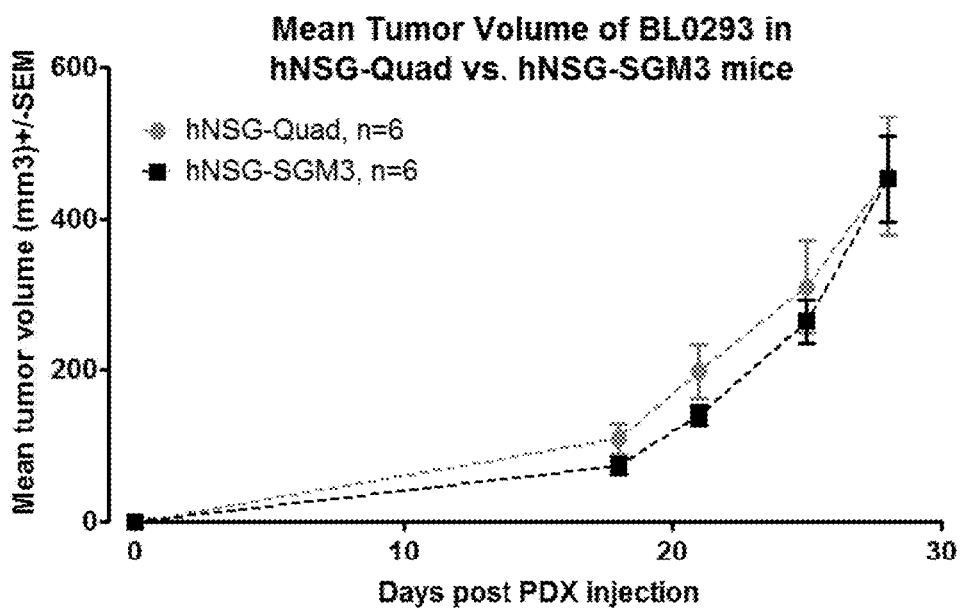
FIG. 3D is a graph depicting the mean tumor volume of tumors formed by a PDX of human BL0293 bladder cancer cells in NSG-QUAD mice compared to the mean tumor volume of tumors formed by a PDX of human BL0293 bladder cancer cells in NSG-SGM3 mice.

BR1126, MDA-MB-231, TM1149, and BL0293 tumor cells were separately implanted subcutaneously into NSG-Quad and NSG-SGM3 mice at 7-12 weeks post-CD34+-cell engraftment (see Example 1). Tumor sizes were measured with calipers. The BR1126, TM1149, and BL0293 tumors displayed similar growth in both the NSG-Quad and NSG-SGM3 mice (FIG. 3A, 3C, 3D). The NSG-Quad mice displayed significantly smaller tumors day 15 after implantation with MDA-MB-231 tumor cells (FIG. 3B).

Figure 4A:
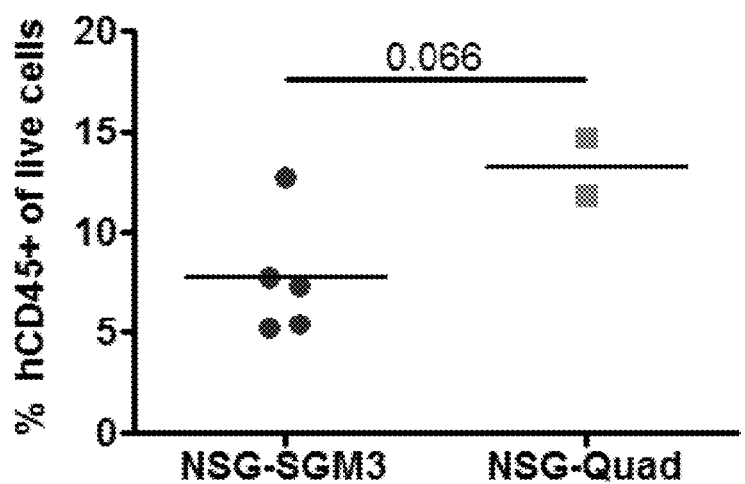
FIG. 4A is a chart showing characteristics of blood cells obtained from NSG-SGM3 and NSG-Quad mice to which 100,000 human CD34$^+$ hematopoietic stem cells were administered followed by a subcutaneous TM1149 xenograft 7-12 weeks later. PDX tumors harvested 17 weeks after xenograft administration were analyzed by flow cytometry and the percent of human CD45-positive (hCD45$^+$) in the population of total live cells in the sample is shown.
Figure 4B:
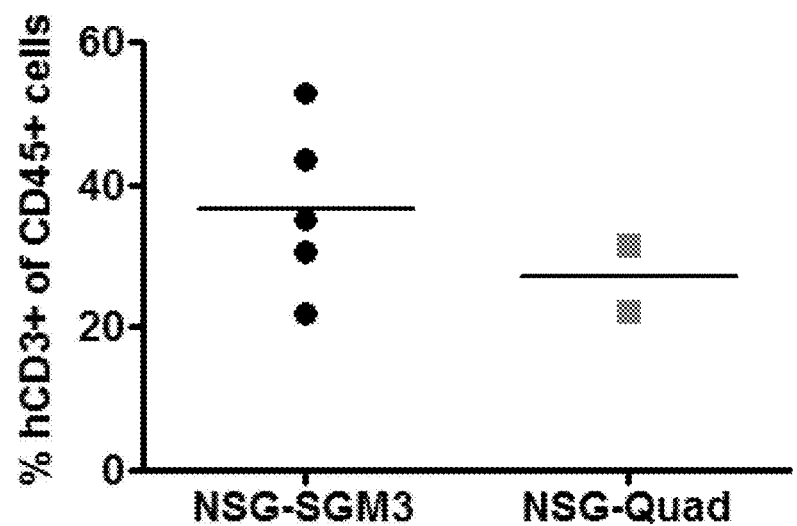
FIG. 4B is a chart showing characteristics of blood cells obtained from NSG-SGM3 and NSG-Quad mice to which 100,000 human CD34$^+$ hematopoietic stem cells were administered followed by a subcutaneous TM1149 xenograft 7-12 weeks later. PDX tumors harvested 17 weeks after xenograft administration were analyzed by flow cytometry and the percent of human CD3-positive (hCD3$^+$) in the population of CD45$^+$ cells in the sample is shown.
Figure 4C:
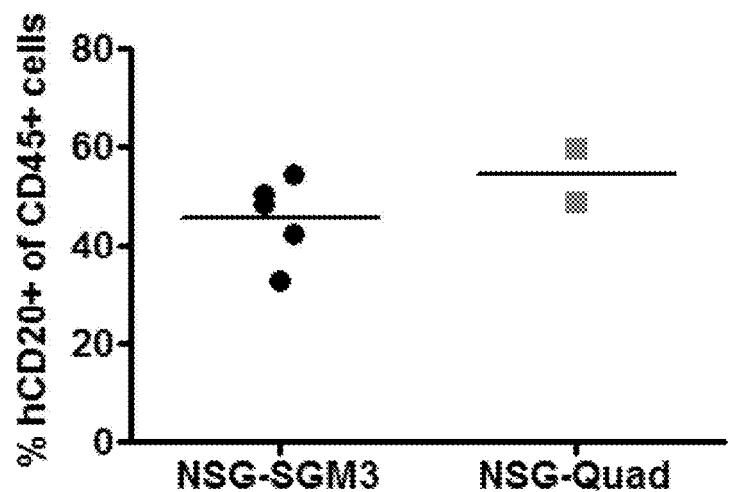
FIG. 4C is a chart showing characteristics of blood cells obtained from NSG-SGM3 and NSG-Quad mice to which 100,000 human CD34$^+$ hematopoietic stem cells were administered followed by a subcutaneous TM1149 xenograft 7-12 weeks later. PDX tumors harvested 17 weeks after xenograft administration were analyzed by flow cytometry and the percent of human CD20-positive (hCD20$^+$) in the population of CD45$^+$ cells in the sample is shown.
Figure 4D:
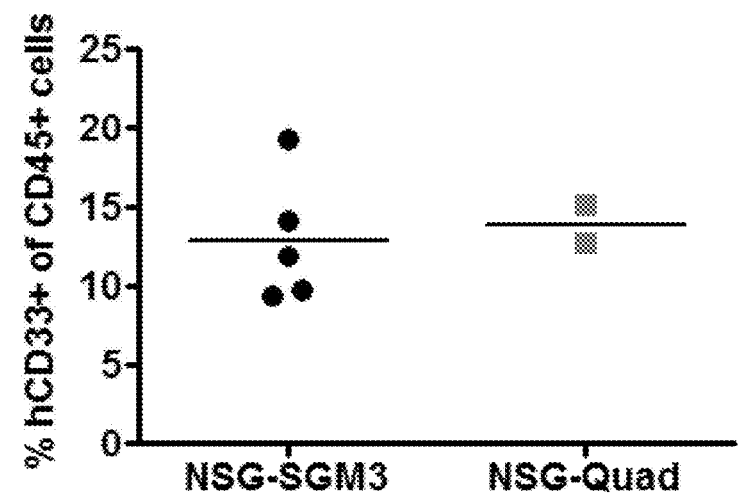
FIG. 4D is a chart showing characteristics of blood cells obtained from NSG-SGM3 and NSG-Quad mice to which 100,000 human CD34$^+$ hematopoietic stem cells were administered followed by a subcutaneous TM1149 xenograft 7-12 weeks later. PDX tumors harvested 17 weeks after xenograft administration were analyzed by flow cytometry and the percent of human CD33-positive (hCD33$^+$) in the population of CD45$^+$ cells in the sample is shown.
Figure 4E:
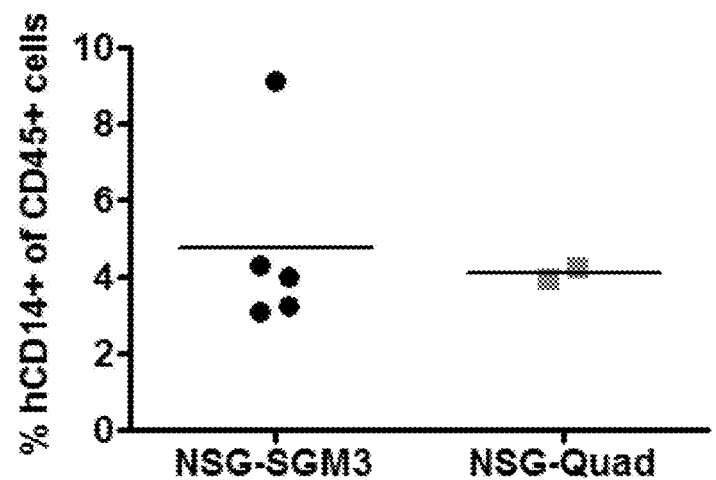
FIG. 4E is a chart showing characteristics of blood cells obtained from NSG-SGM3 and NSG-Quad mice to which 100,000 human CD34$^+$ hematopoietic stem cells were administered followed by a subcutaneous TM1149 xenograft 7-12 weeks later. PDX tumors harvested 17 weeks after xenograft administration were analyzed by flow cytometry and the percent of human CD14-positive (hCD14$^+$) in the population of CD45$^+$ cells in the sample is shown.
Figure 4F:
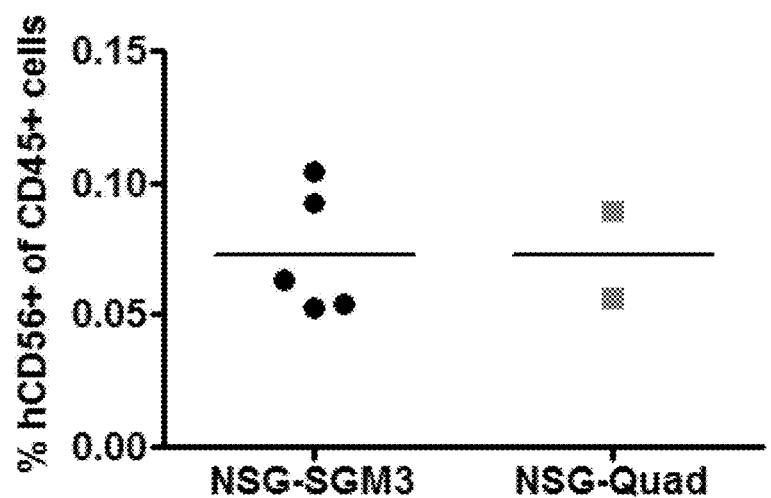
FIG. 4F is a chart showing characteristics of blood cells obtained from NSG-SGM3 and NSG-Quad mice to which 100,000 human CD34$^+$ hematopoietic stem cells were administered followed by a subcutaneous TM1149 xenograft 7-12 weeks later. PDX tumors harvested 17 weeks after xenograft administration were analyzed by flow cytometry and the percent of human CD56-positive (hCD56$^+$) in the population of CD45$^+$ cells in the sample is shown.

Human TM1149 (breast cancer) tumors were harvested from NSG-Quad and NSG-SGM3 mice at 17-weeks post tumor-cell engraftment, and cells were analyzed by flow cytometry for mouse CD45, human CD45, human CD20, human CD3, human CD33, human CD14, and human CD56 (FIG. 4A-F). Live cells were gated using LIVE/DEAD® (ThermoFisher Scientific). NSG-Quad displayed significantly more intratumoral leukocytes than NSG-SGM3 mice (FIG. 4A). Interestingly, the NSG-Quad mice trended toward increased human CD20+ cell counts, although this trend did not display statistical significance (FIG. 4C).

Figure 5:
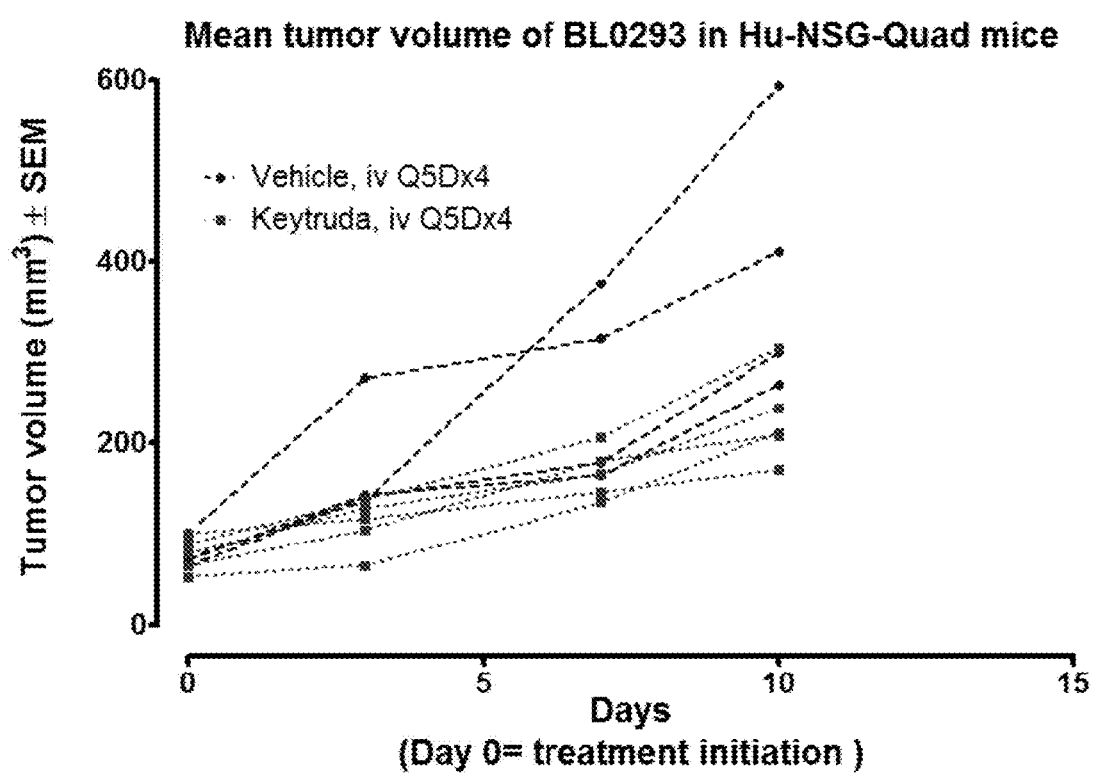
FIG. 5 is a graph comparing tumor volumes for NSG-Quad mice (Hu-NSG-Quad mice) that have human CD34$^+$ hematopoietic stem cell xenografts and BL0293 patient-derived xenografts and received injections with either pembrolizumab (Keytruda®) or vehicle.

NSG-Quad mice xenografted with human BL0293 tumor cells (bladder cancer cells) were grouped when tumors reached 60-100 mm³, and mice were then administered intravenous pembrolizumab at 10 mg/kg on day 0 followed by 5 mg/kg on days 5, 10, and 15. Tumor sizes were measured by calipers. Pembrolizumab reduced tumor growth rates in NSG-Quad mice (FIG. 5).

FIGURES

FIG. 1 consists of 6 panels, labeled FIG. 1A, FIG. 1B, FIG. 1C, FIG. 1D, FIG. 1E, and FIG. 1F. Each of FIGS. 1A, 1B, 1C, 1D, 1E, and 1F is a chart depicting percentages of flow-cytometry-gated blood cells observed in mice. Each data point corresponds to a single mouse. The x-axis labels identify three mouse strains, NSG, NSG-SGM3, and NSG-Quad, each of which is described herein. The y-axis identifies percentages of gated cells. NSG, NSG-SGM3, and NSG-Quad mice were each administered 100,000 human CD34+ hematopoietic stem cells, and blood cells were collected for flow cytometry analysis by retro-orbital bleeds 10-weeks post-engraftment. Statistically significant results are shown as p-values. The NSG-Quad mice displayed statistically significant increases in the relative number of human CD14+ cells (macrophages) and human CD56+ cells (natural killer cells) relative to NSG-SGM3 mice. Additionally, NSG-Quad mice trended toward increased human CD3+ cells (T-lymphocytes) relative to NSG-SGM3 mice, but this observation did not achieve statistical significance.

FIG. 2 consists of 5 panels, labeled FIG. 2A, FIG. 2B, FIG. 2C, FIG. 2D, and FIG. 2E. Each of FIGS. 2A, 2B, 2C, 2D, and 2E is a chart depicting the concentration of cytokines observed in mouse serum. Each data point corresponds to a single mouse. The x-axis labels identify four mouse strains, NSG, NSG-SGM3/+, NSG-SGM3/SGM3, and NSG-Quad, each of which is described herein. The y-axis identifies concentrations of cytokines. NSG, NSG-SGM3/+, NSG-SGM3/SGM3, and NSG-Quad mice were each administered 100,000 human CD34+ hematopoietic stem cells followed by 0.15 µg intravenous lipopolysaccharide 10-weeks later. Scrum cytokine concentrations were measured 6 hours after lipopolysaccharide administration using the BD™ Cytometric Bead Array for macrophage-associated cytokines. NSG-Quad mice, which constitutively express the human macrophage differentiation cytokine hCSF1, displayed elevated concentrations of macrophage-associated cytokines relative to control animals.

FIG. 3 consists of 6 panels, labeled FIG. 3A, FIG. 3B, FIG. 3C, and FIG. 3D. Each of FIGS. 3A, 3B, 3C, and 3D is a graph depicting the average tumor volume of mice having patient-derived xenografts (PDX). Each data point corresponds to an average tumor volume observed in a group of mice at a specific time-point. Circles (•) correspond to the NSG-Quad group of mice and squares (■) correspond to the NSG-SGM3 group. The x-axis identifies the number of days after a mouse received a patient-derived xenograft. The y-axis identifies the average tumor volume in mm³. Error bars correspond to standard error. Each patient-derived xenograft displayed similar growth in the NSG-Quad group and the NSG-SGM3 group except for the human MDA-MB-231 xenograft, which displayed significantly less growth in the NSG-Quad group relative to the NSG-SGM3 group beginning at day 15 post-engraftment.

FIG. 4 consists of 6 panels, labeled FIG. 4A, FIG. 4B, FIG. 4C, FIG. 4D, FIG. 4E, and FIG. 4F. Each of FIGS. 4A, 4B, 4C, 4D, 4E, and 4F is a chart depicting percentages of flow-cytometry-gated intratumor leukocytes observed in mice. Each data point corresponds to a single mouse. The x-axis labels identify two mouse strains, NSG-SGM3 and NSG-Quad, each of which is described herein. The y-axis identifies percentages of gated cells. NSG-SGM3 and NSG-Quad mice were each administered 100,000 human CD34+ hematopoietic stem cells followed by a subcutaneous TM1149 xenograft 7-12 weeks later. Tumors were harvested 17 weeks after the TM1149 xenograft and analyzed by flow cytometry. Statistically significant results are shown as p-values. NSG-Quad mice displayed a statistically significant increase in total human CD45+ cells (leukocytes) relative to NSG-SGM3 mice, which suggests that NSG-Quad mice may be superior to NSG-SGM3 mice for studying tumor-infiltrating lymphocyte-dependent cancer immunotherapies. NSG-Quad mice trended toward increased numbers of human CD3+ cells (T-lymphocytes) relative to NSG-SGM3 mice, but this observation did not display statistical significance.

FIG. 5 is a graph depicting tumor volumes for NSG-Quad mice that have human CD34+ hematopoietic stem cell xenografts and BL0293 patient-derived xenografts and receiving either pembrolizumab (Keytruda®) or vehicle. Each data point corresponds to a single mouse at a specific time-point. Circles (•) correspond to vehicle-treated mice and squares (■) correspond to pembrolizumab-treated mice. The x-axis identifies the number of days after a mouse began receiving pembrolizumab or vehicle. The y-axis identifies the average tumor volume in mm³. NSG-Quad mice treated with pembrolizumab displayed slower tumor growth on average than mice receiving vehicle.

All patents and publications mentioned in this specification are incorporated herein by reference to the same extent as if each individual publication was specifically and individually indicated to be incorporated by reference.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

The mice and methods described herein are presently representative of preferred embodiments, exemplary, and not intended as limitations on the scope of the invention. Modifications thereto and additional uses will occur to those skilled in the art. Such modifications and uses can be made without departing from the scope of the invention as set forth in the claims.

ITEMS

Item 1. A genetically-modified, immunodeficient mouse, comprising: (a) a nucleotide sequence encoding human stem cell factor (hSCF); (b) a nucleotide sequence encoding human granulocyte-macrophage colony-stimulating factor (hGM-CSF); (c) a nucleotide sequence encoding human interleukin-3 (hIL-3); and (d) a nucleotide sequence encoding human colony-stimulating factor 1 (hCSF1), wherein each of the nucleotide sequences is operably linked to a promoter, and wherein the genetically-modified, immunodeficient mouse expresses hSCF, hGM-CSF, hIL-3, and hCSF1.

Item 2. The genetically-modified, immunodeficient mouse of item 1, wherein the mouse is a genetically modified NOD.Cg-Prkdc$^{scid}$ Il2rg$^{tm1Wjl}$/SzJ (NSG) mouse; a genetically modified NOD.Cg-Rag1$^{tm1Mom}$ Il2rg$^{tm1Wjl}$/SzJ (NRG) mouse or a genetically modified NOD.Cg-Prkdc$^{scid}$ Il2rg$^{tm1Sug}$/JicTac (NOG) mouse.

Item 3. The genetically-modified, immunodeficient mouse of any one of the preceding items, wherein any one or more of the nucleotide sequences encoding hSCF, hGM-CSF, hIL-3, or hCSF1 is operably-linked to a constitutive promoter.

Item 4. The genetically-modified, immunodeficient mouse of any one of the preceding items, further comprising a human hematopoietic stem cell.

Item 5. The genetically-modified, immunodeficient mouse of any one of the preceding items, wherein the mouse comprises a differentiated human hematopoietic stem cell selected from the group consisting of a human myeloid progenitor cell, a human lymphoid progenitor cell, a human CD33$^+$ myeloid cell, a human mast cell, a human monocyte, a human macrophage, human myeloid dendritic cell, a human B cell, a human plasma cell, a human T cell, a human T helper cell, a human cytotoxic T cell, a human Treg cell, and a human natural killer cell.

Item 6. The genetically-modified, immunodeficient mouse of any one of the preceding items, wherein the mouse comprises a human leukocyte selected from the group consisting of CD45$^+$, CD20$^+$, CD20$^+$CD45$^+$, CD3$^+$, CD3$^+$CD45$^+$, CD33$^+$, CD33$^+$CD45$^+$, CD14$^+$, CD14$^+$CD45$^+$, CD56$^+$, and CD56$^+$CD45$^+$ leukocyte.

Item 7. The genetically-modified, immunodeficient mouse of item 6, wherein said mouse comprises, in the absence of an immunological challenge one, two, three or all of: at least about 20% of the human CD45$^+$ leukocytes of the mouse are CD3$^+$CD45$^+$ leukocytes; at least about 10% of the human CD45$^+$ leukocytes of the mouse are CD33$^+$CD45$^+$ leukocytes; at least about 5% of the human CD45$^+$ leukocytes of the mouse are CD14$^+$CD45$^+$ leukocytes; at least about 0.5% of the human CD45$^+$ leukocytes of the mouse are CD56$^+$CD45$^+$ leukocytes.

Item 8. The genetically-modified, immunodeficient mouse of any one of items 4 to 7, wherein the mouse expresses a human cytokine selected from the group consisting of human interleukin-8, human interleukin-1ß, human tumor-necrosis factor, human interleukin-12p70, and human interleukin-6.

Item 9. The genetically-modified, immunodeficient mouse of any one of the preceding items, further comprising a human xenograft comprising a human tumor cell.

Item 10. A method of making a genetically-modified, immunodeficient humanized mouse model, comprising: providing a genetically-modified, immunodeficient mouse according to any one of items 1 to 3; and administering human hematopoietic stem cells to the genetically-modified, immunodeficient mouse.

Item 11. The method of item 10, further comprising the step of: conditioning the genetically-modified, immunodeficient mouse to reduce mouse hematopoietic cells of the mouse prior to administering human hematopoietic stem cells.

Item 12. The method of item 11, wherein the conditioning step comprises irradiating the genetically-modified, immunodeficient mouse and/or administering a radiomimetic drug to the genetically-modified, immunodeficient mouse.

Item 13. The method of any one of items 10 to 12, further comprising the step of: administering a human xenograft comprising a human tumor cell to the genetically-modified, immunodeficient mouse.

Item 14. The method of item 13, wherein the human hematopoietic stem cell and the human tumor cell comprise at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, or at least 20 matching HLA alleles.

Item 15. A method of identifying anti-tumor activity of a test substance, comprising: providing a genetically-modified, immunodeficient mouse according to any one of items 1 to 8; administering a human tumor cell to the genetically-modified, immunodeficient mouse, wherein the human tumor cell form a solid or non-solid tumor in the genetically-modified, immunodeficient mouse; administering a test substance to the genetically-modified, immunodeficient mouse; and assaying a response of the solid or non-solid tumor to the test substance, wherein an inhibitory effect of the test substance on the tumor and/or tumor cells identifies the test substance as having anti-tumor activity Item 16. The method of item 15, further comprising comparing the response to a standard to determine the effect of the test substance on the xenogeneic tumor cell, wherein an inhibitory effect of the test substance on the xenogeneic tumor cell identifies the test substance as having anti-tumor activity.

Item 17. The method of item 15 or 16, wherein the test substance is an immunotherapeutic agent.

Item 18. The method of any one of items 15 to 17, wherein the test substance is an immune checkpoint inhibitor.

Item 19. The method of item 18, wherein the immune checkpoint inhibitor is a PD-1 inhibitor, PD-L1 inhibitor, or CTLA-4 inhibitor.

Item 20. The method of item 18 or 19, wherein the immune checkpoint inhibitor is atezolizumab, avelumab, durvalumab, ipilimumab, nivolumab, or pembrolizumab, or the immune checkpoint inhibitor comprises an antigen-binding fragment of any one of the foregoing.

Item 21. The method of any of items 15 to 20, wherein the test substance is an antibody.

Item 22. The method of any of items 15 to 21, wherein the test substance is an anti-cancer agent.

Item 23. A genetically-modified, immunodeficient mouse substantially as described or shown herein.

Item 24. A method of making a genetically-modified, immunodeficient humanized mouse model substantially as described or shown herein.

Item 25. A method of identifying anti-tumor activity of a test substance substantially as described or shown herein.

Sequences

```
SEQ ID NO: 1:
Homo sapiens colony stimulating factor 1 (CSF1), transcript
variant 1 encoding isoform a (based on NM_000757.5), 1662 nucleotides
ATGACCGCGCCGGGCGCCGCCGGGCGCTGCCCTCCCACGACATGGCTGGGCTCCCTGCT

GTTGTTGGTCTGTCTCCTGGCGAGCAGGAGTATCACCGAGGAGGTGTCGGAGTACTGTA

GCCACATGATTGGGAGTGGACACCTGCAGTCTCTGCAGCGGCTGATTGACAGTCAGATG

GAGACCTCGTGCCAAATTACATTTGAGTTTGTAGACCAGGAACAGTTGAAAGATCCAGT

GTGCTACCTTAAGAAGGCATTTCTCCTGGTACAAGACATAATGGAGGACACCATGCGCT

TCAGAGATAACACCCCCAATGCCATCGCCATTGTGCAGCTGCAGGAACTCTCTTTGAGG

CTGAAGAGCTGCTTCACCAAGGATTATGAAGAGCATGACAAGGCCTGCGTCCGAACTTT

CTATGAGACACCTCTCCAGTTGCTGGAGAAGGTCAAGAATGTCTTTAATGAAACAAAGA

ATCTCCTTGACAAGGACTGGAATATTTTCAGCAAGAACTGCAACAACAGCTTTGCTGAA

TGCTCCAGCCAAGATGTGGTGACCAAGCCTGATTGCAACTGCCTGTACCCCAAAGCCAT

CCCTAGCAGTGACCCGGCCTCTGTCTCCCCTCATCAGCCCCTCGCCCCCTCCATGGCCC

CTGTGGCTGGCTTGACCTGGGAGGACTCTGAGGGAACTGAGGGCAGCTCCCTCTTGCCT

GGTGAGCAGCCCCTGCACACAGTGGATCCAGGCAGTGCCAAGCAGCGGCCACCCAGGAG

CACCTGCCAGAGCTTTGAGCCGCCAGAGACCCCAGTTGTCAAGGACAGCACCATCGGTG

GCTCACCACAGCCTCGCCCCTCTGTCGGGGCCTTCAACCCCGGGATGGAGGATATTCTT

GACTCTGCAATGGGCACTAATTGGGTCCCAGAAGAAGCCTCTGGAGAGGCCAGTGAGAT

TCCCGTACCCCAAGGGACAGAGCTTTCCCCCTCCAGGCCAGGAGGGGGCAGCATGCAGA

CAGAGCCCGCCAGACCCAGCAACTTCCTCTCAGCATCTTCTCCACTCCCTGCATCAGCA

AAGGGCCAACAGCCGGCAGATGTAACTGGTACCGCCTTGCCCAGGGTGGGCCCCGTGAG

GCCCACTGGCCAGGACTGGAATCACACCCCCCAGAAGACAGACCATCCATCTGCCCTGC

TCAGAGACCCCCCGGAGCCAGGCTCTCCCAGGATCTCATCACTGCGCCCCCAGGGCCTC

AGCAACCCCTCCACCCTCTCTGCTCAGCCACAGCTTTCCAGAAGCCACTCCTCGGGCAG

CGTGCTGCCCCTTGGGGAGCTGGAGGGCAGGAGGAGCACCAGGGATCGGAGGAGCCCCG

CAGAGCCAGAAGGAGGACCAGCAAGTGAAGGGGCAGCCAGGCCCCTGCCCCGTTTTAAC

TCCGTTCCTTTGACTGACACAGGCCATGAGAGGCAGTCCGAGGGATCCTCCAGCCCGCA

GCTCCAGGAGTCTGTCTTCCACCTGCTGGTGCCCAGTGTCATCCTGGTCTTGCTGGCCG

TCGGAGGCCTCTTGTTCTACAGGTGGAGGCGGCGGAGCCATCAAGAGCCTCAGAGAGCG

GATTCTCCCTTGGAGCAACCAGAGGGCAGCCCCCTGACTCAGGATGACAGACAGGTGGA

ACTGCCAGTG
```

SEQ ID NO: 2:
*Homo sapiens* colony stimulating factor 1 (CSF1), transcript
variant 2 encoding isoform b (based on NM_172210.2), 1314 nucleotides
ATGACCGCGCCGGGCGCCGCCGGGCGCTGCCCTCCCACGACATGGCTGGGCTCCCTGCT

GTTGTTGGTCTGTCTCCTGGCGAGCAGGAGTATCACCGAGGAGGTGTCGGAGTACTGTA

GCCACATGATTGGGAGTGGACACCTGCAGTCTCTGCAGCGGCTGATTGACAGTCAGATG

GAGACCTCGTGCCAAATTACATTTGAGTTTGTAGACCAGGAACAGTTGAAAGATCCAGT

GTGCTACCTTAAGAAGGCATTTCTCCTGGTACAAGACATAATGGAGGACACCATGCGCT

TCAGAGATAACACCCCCAATGCCATCGCCATTGTGCAGCTGCAGGAACTCTCTTTGAGG

CTGAAGAGCTGCTTCACCAAGGATTATGAAGAGCATGACAAGGCCTGCGTCCGAACTTT

CTATGAGACACCTCTCCAGTTGCTGGAGAAGGTCAAGAATGTCTTTAATGAAACAAAGA

ATCTCCTTGACAAGGACTGGAATATTTTCAGCAAGAACTGCAACAACAGCTTTGCTGAA

TGCTCCAGCCAAGATGTGGTGACCAAGCCTGATTGCAACTGCCTGTACCCCAAAGCCAT

CCCTAGCAGTGACCCGGCCTCTGTCTCCCCTCATCAGCCCCTCGCCCCCTCCATGGCCC

CTGTGGCTGGCTTGACCTGGGAGGACTCTGAGGGAACTGAGGGCAGCTCCCTCTTGCCT

GGTGAGCAGCCCCTGCACACAGTGGATCCAGGCAGTGCCAAGCAGCGGCCACCCAGGAG

CACCTGCCAGAGCTTTGAGCCGCCAGAGACCCCAGTIGTCAAGGACAGCACCATCGGTG

GCTCACCACAGCCTCGCCCCTCTGTCGGGGCCTTCAACCCCGGGATGGAGGATATTCTT

GACTCTGCAATGGGCACTAATTGGGTCCCAGAAGAAGCCTCTGGAGAGGCCAGTGAGAT

TCCCGTACCCCAAGGGACAGAGCTTTCCCCCTCCAGGCCAGGAGGGGGCAGCATGCAGA

CAGAGCCCGCCAGACCCAGCAACTTCCTCTCAGCATCTTCTCCACTCCCTGCATCAGCA

AAGGGCCAACAGCCGGCAGATGTAACTGGCCATGAGAGGCAGTCCGAGGGATCCTCCAG

CCCGCAGCTCCAGGAGTCTGTCTTCCACCTGCTGGTGCCCAGTGTCATCCTGGTCTTGC

TGGCCGTCGGAGGCCTCTTGTTCTACAGGTGGAGGCGGCGGAGCCATCAAGAGCCTCAG

AGAGCGGATTCTCCCTTGGAGCAACCAGAGGGCAGCCCCCTGACTCAGGATGACAGACA

GGTGGAACTGCCAGTG

SEQ ID NO: 3:
*Homo sapiens* colony stimulating factor 1 (CSF1), transcript
variant 3 encoding isoform c (based on NM_172211.3), 619 nucleotides
ATGACCGCGCCGGGCGCCGCCGGGCGCTGCCCTCCCACGACATGGCTGGGCTCCCTGCT

GTTGTTGGTCTGTCTCCTGGCGAGCAGGAGTATCACCGAGGAGGTGTCGGAGTACTGTA

GCCACATGATTGGGAGTGGACACCTGCAGTCTCTGCAGCGGCTGATTGACAGTCAGATG

GAGACCTCGTGCCAAATTACATTTGAGTTTGTAGACCAGGAACAGTTGAAAGATCCAGT

GTGCTACCTTAAGAAGGCATTTCTCCTGGTACAAGACATAATGGAGGACACCATGCGCT

TCAGAGATAACACCCCCAATGCCATCGCCATTGTGCAGCTGCAGGAACTCTCTTTGAGG

CTGAAGAGCTGCTTCACCAAGGATTATGAAGAGCATGACAAGGCCTGCGTCCGAACTTT

CTATGAGACACCTCTCCAGTTGCTGGAGAAGGTCAAGAATGTCTTTAATGAAACAAAGA

ATCTCCTTGACAAGGACTGGAATATTTTCAGCAAGAACTGCAACAACAGCTTTGCTGAA

TGCTCCAGCCAAGGCCATGAGAGGCAGTCCGAGGGATCCTCCAGCCCGCAGCTCCAGGA

GTCTGTCTTCCACCTGCTGGTGCCCAGTG

SEQ ID NO: 4:
*Homo sapiens* colony stimulating factor 1 (CSF1), transcript
variant 4 encoding isoform a (based on NM_172212.2), 1662 nucleotides
ATGACCGCGCCGGGCGCCGCCGGGCGCTGCCCTCCCACGACATGGCTGGGCTCCCTGCT

GTTGTTGGTCTGTCTCCTGGCGAGCAGGAGTATCACCGAGGAGGTGTCGGAGTACTGTA

-continued

```
GCCACATGATTGGGAGTGGACACCTGCAGTCTCTGCAGCGGCTGATTGACAGTCAGATG

GAGACCTCGTGCCAAATTACATTTGAGTTTGTAGACCAGGAACAGTTGAAAGATCCAGT

GTGCTACCTTAAGAAGGCATTTCTCCTGGTACAAGACATAATGGAGGACACCATGCGCT

TCAGAGATAACACCCCCAATGCCATCGCCATTGTGCAGCTGCAGGAACTCTCTTTGAGG

CTGAAGAGCTGCTTCACCAAGGATTATGAAGAGCATGACAAGGCCTGCGTCCGAACTTT

CTATGAGACACCTCTCCAGTTGCTGGAGAAGGTCAAGAATGTCTTTAATGAAACAAAGA

ATCTCCTTGACAAGGACTGGAATATTTTCAGCAAGAACTGCAACAACAGCTTTGCTGAA

TGCTCCAGCCAAGATGTGGTGACCAAGCCTGATTGCAACTGCCTGTACCCCAAAGCCAT

CCCTAGCAGTGACCCGGCCTCTGTCTCCCCTCATCAGCCCCTCGCCCCCTCCATGGCCC

CTGTGGCTGGCTTGACCTGGGAGGACTCTGAGGGAACTGAGGGCAGCTCCCTCTTGCCT

GGTGAGCAGCCCCTGCACACAGTGGATCCAGGCAGTGCCAAGCAGCGGCCACCCAGGAG

CACCTGCCAGAGCTTTGAGCCGCCAGAGACCCCAGTIGTCAAGGACAGCACCATCGGTG

GCTCACCACAGCCTCGCCCCTCTGTCGGGGCCTTCAACCCCGGGATGGAGGATATTCTT

GACTCTGCAATGGGCACTAATTGGGTCCCAGAAGAAGCCTCTGGAGAGGCCAGTGAGAT

TCCCGTACCCCAAGGGACAGAGCTTTCCCCCTCCAGGCCAGGAGGGGGCAGCATGCAGA

CAGAGCCCGCCAGACCCAGCAACTTCCTCTCAGCATCTTCTCCACTCCCTGCATCAGCA

AAGGGCCAACAGCCGGCAGATGTAACTGGTACCGCCTTGCCCAGGGTGGGCCCCGTGAG

GCCCACTGGCCAGGACTGGAATCACACCCCCAGAAGACAGACCATCCATCTGCCCTGC

TCAGAGACCCCCCGGAGCCAGGCTCTCCCAGGATCTCATCACTGCGCCCCCAGGGCCTC

AGCAACCCCTCCACCCTCTCTGCTCAGCCACAGCTTTCCAGAAGCCACTCCTCGGGCAG

CGTGCTGCCCCTTGGGGAGCTGGAGGGCAGGAGGAGCACCAGGGATCGGAGGAGCCCCG

CAGAGCCAGAAGGAGGACCAGCAAGTGAAGGGGCAGCCAGGCCCCTGCCCCGTTTTAAC

TCCGTTCCTTTGACTGACACAGGCCATGAGAGGCAGTCCGAGGGATCCTCCAGCCCGCA

GCTCCAGGAGTCTGTCTTCCACCTGCTGGTGCCCAGTGTCATCCTGGTCTTGCTGGCCG

TCGGAGGCCTCTTGTTCTACAGGTGGAGGCGGCGGAGCCATCAAGAGCCTCAGAGAGCG

GATTCTCCCTTGGAGCAACCAGAGGGCAGCCCCCTGACTCAGGATGACAGACAGGTGGA

ACTGCCAGTG
```

SEQ ID NO: 5:
Amino acid sequence of human colony-stimulating factor 1 (hCSF1)
isoform a - 554 amino acids (including 32 amino acid N-terminal signal
peptide) (NP_000748.3)

```
MTAPGAAGRCPPTTWLGSLLLLVCLLASRSITEEVSEYCSHMIGSGHLQSLQRLIDSQM

ETSCQITFEFVDQEQLKDPVCYLKKAFLLVQDIMEDTMRFRDNTPNAIAIVQLQELSLR

LKSCFTKDYEEHDKACVRTFYETPLQLLEKVKNVFNETKNLLDKDWNIFSKNCNNSFAE

CSSQDVVTKPDCNCLYPKAIPSSDPASVSPHQPLAPSMAPVAGLTWEDSEGTEGSSLLP

GEQPLHTVDPGSAKQRPPRSTCQSFEPPETPVVKDSTIGGSPQPRPSVGAFNPGMEDIL

DSAMGTNWVPEEASGEASEIPVPQGTELSPSRPGGGSMQTEPARPSNFLSASSPLPASA

KGQQPADVTGTALPRVGPVRPTGQDWNHTPQKTDHPSALLRDPPEPGSPRISSLRPQGL

SNPSTLSAQPQLSRSHSSGSVLPLGELEGRRSTRDRRSPAEPEGGPASEGAARPLPRFN

SVPLTDTGHERQSEGSSSPQLQESVFHLLVPSVILVLLAVGGLLFYRWRRRSHQEPQRA

DSPLEQPEGSPLTQDDRQVELPV
```

SEQ ID NO: 6:
Amino acid sequence of human colony-stimulating factor 1 (hCSF1)
without signal peptide - 522 amino acids (based on NP_000748.3)
EEVSEYCSHMIGSGHLQSLQRLIDSQMETSCQITFEFVDQEQLKDPVCYLKKAFLLVQD

IMEDTMRFRDNTPNAIAIVQLQELSLRLKSCFTKDYEEHDKACVRTFYETPLQLLEKVK

NVFNETKNLLDKDWNIFSKNCNNSFAECSSQDVVTKPDCNCLYPKAIPSSDPASVSPHQ

PLAPSMAPVAGLTWEDSEGTEGSSLLPGEQPLHTVDPGSAKQRPPRSTCQSFEPPETPV

VKDSTIGGSPQPRPSVGAFNPGMEDILDSAMGTNWVPEEASGEASEIPVPQGTELSPSR

PGGGSMQTEPARPSNFLSASSPLPASAKGQQPADVTGTALPRVGPVRPTGQDWNHTPQK

TDHPSALLRDPPEPGSPRISSLRPQGLSNPSTLSAQPQLSRSHSSGSVLPLGELEGRRS

TRDRRSPAEPEGGPASEGAARPLPRFNSVPLTDTGHERQSEGSSSPQLQESVFHLLVPS

VILVLLAVGGLLFYRWRRRSHQEPQRADSPLEQPEGSPLTQDDRQVELPV

SEQ ID NO: 7:
Amino acid sequence of human colony-stimulating factor 1 (hCSF1)
isoform b - 438 amino acids (including 32 amino acid N-terminal signal
peptide) - (NP_757349.1) encoded by transcript variant 2
MTAPGAAGRCPPTTWLGSLLLLVCLLASRSITEEVSEYCSHMIGSGHLQSLQRLIDSQM

ETSCQITFEFVDQEQLKDPVCYLKKAFLLVQDIMEDTMRFRDNTPNAIAIVQLQELSLR

LKSCFTKDYEEHDKACVRTFYETPLQLLEKVKNVFNETKNLLDKDWNIFSKNCNNSFAE

CSSQDVVTKPDCNCLYPKAIPSSDPASVSPHQPLAPSMAPVAGLTWEDSEGTEGSSLLP

GEQPLHTVDPGSAKQRPPRSTCQSFEPPETPVVKDSTIGGSPQPRPSVGAFNPGMEDIL

DSAMGTNWVPEEASGEASEIPVPQGTELSPSRPGGGSMQTEPARPSNFLSASSPLPASA

KGQQPADVTGHERQSEGSSSPQLQESVFHLLVPSVILVLLAVGGLLFYRWRRRSHQEPQ

RADSPLEQPEGSPLTQDDRQVELPV

SEQ ID NO: 8:
Amino acid sequence of human colony-stimulating factor 1 (hCSF1)
isoform b without signal peptide - 406 amino acids (based on NP_757349.1)
EEVSEYCSHMIGSGHLQSLQRLIDSQMETSCQITFEFVDQEQLKDPVCYLKKAFLLVQD

IMEDTMRFRDNTPNAIAIVQLQELSLRLKSCFTKDYEEHDKACVRTFYETPLQLLEKVK

NVFNETKNLLDKDWNIFSKNCNNSFAECSSQDVVTKPDCNCLYPKAIPSSDPASVSPHQ

PLAPSMAPVAGLTWEDSEGTEGSSLLPGEQPLHTVDPGSAKQRPPRSTCQSFEPPETPV

VKDSTIGGSPQPRPSVGAFNPGMEDILDSAMGTNWVPEEASGEASEIPVPQGTELSPSR

PGGGSMQTEPARPSNFLSASSPLPASAKGQQPADVTGHERQSEGSSSPQLQESVFHLLV

PSVILVLLAVGGLLFYRWRRRSHQEPQRADSPLEQPEGSPLTQDDRQVELPV

SEQ ID NO: 9:
Amino acid sequence of human colony-stimulating factor 1 (hCSF1)
isoform c - 256 amino acids- (including 32 amino acid N-terminal signal
peptide) (NP_757350.1) encoded by transcript variant 3
MTAPGAAGRCPPTTWLGSLLLLVCLLASRSITEEVSEYCSHMIGSGHLQSLQRLIDSQM

ETSCQITFEFVDQEQLKDPVCYLKKAFLLVQDIMEDTMRFRDNTPNAIAIVQLQELSLR

LKSCFTKDYEEHDKACVRTFYETPLQLLEKVKNVFNETKNLLDKDWNIFSKNCNNSFAE

CSSQGHERQSEGSSSPQLQESVFHLLVPSVILVLLAVGGLLFYRWRRRSHQEPQRADSP

LEQPEGSPLTQDDRQVELPV

-continued

SEQ ID NO: 10:
Amino acid sequence of human colony-stimulating factor 1 (hCSF1)
isoform c without signal peptide - 224 amino acids (based on NP_757350.1)
EEVSEYCSHMIGSGHLQSLQRLIDSQMETSCQITFEFVDQEQLKDPVCYLKKAFLLVQD

IMEDTMRFRDNTPNAIAIVQLQELSLRLKSCFTKDYEEHDKACVRTFYETPLQLLEKVK

NVFNETKNLLDKDWNIFSKNCNNSFAECSSQGHERQSEGSSSPQLQESVFHLLVPSVIL

VLLAVGGLLFYRWRRRSHQEPQRADSPLEQPEGSPLTQDDRQVELPV

SEQ ID NO. 11:
human SCF 220 (245 aa)
MKKTQTWILTCIYLQLLLFNPLVKTEGICRNRVTNNVKDVTKLVANLPKDYMITLKYVP

GMDVLPSHCWISEMVVQLSDSLTDLLDKFSNISEGLSNYSIIDKLVNIVDDLVECVKEN

SSKDLKKSFKSPEPRLFTPEEFFRIFNRSIDAFKDFVVASETSDCVVSSTLSPEKGKAK

NPPGDSSLHWAAMALPALFSLIIGFAFGALYWKKRQPSLTRAVENIQINEEDNEISMLQ

EKEREFQEV

SEQ ID NO. 12:
Nucleotide Sequence encoding human SCF 220, 738
nucleotides
ATGAAGAAGACACAAACTTGGATTCTCACTTGCATTTATCTTCAGCTGCTCCTATTTAA

TCCTCTCGTCAAAACTGAAGGGATCTGCAGGAATCGTGTGACTAATAATGTAAAAGACG

TCACTAAATTGGTGGCAAATCTTCCAAAAGACTACATGATAACCCTCAAATATGTCCCC

GGGATGGATGTTTTGCCAAGTCATTGTTGGATAAGCGAGATGGTAGTACAATTGTCAGA

CAGCTTGACTGATCTTCTGGACAAGTTTTCAAATATTTCTGAAGGCTTGAGTAATTATT

CCATCATAGACAAACTTGTGAATATAGTGGATGACCTTGTGGAGTGCGTGAAAGAAAAC

TCATCTAAGGATCTAAAAAAATCATTCAAGAGCCCAGAACCCAGGCTCTTTACTCCTGA

AGAATTCTTTAGAATTTTTAATAGATCCATTGATGCCTTCAAGGACTTTGTAGTGGCAT

CTGAAACTAGTGATTGTGTGGTTTCTTCAACATTAAGTCCTGAGAAAGGGAAGGCCAAA

AATCCCCCTGGAGACTCCAGCCTACACTGGGCAGCCATGGCATTGCCAGCATTGTTTTC

TCTTATAATTGGCTTTGCTTTTGGAGCCTTATACTGGAAGAAGAGACAGCCAAGTCTTA

CAAGGGCAGTTGAAAATATACAAATTAATGAAGAGGATAATGAGATAAGTATGTTGCAA

GAGAAAGAGAGAGAGTTTCAAGAAGTGTAA

SEQ ID NO. 13:
human SCF 248 (273 aa)
MKKTQTWILTCIYLQLLLFNPLVKTEGICRNRVTNNVKDVTKLVANLPKDYMITLKYVP

GMDVLPSHCWISEMVVQLSDSLTDLLDKFSNISEGLSNYSIIDKLVNIVDDLVECVKEN

SSKDLKKSFKSPEPRLFTPEEFFRIFNRSIDAFKDFVVASETSDCVVSSTLSPEKDSRV

SVTKPFMLPPVAASSLRNDSSSSNRKAKNPPGDSSLHWAAMALPALFSLIIGFAFGALY

WKKRQPSLTRAVENIQINEEDNEISMLQEKEREFQEV

SEQ ID NO. 14:
Nucleotide Sequence encoding human SCF 248, 822 nucleotides
ATGAAGAAGACACAAACTTGGATTCTCACTTGCATTTATCTTCAGCTGCTCCTATTTAA

TCCTCTCGTCAAAACTGAAGGGATCTGCAGGAATCGTGTGACTAATAATGTAAAAGACG

TCACTAAATTGGTGGCAAATCTTCCAAAAGACTACATGATAACCCTCAAATATGTCCCC

GGGATGGATGTTTTGCCAAGTCATTGTTGGATAAGCGAGATGGTAGTACAATTGTCAGA

CAGCTTGACTGATCTTCTGGACAAGTTTTCAAATATTTCTGAAGGCTTGAGTAATTATT

CCATCATAGACAAACTTGTGAATATAGTGGATGACCTTGTGGAGTGCGTGAAAGAAAAC

TCATCTAAGGATCTAAAAAAATCATTCAAGAGCCCAGAACCCAGGCTCTTTACTCCTGA

-continued

AGAATTCTTTAGAATTTTTAATAGATCCATTGATGCCTTCAAGGACTTTGTAGTGGCAT

CTGAAACTAGTGATTGTGTGGTTTCTTCAACATTAAGTCCTGAGAAAGATTCCAGAGTC

AGTGTCACAAAACCATTTATGTTACCCCCTGTTGCAGCCAGCTCCCTTAGGAATGACAG

CAGTAGCAGTAATAGGAAGGCCAAAAATCCCCCTGGAGACTCCAGCCTACACTGGGCAG

CCATGGCATTGCCAGCATTGTTTTCTCTTATAATTGGCTTTGCTTTTGGAGCCTTATAC

TGGAAGAAGAGACAGCCAAGTCTTACAAGGGCAGTTGAAAATATACAAATTAATGAAGA

GGATAATGAGATAAGTATGTTGCAAGAGAAAGAGAGAGTTTCAAGAAGTGTAA

SEQ ID NO. 15:
nucleotide sequence encoding human SCF 248 including
5' and 3' non-coding sequences, 1405 nucleotides
CCGCCTCGCGCCGAGACTAGAAGCGCTGCGGGAAGCAGGGACAGTGGAGAGGGCGCTGC

GCTCGGGCTACCCAATGCGTGGACTATCTGCCGCCGCTGTTCGTGCAATATGCTGGAGC

TCCAGAACAGCTAAACGGAGTCGCCACACCACTGTTTGTGCTGGATCGCAGCGCTGCCT

TTCCTTATGAAGAAGACACAAACTTGGATTCTCACTTGCATTTATCTTCAGCTGCTCCT

ATTTAATCCTCTCGTCAAAACTGAAGGGATCTGCAGGAATCGTGTGACTAATAATGTAA

AAGACGTCACTAAATTGGTGGCAAATCTTCCAAAAGACTACATGATAACCCTCAAATAT

GTCCCCGGGATGGATGTTTTGCCAAGTCATTGTTGGATAAGCGAGATGGTAGTACAATT

GTCAGACAGCTTGACTGATCTTCTGGACAAGTTTTCAAATATTTCTGAAGGCTTGAGTA

ATTATTCCATCATAGACAAACTTGTGAATATAGTGGATGACCTTGTGGAGTGCGTGAAA

GAAAACTCATCTAAGGATCTAAAAAAATCATTCAAGAGCCCAGAACCCAGGCTCTTTAC

TCCTGAAGAATTCTTTAGAATTTTTAATAGATCCATTGATGCCTTCAAGGACTTTGTAG

TGGCATCTGAAACTAGTGATTGTGTGGTTTCTTCAACATTAAGTCCTGAGAAAGATTCC

AGAGTCAGTGTCACAAAACCATTTATGTTACCCCCTGTTGCAGCCAGCTCCCTTAGGAA

TGACAGCAGTAGCAGTAATAGGAAGGCCAAAAATCCCCCTGGAGACTCCAGCCTACACT

GGGCAGCCATGGCATTGCCAGCATTGTTTTCTCTTATAATTGGCTTTGCTTTTGGAGCC

TTATACTGGAAGAAGAGACAGCCAAGTCTTACAAGGGCAGTTGAAAATATACAAATTAA

TGAAGAGGATAATGAGATAAGTATGTTGCAAGAGAAAGAGAGAGTTTCAAGAAGTGT

AAATTGTGGCTTGTATCAACACTGTTACTTTCGTACATTGGCTGGTAACAGTTCATGTT

TGCTTCATAAATGAAGCAGCTTTAAACAAATTCATATTCTGTCTGGAGTGACAGACCAC

ATCTTTATCTGTTCTTGCTACCCATGACTTTATATGGATGATTCAGAAATTGGAACAGA

ATGTTTTACTGTGAAACTGGCACTGAATTAATCATCTATAAAGAAGAACTTGCATGGAG

CAGGACTCTATTTTAAGGACTGCGGGACTTGGGTCTCATTTAGAACTTGCAGCTGATGT

TGGAAGAGAAAGCACGTGTCTCAGACTGCATGTACCATTTGCATGGCTCCAGAAATGTC

TAAATGCTGAAAAACACCTAGCTTTATTCTTCAGATACAAACTGCAG

SEQ ID NO. 16:
human soluble SCF (164 aa and 25 aa N-terminal signal
peptide)
MKKTQTWILTCIYLQLLLFNPLVKTEGICRNRVTNNVKDVTKLVANLPKDYMITLKYVP

GMDVLPSHCWISEMVVQLSDSLTDLLDKFSNISEGLSNYSIIDKLVNIVDDLVECVKEN

SSKDLKKSFKSPEPRLFTPEEFFRIFNRSIDAFKDFVVASETSDCVVSSTLSPEKDSRV

SVTKPFMLPPVA

SEQ ID NO. 17:
nucleotide sequence encoding human soluble SCF (164
aa and 25 aa N-terminal signal peptide), 567 nucleotides
ATGAAGAAGACACAAACTTGGATTCTCACTTGCATTTATCTTCAGCTGCTCCTATTTAA

TCCTCTCGTCAAAACTGAAGGGATCTGCAGGAATCGTGTGACTAATAATGTAAAAGACG

TCACTAAATTGGTGGCAAATCTTCCAAAAGACTACATGATAACCCTCAAATATGTCCCC

GGGATGGATGTTTTGCCAAGTCATTGTTGGATAAGCGAGATGGTAGTACAATTGTCAGA

CAGCTTGACTGATCTTCTGGACAAGTTTTCAAATATTTCTGAAGGCTTGAGTAATTATT

CCATCATAGACAAACTTGTGAATATAGTGGATGACCTTGTGGAGTGCGTGAAAGAAAAC

TCATCTAAGGATCTAAAAAAATCATTCAAGAGCCCAGAACCCAGGCTCTTTACTCCTGA

AGAATTCTTTAGAATTTTTAATAGATCCATTGATGCCTTCAAGGACTTTGTAGTGGCAT

CTGAAACTAGTGATTGTGTGGTTTCTTCAACATTAAGTCCTGAGAAAGATTCCAGAGTC

AGTGTCACAAAACCATTTATGTTACCCCCTGTTGCA

SEQ ID NO: 18:
hGM-CSF - 144 amino acids (including 17 amino acid
signal peptide)
MWLQSLLLLGTVACSISAPARSPSPSTQPWEHVNAIQEARRLLNLSRDTAAEMNETVEV

ISEMFDLQEPTCLQTRLELYKQGLRGSLIKLKGPLTMMASHYKQHCPPTPETSCATQII

TFESFKENLKDFLLVIPFDCWEPVQE

SEQ ID NO: 19:
Nucleotide sequence encoding hGM-CSF (including 17
amino acid signal peptide) - 435 nucleotides
atgtggctgcagagcctgctgctcttgggcactgtggcctgcagcatctctgcacccgc ccgctcgcccagccccagcacgcagccctgggagcatgtgaatgccatccaggaggccc ggcgtctcctgaacctgagtagagacactgctgctgagatgaatgaaacagtagaagtc atctcagaaatgtttgacctccaggagccgacctgcctacagacccgcctggagctgta caagcagggcctgcggggcagcctcaccaagctcaagggccccttgaccatgatggcca gccactacaagcagcactgccctccaaccccggaaacttcctgtgcaacccagattatc acctttgaaagtttcaaagagaacctgaaggactttctgcttgtcatccccttttgactg ctgggagccagtccaggagtga SEQ ID NO: 20:
hGM-CSF without signal peptide - 127 amino acids
APARSPSPSTQPWEHVNAIQEARRLLNLSRDTAAEMNETVEVISEMFDLQEPTCLQTRL

ELYKQGLRGSLTKLKGPLTMMASHYKQHCPPTPETSCATQIITFESFKENLKDFLLVIP

FDCWEPVQE

SEQ ID NO: 21:
Nucleotide sequence encoding hGM-CSF protein without
signal peptide -352 nucleotides
gccctgggagcatgtgaatgccatccaggaggcccggcgtctcctgaacctgagtagag acactgctgctgagatgaatgaaacagtagaagtcatctcagaaatgtttgacctccag gagccgacctgcctacagacccgcctggagctgtacaagcagggcctgcggggcagcct caccaagctcaagggccccttgaccatgatggccagccactacaagcagcactgccctc caaccccggaaacttcctgtgcaacccagattatcacctttgaaagtttcaaagagaac ctgaaggactttctgcttgtcatccccttttgactgctgggagccagtccaggagtga -continued SEQ ID NO: 22:
human interleukin-3 152 amino acids (including 19
amino acid signal peptide)
MSRLPVLLLLQLLVRPGLQAPMTQTTPLKTSWVNCSNMIDEIITHLKQPPLPLLDFNNL

NGEDQDILMENNLRRPNLEAFNRAVKSLQNASAIESILKNLLPCLPLATAAPTRHPIHI

KDGDWNEFRRKLTFYLKTLENAQAQQTTLSLAIF

SEQ ID NO: 23:
Nucleotide sequence encoding interleukin-3 (including
19 amino acid signal peptide)-459 nucleotides
atgagccgcctgcccgtcctgctcctgctccaactcctggtccgccccggactccaagc tcccatgacccagacaacgcccttgaagacaagctgggttaactgctctaacatgatcg atgaaattataacacacttaaagcagccacctttgcctttgctggacttcaacaacctc aatggggaagaccaagacattctgatggaaaataaccttcgaaggccaaacctggaggc attcaacagggctgtcaagagtttacagaacgcatcagcaattgagagcattcttaaaa atctcctgccatgtctgcccctggccacggccgcacccacgcgacatccaatccatatc aaggacggtgactggaatgaattccggaggaaactgacgttctatctgaaaacccttga gaatgcgcaggctcaacagacgactttgagcctcgcgatcttttga SEQ ID NO: 24:
human interleukin-3 without signal peptide - 133 amino acids
APMTQTTPLKTSWVNCSNMIDEIITHLKQPPLPLLDENNLNGEDQDILMENNLRRPNLE

AFNRAVKSLQNASAIESILKNLLPCLPLATAAPTRHPIHIKDGDWNEFRRKLTFYLKTL

ENAQAQQTTLSLAIF

SEQ ID NO: 25:
Nucleotide sequence encoding interleukin-3 without
signal peptide-402 nucleotides
gctcccatgacccagacaacgcccttgaagacaagctgggttaactgctctaacatgat cgatgaaattataacacacttaaagcagccacctttgcctttgctggacttcaacaacc tcaatggggaagaccaagacattctgatggaaaataaccttcgaaggccaaacctggag gcattcaacagggctgtcaagagtttacagaacgcatcagcaattgagagcattcttaa aaatctcctgccatgtctgcccctggccacggccgcacccacgcgacatccaatccata tcaaggacggtgactggaatgaattccggaggaaactgacgttctatctgaaaaccctt gagaatgcgcaggctcaacagacgactttgagcctcgcgatcttttga

---

The invention claimed is:

1. A method for assessing anti-tumor efficacy of an immunotherapy, the method comprising:

administering an immunotherapy to an immunodeficient transgenic mouse whose genome expresses a transgene encoding human stem cell factor (hSCF), a transgene encoding human granulocyte-macrophage colony-stimulating factor (hGM-CSF), a transgene encoding human interleukin-3 (hIL-3), and a transgene encoding human colony-stimulating factor 1 (hCSF1), wherein the immunodeficient transgenic mouse has been humanized and engrafted with a human tumor xenograft, wherein the immunodeficient transgenic mouse (a) comprises fewer numbers of human CD20+ cells and increased numbers of human CD3+ cells, CD33+ cells, CD14+ cells, and CD56+ cells as a proportion of human CD45+ cells relative to a control mouse, (b) displays an increase in the relative number of human CD14+ macrophages and human CD56+ natural killer cells and increased concentrations of macrophage-secreted cytokines relative to a control mouse, and (c) the control mouse is an immunodeficient transgenic mouse whose genome expresses a transgene encoding hSCF, a transgene encoding hGM-CSF, and a transgene encoding hIL-3, and not a transgene encoding hCSF1; and assessing anti-tumor efficacy of the immunotherapy.

2. The method of claim 1, wherein the genome of the immunodeficient transgenic mouse is homozygous for the Prkdc$^{scid}$ allele.

3. The method of claim 1, wherein the genome of the immunodeficient transgenic mouse is homozygous for the Il2rg$^{tm1Wjl}$ allele.

4. The method of claim 1, wherein the genome of the immunodeficient transgenic mouse is homozygous for the Prkdc$^{scid}$ allele and is homozygous for the Il2rg$^{tm1Wjl}$ allele.

5. The method of claim 1, wherein in the absence of an immunological challenge peripheral blood of the immunodeficient transgenic mouse comprises human CD45+ cells, and wherein:

at least about 20% of the human CD45+ cells are CD3+ CD45+ cells;

at least about 10% of the human CD45+ cells are CD33+ CD45+ cells;

at least about 5% of the human CD45+ cells are CD14+ CD45+ cells; and/or at least about 0.5% of the human CD45+ cells are CD56+CD45+ cells.

6. The method of claim 1, wherein the assessing anti-tumor efficacy comprises measuring tumor growth in the immunodeficient transgenic mouse.

7. The method of claim 1, wherein the assessing anti-tumor efficacy comprises measuring tumor size in the immunodeficient transgenic mouse.

8. The method of claim 1, wherein the assessing anti-tumor efficacy comprises measuring human cytokines in serum obtained from the immunodeficient transgenic mouse.

9. The method of claim 1, wherein the immunotherapy is a checkpoint inhibitor.

10. The method of claim 1, wherein the immunotherapy is an antibody.

* * * * *